US007893256B2

(12) United States Patent
Mammen et al.

(10) Patent No.: US 7,893,256 B2
(45) Date of Patent: Feb. 22, 2011

(54) AZABICYCLOALKANE COMPOUNDS

(75) Inventors: Mathai Mammen, Menlo Park, CA (US); Adam Hughes, Belmont, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 12/756,694

(22) Filed: Apr. 8, 2010

(65) Prior Publication Data

US 2010/0197922 A1 Aug. 5, 2010

Related U.S. Application Data

(62) Division of application No. 12/069,168, filed on Feb. 7, 2008, now Pat. No. 7,732,441, which is a division of application No. 10/854,829, filed on May 27, 2004, now Pat. No. 7,358,244.

(60) Provisional application No. 60/473,761, filed on May 28, 2003.

(51) Int. Cl.
*C07D 221/22* (2006.01)
*C07D 45/02* (2006.01)
*C07D 417/00* (2006.01)

(52) U.S. Cl. ......................... 544/61; 544/127; 544/180; 544/238; 544/335; 546/89; 546/97; 546/124; 546/125; 546/126; 546/127

(58) Field of Classification Search .................. 544/61, 544/127, 180, 238, 335; 546/89, 97, 124
See application file for complete search history.

(56) References Cited

U.S. PATENT DOCUMENTS

| | | | | |
|---|---|---|---|---|
| 3,505,337 | A | 4/1970 | Zeile et al. | |
| 4,026,897 | A | 5/1977 | Nakagawa et al. | |
| 4,460,581 | A | 7/1984 | Schromm et al. | |
| 4,894,219 | A | 1/1990 | Baker et al. | |
| 4,992,474 | A | 2/1991 | Skidmore et al. | |
| 5,610,163 | A | 3/1997 | Banholzer et al. | |
| 5,654,314 | A | 8/1997 | Banholzer et al. | |
| 5,770,738 | A | 6/1998 | Banholzer et al. | |
| 6,268,533 | B1 | 7/2001 | Gao et al. | |
| 6,362,371 | B1 | 3/2002 | Moran et al. | |
| 6,433,027 | B1 | 8/2002 | Bozung et al. | |
| 6,455,524 | B1 | 9/2002 | Bozung et al. | |
| 6,541,669 | B1 | 4/2003 | Moran et al. | |
| 6,576,793 | B1 | 6/2003 | Moran et al. | |
| 6,593,497 | B1 | 7/2003 | Choi et al. | |
| 6,653,323 | B2 | 11/2003 | Moran et al. | |
| 6,670,376 | B1 | 12/2003 | Moran et al. | |
| 6,693,202 | B1 | 2/2004 | Aggen et al. | |
| 6,713,651 | B1 | 3/2004 | Moran et al. | |
| 6,747,043 | B2 | 6/2004 | Moran et al. | |
| 7,141,671 | B2 | 11/2006 | Mammen et al. | |
| 7,358,244 | B2 * | 4/2008 | Mammen et al. | 514/228.2 |
| 7,732,441 | B2 * | 6/2010 | Mammen et al. | 514/228.2 |
| 2002/0111363 | A1 | 8/2002 | Drechsel et al. | |
| 2002/0115681 | A1 | 8/2002 | Bozung et al. | |
| 2003/0018019 | A1 | 1/2003 | Meade et al. | |
| 2003/0055080 | A1 | 3/2003 | Fomer et al. | |
| 2004/0209860 | A1 | 10/2004 | Mammen et al. | |
| 2004/0209915 | A1 | 10/2004 | Mammen et al. | |

FOREIGN PATENT DOCUMENTS

| | | | |
|---|---|---|---|
| EP | 0 418 716 | A1 | 3/1991 |
| WO | WO 99/64031 | A1 | 12/1999 |
| WO | WO 99/64035 | A1 | 12/1999 |
| WO | WO 99/64043 | A1 | 12/1999 |
| WO | WO 01/04118 | A2 | 1/2001 |
| WO | WO 02/051841 | A1 | 7/2002 |
| WO | WO 02/053564 | A2 | 7/2002 |
| WO | WO 02/066422 | A1 | 8/2002 |
| WO | WO 03/053966 | A2 | 7/2003 |
| WO | WO 03/087096 | A1 | 10/2003 |
| WO | WO 2004/048373 | A1 | 6/2004 |
| WO | WO 2004/089892 | A2 | 10/2004 |

OTHER PUBLICATIONS

Barnes, "Tiotropium bromide", Exp. Opin. Invest. Drugs, 10(4), pp. 733-740 (2001).

Zlotos et al., "Muscarinic receptor agonists and antagonists", Exp. Opin. Ther. Patents, 9(8), pp. 1029-1053 (1999).

* cited by examiner

*Primary Examiner*—Janet L. Andres
*Assistant Examiner*—Raymond Covington
(74) *Attorney, Agent, or Firm*—Jeffrey A. Hagenah

(57) ABSTRACT

This invention provides compounds of formula I:

I

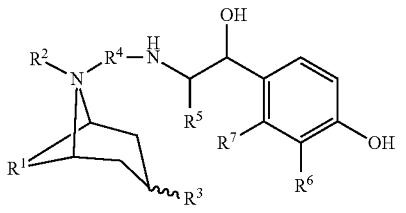

wherein $R^1$, $R^2$, $R^3$, $R^4$, $R^5$, $R^6$ and $R^7$ are as defined in the specification, or a pharmaceutically acceptable salt or solvate or stereoisomer thereof. The compounds of this invention possess both $\beta_2$ adrenergic receptor agonist and muscarinic receptor antagonist activity. Such compounds are useful for treating pulmonary disorders, such as chronic obstructive pulmonary disease and asthma.

9 Claims, No Drawings

AZABICYCLOALKANE COMPOUNDS

CROSS-REFERENCE TO RELATED APPLICATIONS

This application is a divisional application of U.S. application Ser. No. 12/069,168, filed Feb. 7, 2008; which application is a divisional of U.S. application Ser. No. 10/854,829, filed May 27, 2004 (now U.S. Pat. No. 7,358,244 B2), which application claims the benefit of U.S. Provisional Application No. 60/473,761, filed on May 28, 2003; the entire disclosures of which are incorporated herein by reference in their entirety.

BACKGROUND OF THE INVENTION

1. Field of the Invention

The present invention relates to novel azabicycloalkane and related compounds having both $\beta_2$ adrenergic receptor agonist and muscarinic receptor antagonist activity. This invention also relates to pharmaceutical compositions comprising such compounds, processes and intermediates for preparing such compounds and methods of using such compounds to treat pulmonary disorders.

2. State of the Art

Pulmonary disorders, such as asthma and chronic obstructive pulmonary disease (COPD), are commonly treated with bronchodilators. One class of bronchodilator in widespread use consists of $\beta_2$ adrenergic receptor (adrenoceptor) agonists, such as albuterol, formoterol and salmeterol. These compounds are generally administered by inhalation. Another class of bronchodilator consists of muscarinic receptor antagonists (anticholinergic compounds), such as ipratropium and tiotropium. These compounds are also typically administered by inhalation.

Pharmaceutical compositions containing both a $\beta_2$ adrenergic receptor agonist and a muscarinic receptor antagonist are also known in the art for use in treating pulmonary disorders. For example, U.S. Pat. No. 6,433,027 discloses medicament compositions containing a muscarinic receptor antagonist, such as tiotropium bromide, and a $\beta_2$ adrenergic receptor agonist, such as formoterol fumarate.

Although compounds having either $\beta_2$ adrenergic receptor agonist or muscarinic receptor antagonist activity are known, no compound having both $\beta_2$ adrenergic receptor agonist and muscarinic receptor antagonist activity has been previously disclosed. Compounds possessing both $\beta_2$ adrenergic receptor agonist and muscarinic receptor antagonist activity are highly desirable since such bifunctional compounds would provide bronchodilation through two independent modes of action while having single molecule pharmacokinetics.

SUMMARY OF THE INVENTION

The present invention provides novel azabicycloalkane and related compounds that are useful for treating pulmonary disorders. Among other properties, compounds of this invention have been found to possess both $\beta_2$ adrenergic receptor agonist and muscarinic receptor antagonist activity.

Accordingly, in one of its composition aspects, the present invention is directed to a compound of formula I:

I

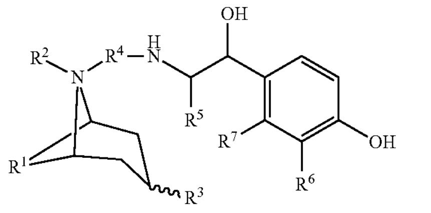

wherein $R^1$ represents $-CH_2CH_2-$, $-CH{=}CH-$, $-CH_2CH_2CH_2-$, $-CH_2CH(OCH_3)-$ or

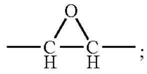

;

$R^2$ represents an electron pair or (1-6C)alkyl which is unsubstituted or substituted with a hydroxy group or from 1 to 3 fluoro substituents; provided that when $R^2$ is an alkyl group, the nitrogen atom to which it is attached is positively charged and a pharmaceutically acceptable anion, $X^-$, is present;

$R^3$ represents $-OC(O)CR^{3a}R^{3b}R^{3c}$ or $-NHC(O)R^{3d}$;

$R^{3a}$ represents hydrogen, hydroxy, (1-4C)alkyl or hydroxy (1-4C)alkyl;

$R^{3b}$ represents phenyl, (3-6C)cycloalkyl, (3-5C)heteroaryl or (3-5C)heterocyclyl; wherein each phenyl, cycloalkyl, heteroaryl and heterocyclyl group is unsubstituted or substituted with from 1 to 4 substituents selected independently from halo, (1-4C)alkyl and (1-4C)alkoxy; and wherein the heteroaryl and heterocyclyl groups contain 1 or 2 ring heteroatoms selected independently from oxygen, nitrogen and sulfur;

$R^{3c}$ represents hydrogen, phenyl, (3-6C)cycloalkyl, (3-5C) heteroaryl or (3-5C)heterocyclyl; wherein each phenyl, cycloalkyl, heteroaryl and heterocyclyl group is unsubstituted or substituted with from 1 to 4 substituents selected independently from halo, (1-4C)alkyl and (1-4C)alkoxy; and wherein the heteroaryl and heterocyclyl groups contain 1 or 2 ring heteroatoms selected independently from oxygen, nitrogen and sulfur;

or $R^{3b}$ and $R^{3c}$ together with $R^{3a}$ and the carbon atom to which they are attached form a group of formula (a):

(a)

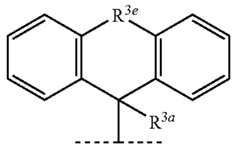

wherein $R^{3e}$ represents $-O-$, $-S-$, $-CH_2-$, $-CH_2CH_2-$, $-CH_2O-$, or $-CH_2S-$;

$R^{3d}$ represents an indazol-3-yl group which is unsubstituted or substituted with (1-4C)alkyl at the 1-position;

$R^4$ is a divalent group of the formula:

$$-(R^{4a})_d-(A^1)_e-(R^{4b})_f-Q-(R^{4c})_g-(A^2)_h-(R^{4d})_i-$$

wherein d, e, f, g, h and i are each independently selected from 0 and 1;

$R^{4a}$, $R^{4b}$, $R^{4c}$ and $R^{4d}$ are each independently selected from (1-10C)alkylene, (2-10C)alkenylene and (2-10C)alkynylene, wherein each alkylene, alkenylene or alkynylene group is unsubstituted or substituted with from 1 to 5 substituents independently selected from (1-4C)alkyl, fluoro, hydroxy, phenyl and phenyl-(1-4C)alkyl; or led represents (1-6C)alkylene-NHC(O)-(1-6C)alkylene;

$A^1$ and $A^2$ are each independently selected from (3-7C) cycloalkylene, (6-10C)arylene, —O-(6-10C)arylene, (6-10C)arylene-O—, (2-9C)heteroarylene, —O-(2-9C)heteroarylene, (2-9C)heteroarylene-O— and (3-6C)heterocyclene, wherein each cycloalkylene is unsubstituted or substituted with from 1 to 4 substituents selected independently from (1-4C)alkyl, and each arylene, heteroarylene or heterocyclene group is unsubstituted or substituted with from 1 to 4 substituents independently selected from halo, (1-4C)alkyl, (1-4C)alkoxy, —S-(1-4C)alkyl, —S(O)-(1-4C)alkyl, —$S(O)_2$-(1-4C)alkyl, —C(O)O(1-4C)alkyl, carboxy, cyano, hydroxy, nitro, trifluoromethyl and trifluoromethoxy;

Q is selected from a bond, —O—, —C(O)O—, —OC(O)—, —S—, —S(O)—, —$S(O)_2$—, —N($Q^a$)C(O)—, —C(O)N($Q^b$)-, —N($Q^c$)$S(O)_2$—, —$S(O)_2$N($Q^d$)-, —N($Q^e$)C(O)N($Q^f$)-, —N($Q^g$)$S(O)_2$N($Q^h$)-, —OC(O)N($Q^i$)-, —N($Q^j$)C(O)O— and —N($Q^k$);

$Q^a$, $Q^b$, $Q^c$, $Q^d$, $Q^e$, $Q^f$, $Q^g$, $Q^h$, $Q^i$, $Q^j$ and $Q^k$ are each independently selected from hydrogen, (1-6C)alkyl, $A^3$ and (1-4C)alkylene-$A^4$, wherein the alkyl group is unsubstituted or substituted with from 1 to 3 substituents independently selected from fluoro, hydroxy and (1-4C)alkoxy; or together with the nitrogen atom and the group $R^{4b}$ or $R^{4c}$ to which they are attached, form a 4-6 membered azacycloalkylene group;

$A^3$ and $A^4$ are each independently selected from (3-6C)cycloalkyl, (6-10C)aryl, (2-9C)heteroaryl and (3-6C)heterocyclyl, wherein each cycloalkyl is unsubstituted or substituted with from 1 to 4 substituents selected independently from (1-4C)alkyl and each aryl, heteroaryl or heterocyclyl group is unsubstituted or substituted with from 1 to 4 substituents independently selected from halo, (1-4C)alkyl and (1-4C)alkoxy;

provided that the number of contiguous atoms in the shortest chain between the two nitrogen atoms to which $R^4$ is attached is in the range of from 4 to 16;

$R^5$ represents hydrogen or (1-4C)alkyl;

$R^6$ is —$NR^{6a}CR^{6b}$(O) or —$CR^{6c}R^{6d}OR^{6e}$ and $R^7$ is hydrogen; or $R^6$ and $R^7$ together form —$NR^{7a}$C(O)—$CR^{7b}$=$CR^{7c}$—, —$CR^{7d}$=$CR^{7e}$—C(O)—$NR^{7f}$—, —$NR^{7g}$C(O)—$CR^{7h}R^{7i}$—$CR^{7j}R^{7k}$— or —$CR^{7l}R^{7m}$—$CR^{7n}R^{7o}$—C(O)—$NR^{7p}$—;

each of $R^{6a}$, $R^{6b}$, $R^{6c}$, $R^{6d}$ and $R^{6e}$ is independently hydrogen or (1-4C)alkyl; and each of $R^{7a}$, $R^{7b}$, $R^{7c}$, $R^{7d}$, $R^{7e}$, $R^{7f}$, $R^{7g}$, $R^{7h}$, $R^{7i}$, $R^{7j}$, $R^{7k}$, $R^{7m}$, $R^{7n}$, $R^{7o}$ and $R^{7p}$ is independently hydrogen or (1-4C)alkyl;

or a pharmaceutically acceptable salt or solvate or stereoisomer thereof.

In another of its composition aspects, this invention is directed to a compound of formula II:

II

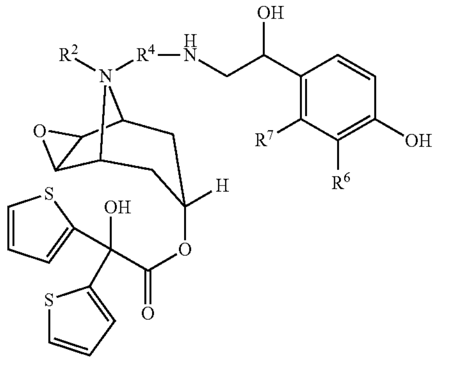

wherein $R^2$, $R^4$, $R^6$ and $R^7$ are as defined herein (including any specific or preferred embodiments);

or a pharmaceutically acceptable salt or solvate or stereoisomer thereof.

In another of its composition aspects, this invention is directed to a compound of formula III:

III

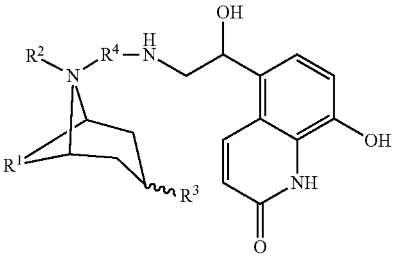

wherein $R^1$, $R^2$, $R^3$ and $R^4$ are as defined herein (including any specific or preferred embodiments);

or a pharmaceutically acceptable salt or solvate or stereoisomer thereof.

In yet another of its composition aspects, this invention is directed to a compound of formula IV:

IV

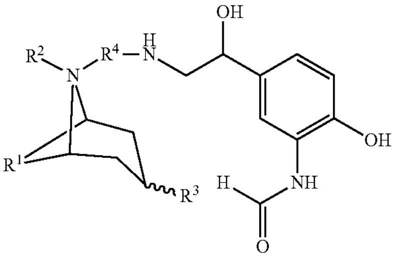

wherein $R^1$, $R^2$, $R^3$ and $R^4$ are as defined herein (including any specific or preferred embodiments);

or a pharmaceutically acceptable salt or solvate or stereoisomer thereof.

In still another of its composition aspects, this invention is directed to a compound of formula V:

V

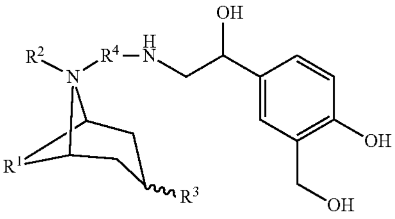

wherein $R^1$, $R^2$, $R^3$ and $R^4$ are as defined herein (including any specific or preferred embodiments);

or a pharmaceutically acceptable salt or solvate or stereoisomer thereof.

In another of its composition aspects, this invention is directed to a pharmaceutical composition comprising a pharmaceutically acceptable carrier and a therapeutically effective amount of a compound of formula I or a pharmaceutically acceptable salt or solvate or stereoisomer thereof. Such pharmaceutical compositions may optionally contain other therapeutic agents. Accordingly, in one embodiment, this invention is directed to such a pharmaceutical composition wherein the composition further comprises a therapeutically effective amount of a steroidal anti-inflammatory agent, such as a corticosteroid.

Compounds of this invention possess both $\beta_2$ adrenergic receptor agonist activity and muscarinic receptor antagonist activity. Accordingly, the compounds of formula I are useful for treating pulmonary disorders, such as asthma and chronic obstructive pulmonary disease.

Accordingly, in one of its method aspects, this invention is directed to a method for treating a pulmonary disorder, the method comprising administering to a patient in need of treatment a therapeutically effective amount of a compound of formula I or a pharmaceutically acceptable salt or solvate or stereoisomer thereof.

Additionally, in another of its method aspects, this invention is directed to a method of producing bronchodilation in a patient, the method comprising administering to a patient a bronchodilation-producing amount of a compound of formula I or a pharmaceutically acceptable salt or solvate or stereoisomer thereof.

This invention is also directed to a method of treating chronic obstructive pulmonary disease or asthma, the method comprising administering to a patient in need of treatment a therapeutically effective amount of a compound of formula I or a pharmaceutically acceptable salt or solvate or stereoisomer thereof.

Since compounds of this invention possess both $\beta_2$ adrenergic receptor agonist activity and muscarinic receptor antagonist activity, such compounds are also useful as research tools. Accordingly, in yet another of its method aspects, this invention is directed to a method for using a compound of formula I or a pharmaceutically acceptable salt or solvate or stereoisomer thereof as a research tool for studying a biological system or sample, or for discovering new chemical compounds having both $\beta_2$ adrenergic agonist activity and muscarinic receptor antagonist activity.

This invention is also directed to processes and novel intermediates useful for preparing compounds of formula I or a pharmaceutically acceptable salt or solvate or stereoisomer thereof. Accordingly, in another of its method aspects, this invention is directed to a process of preparing a compound of formula I, the process comprising:

(a) reacting a compound of formula 1 or a salt or protected derivative thereof; with a compound of formula 2;

(b) reacting a compound of formula 3 or a salt or a protected derivative thereof; with a compound of formula 4;

(c) coupling a compound of formula 5 or a salt or protected derivative thereof; with a compound of formula 6;

(d) for a compound of formula I wherein $R^5$ represents a hydrogen atom, reacting a compound of formula 3 or a salt or protected derivative thereof; with a compound of formula 7 or a hydrate thereof, in the presence of a reducing agent;

(e) reacting a compound of formula 1 or a salt or protected derivative thereof; with a compound of formula 8 or a hydrate thereof, in the presence of a reducing agent;

(f) reacting a compound of formula 9 or a salt or protected derivative thereof; with a compound of formula 10;

(g) reacting a compound of formula 11 or a salt or protected derivative thereof; with a reducing agent; or (h) reacting a compound of formula 12 or a salt or hydrate or protected derivative thereof, with a compound of formula 10 in the presence of a reducing agent;

and then removing any protecting groups to form a compound of formula I; wherein the compounds of formula 1-12 are as defined therein.

In one embodiment, the above process further comprises the step of forming a pharmaceutically acceptable salt of a compound of formula I. In other embodiments, this invention is directed to the other processes described herein; and to the product prepared by any of the processes described herein.

This invention is also directed to a compound of formula I or a pharmaceutically acceptable salt or solvate or stereoisomer thereof, for use in therapy or as a medicament.

Additionally, this invention is directed to the use of a compound of formula I or a pharmaceutically acceptable salt or solvate or stereoisomer thereof, for the manufacture of a medicament; especially for the manufacture of a medicament for the treatment of a pulmonary disorder.

DETAILED DESCRIPTION OF THE INVENTION

In one of its composition aspects, this invention is directed to novel compounds of formula I or pharmaceutically acceptable salts or solvates or stereoisomers thereof. These compounds contain one or more chiral centers and therefore, this invention is directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions of this invention unless otherwise indicated, provided that the utility of the composition as a whole is not eliminated by the presence of such other isomers.

In particular, compounds of formula I contain a chiral center at the carbon atom indicated by the symbol * in the following formula:

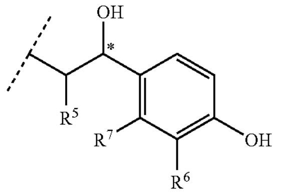

In one embodiment of this invention, the carbon atom identified by the symbol * has the (R) configuration. In this embodiment, it is preferred for compounds of formula I to have the (R) configuration at the carbon atom identified by the symbol * or to be enriched in a stereoisomeric form having the (R) configuration at this carbon atom. In another embodiment of this invention, the carbon atom identified by the symbol * has the (S) configuration. In this embodiment, it is preferred for compounds of formula I to have the (S) configuration at the carbon atom identified by the symbol * or to be enriched in a stereoisomeric form having the (S) configuration at this carbon atom. In some cases, in order to optimize the $\beta_2$ adrenergic agonist activity of the compounds of this invention, it is preferred that the carbon atom identified by the symbol * has the (R) configuration.

The compounds of formula I also contain several basic groups (e.g., amino groups) and therefore, the compounds of formula I can exist as the free base or in various salt forms. All such salt forms are included within the scope of this invention. Furthermore, solvates of compounds of formula I or salts thereof are included within the scope of this invention.

Additionally, where applicable, all cis-trans or E/Z isomers, endo/exo isomers, syn/anti isomers, other geometric isomers, tautomeric forms and topoisomeric forms of the compounds of formula I are included within the scope of this invention unless otherwise specified. For example, although the $R^2$ and $R^4$ groups to attached the nitrogen atom of the azabicycloalkane ring may be shown in a particular orientation relative to the azabicycloalkane ring, all isomers (syn/anti or exo/endo) are included within the scope of this invention. By way of further illustration, this invention is intended to cover the syn and anti isomers represented by formula Ia or Ib:

Ia

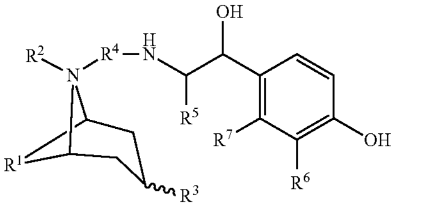

Ib

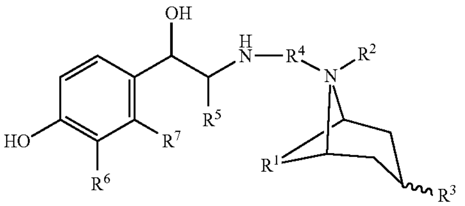

wherein $R^1$-$R^7$ are as defined herein.

The nomenclature used herein to name the compounds of this invention and intermediates thereof has generally been derived using the commercially-available AutoNom software (MDL, San Leandro, Calif.).

Additionally, those skilled in the art will recognize that the azabicycloalkane rings employed in this invention having an additional bridging ring, such as where $R^1$ is an oxiran-1,2-diyl group, are azatricycloalkane compounds.

Representative Embodiments

The following substituents and values are intended to provide representative examples of various aspects and embodiments of this invention. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

In one embodiment, $R^1$ represents $—CH_2CH_2—$. In another embodiment, $R^1$ represents —CH═CH—. In yet another embodiment, $R^1$ represents an oxiran-1,2-diyl group, i.e., a group of the formula:

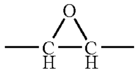

In one embodiment, $R^2$ is an electron pair. In this embodiment, the nitrogen atom can exist as a free base, i.e., unprotonated and uncharged, or the nitrogen can be protonated. When protonated, the nitrogen atom is positively charged and a pharmaceutically-acceptable anion will be present.

In another embodiment, $R^2$ is (1-6C)alkyl which is unsubstituted or substituted with a hydroxy group or from 1 to 3 fluoro substituents. When $R^2$ is an alkyl group, the nitrogen atom is positively charged and a pharmaceutically-acceptable anion will be present. Representative $R^2$ groups in this embodiment include, but are not limited to, methyl, ethyl, n-propyl, isopropyl, n-butyl, isobutyl, sec-butyl, tert-butyl, n-pentyl, n-hexyl, fluoromethyl, difluoromethyl, trifluoromethyl, hydroxymethyl, 2-fluoroethyl, 2,2-difluoroethyl, 2,2,2-trifluoroethyl, 2-hydroxyethyl, 2, hydroxypropyl, 3-hydroxypropyl and the like.

In one embodiment, $R^3$ represents $—OC(O)CR^{3a}R^{3b}R^{3c}$. In another embodiment, $R^3$ represents $—NHC(O)R^{3d}$.

In a particular embodiment, $R^{3a}$ represents hydroxy or hydroxy(1-4C)alkyl. Particular $R^{3a}$ groups include hydroxy and hydroxymethyl.

In a particular embodiment, $R^{3b}$ represents a phenyl group which is unsubstituted or substituted with from 1 to 4 substituents selected independently from halo, (1-4C)alkyl and (1-4C)alkoxy. Particular $R^{3b}$ groups in this embodiment include phenyl, 3-fluorophenyl, 4-fluorophenyl, 3-chlorophenyl, 4-chlorophenyl, 3-methylphenyl, 4-methylphenyl, 3-methoxyphenyl, 4-methoxyphenyl, 3-chloro-4-methoxyphenyl and the like.

In another particular embodiment, $R^{3b}$ represents a (3-6C) cycloalkyl group which is unsubstituted or substituted with from 1 to 4 substituents selected independently from halo, (1-4C)alkyl and (1-4C)alkoxy. Particular $R^{3b}$ groups in this embodiment include cyclopropyl, cyclobutyl, cyclopentyl, cyclohexyl and the like.

In still another particular embodiment, $R^{3b}$ represents a (3-5C)heteroaryl group which is unsubstituted or substituted with from 1 to 4 substituents selected independently from halo, (1-4C)alkyl and (1-4C)alkoxy and wherein the heteroaryl group contains 1 or 2 ring heteroatoms selected independently from oxygen, nitrogen and sulfur. Particular $R^{3b}$ groups in this embodiment include pyridyl, such as pyrid-2-yl, pyrid-3-yl or pyrid-4-yl; furyl, such as fur-2-yl and fur-3-yl; thienyl, such as thien-2-yl and thien-3-yl; a pyrrolyl, such as pyrrol-2-yl and pyrrol-3-yl; a thiazolyl, such as thiazol-2-yl, thiazol-4-yl and thiazol-5-yl; thiadiazolyle, such as 1,2,4-thiadiazol-5-yl; and the like.

In yet another particular embodiment, $R^{3b}$ represents a (3-5C)heterocyclyl group which is unsubstituted or substituted with from 1 to 4 substituents selected independently from halo, (1-4C)alkyl and (1-4C)alkoxy and wherein the heterocyclyl group contains 1 or 2 ring heteroatoms selected independently from oxygen, nitrogen and sulfur. Particular $R^{3b}$ groups in this embodiment include piperidinyl, such as piperidin-4-yl; and pyrrolidinyl, such as pyrrolidin-2-yl.

In a particular embodiment, $R^{3c}$ represents hydrogen.

In another particular embodiment, $R^{3c}$ represents a phenyl group which is unsubstituted or substituted with from 1 to 4 substituents selected independently from halo, (1-4C)alkyl and (1-4C)alkoxy. Particular $R^{3c}$ groups in this embodiment include phenyl, 3-fluorophenyl, 4-fluorophenyl, 3-chlorophenyl, 4-chlorophenyl, 3-methylphenyl, 4-methylphenyl, 3-methoxyphenyl, 4-methoxyphenyl, 3-chloro-4-methoxyphenyl and the like.

In another particular embodiment, $R^{3c}$ represents a (3-6C) cycloalkyl group which is unsubstituted or substituted with from 1 to 4 substituents selected independently from halo, (1-4C)alkyl and (1-4C)alkoxy. Particular $R^{3c}$ groups in this embodiment include cyclopropyl, cyclobutyl, cyclopentyl, cyclohexyl and the like.

In still another particular embodiment, $R^{3c}$ represents a (3-5C)heteroaryl group which is unsubstituted or substituted with from 1 to 4 substituents selected independently from halo, (1-4C)alkyl and (1-4C)alkoxy and wherein the heteroaryl group contains 1 or 2 ring heteroatoms selected independently from oxygen, nitrogen and sulfur. Particular $R^{3c}$ groups in this embodiment include pyridyl, such as pyrid-2-yl, pyrid-3-yl or pyrid-4-yl; furyl, such as fur-2-yl and fur-3-yl; thienyl, such as thien-2-yl and thien-3-yl; a pyrrolyl, such as pyrrol-2-yl and pyrrol-3-yl; a thiazolyl, such as thiazol-2-yl, thiazol-4-yl and thiazol-5-yl; thiadiazolyle, such as 1,2,4-thiadiazol-5-yl; and the like.

In yet another particular embodiment, $R^{3c}$ represents a (3-5C)heterocyclyl group which is unsubstituted or substituted with from 1 to 4 substituents selected independently from halo, (1-4C)alkyl and (1-4C)alkoxy and wherein the heterocyclyl group contains 1 or 2 ring heteroatoms selected independently from oxygen, nitrogen and sulfur. Particular $R^{3c}$ groups in this embodiment include piperidinyl, such as piperidin-4-yl; and pyrrolidinyl, such as pyrrolidin-2-yl.

In a particular embodiment, $R^{3a}$ is hydroxy; and $R^{3b}$ and $R^{3c}$ are both thien-2-yl.

In another particular embodiment, $R^{3a}$ is hydroxymethyl; and $R^{3b}$ is phenyl; and $R^{3c}$ is hydrogen.

In a particular embodiment, $R^{3d}$ is 1-methylindazol-3-yl.

In one embodiment of the compounds of formula I, $R^5$ is hydrogen or (1-4C)alkyl; such as hydrogen, methyl, ethyl, n-propyl, isopropyl, n-butyl, sec-butyl, isobutyl and tert-butyl. In another embodiment, each $R^5$ is independently hydrogen, methyl or ethyl. In a particular embodiment, $R^5$ is hydrogen.

In one embodiment of this invention, $R^6$ is —$NR^{6a}CR^{6b}$(O) and $R^7$ is hydrogen, where each of $R^{6a}$ and $R^{6b}$ is independently hydrogen or (1-4C)alkyl, such as hydrogen, methyl, ethyl, n-propyl, isopropyl, n-butyl, sec-butyl, isobutyl and tert-butyl. In one embodiment, these groups are independently hydrogen or (1-3C)alkyl. In another embodiment, these groups are independently hydrogen, methyl or ethyl. A particular value for $R^6$ in this embodiment is —NHCHO.

In another embodiment of this invention, $R^6$ is —$CR^{6c}R^{6d}OR^{6e}$ and $R^7$ is hydrogen, wherein each of $R^{6c}$, $R^{6d}$ and $R^{6e}$ is independently hydrogen or (1-4C)alkyl, such as hydrogen, methyl, ethyl, n-propyl, isopropyl, n-butyl, sec-butyl, isobutyl and tert-butyl. A particular value for $R^6$ in this embodiment is —$CH_2OH$.

In another embodiment, $R^6$ and $R^7$ together form —$NR^{7a}C$(O)—$CR^{7b}$=$CR^{7c}$—, —$CR^{7d}$=$CR^{7e}$—C(O)—$NR^{7f}$—, —$NR^{7g}C$(O)—$CR^{7h}R^{7i}$—$CR^{7j}R^{7k}$— or —$CR^{7l}R^{7m}$—$CR^{7n}R^{7o}$—C(O) —$NR^{7p}$—; where each of $R^{7a}$, $R^{7b}$, $R^{7c}$, $R^{7d}$, $R^{7e}$, $R^{7f}$, $R^{7g}$, $R^{7h}$, $R^{7i}$, $R^{7j}$, $R^{7k}$, $R^{7l}$, $R^{7m}$, $R^{7n}$, $R^{7o}$ and $R^{7p}$ is independently hydrogen or (1-4C)alkyl; such as hydrogen, methyl, ethyl, n-propyl, isopropyl, n-butyl, sec-butyl, isobutyl and tert-butyl. In one embodiment, these groups are independently hydrogen or (1-3C)alkyl. In another embodiment, these groups are independently hydrogen, methyl or ethyl. Particular values for $R^6$ and $R^7$ in this embodiment are $R^6$ and $R^7$ together form —NHC(O)—CH=CH—, —CH=CH—C(O)—NH—, —$CH_2$—$CH_2$—C(O)NH— or —NHC(O)—$CH_2$—$CH_2$—; including where $R^6$ and $R^7$ together form —NHC(O)—CH=CH— or —CH=CH—C(O)—NH—; and in particular, where $R^6$ and $R^7$ together form —NHC(O)—CH=CH— (i.e., the nitrogen atom is attached at $R^6$ and the carbon atom is attached at $R^7$ to form, together with the hydroxyphenyl ring to which $R^6$ and $R^7$ are attached, a 8-hydroxy-2-oxo-1,2-dihydroquinolin-5-yl group).

In the compounds of formula I, $R^4$ is a divalent group of the formula:

$$—(R^{4a})_d-(A^1)_e-(R^{4b})Q(R^{4c})_g-(A^2)_h-(R^{4d})_i—$$

wherein $R^{4a}$, $A^1$, $R^{4b}$, Q, $R^{4c}$, $A^2$, $R^{4d}$, d, e, f, g h and i are as defined herein. In the compound of this invention, the values of each of the components $R^{4a}$, $A^1$, $R^{4b}$, Q, $R^{4c}$, $A^2$ and $R^{4d}$ are selected such that the number of contiguous atoms in the shortest chain between the two nitrogen atoms to which $R^4$ is attached is in the range of from 4 to 16, (specifically, 4, 5, 6, 7, 8, 9, 10, 11, 12, 13, 14, 15 or 16); including 8, 9, 10, 11, 12, 13 or 14; such as 8, 9, 10 or 11; or 9 or 10. When selecting values for each variable in $R^4$, it will be appreciated by those skilled in the art that values should be selected such that a chemically stable group is formed.

When determining the number of contiguous atoms in the shortest chain between the two nitrogen atoms to which $R^4$ is attached, each contiguous atom of the chain is counted consecutively starting from the first atom in the $R^4$ group adjacent to the nitrogen of the azabicycloalkane ring ending with the last atom in the $R^4$ group adjacent to the nitrogen of the aminohydroxyethyl group. Where two or more chains are possible, the shortest chain is used to determine the number of contiguous atoms. As shown below, for example, when $R^4$ is —$(CH_2)_2$NHC(O)—$CH_2$— (phen-1,4-ylene)-$CH_2$—, there are 10 contiguous atoms in the shortest chain counted consecutively starting from the first atom in the $R^4$ group adjacent to the nitrogen of the azabicycloalkane ring ending with the last atom in the $R^4$ group adjacent to the nitrogen of the aminohydroxyethyl group as shown below:

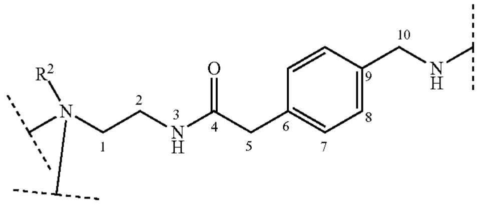

In one embodiment of $R^4$, $R^{4a}$ is selected from (1-10C) alkylene, (2-10C)alkenylene and (2-10C)alkynylene wherein the alkylene group is unsubstituted or substituted with 1 or 2 substituents independently selected from (1-4C)alkyl, hydroxy and phenyl. Representative examples of particular values for $R^{4a}$ are —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)CH(CH_3)$—, —$(CH_2)C(CH_3)_2$—, and —$(CH_2)_2C(phenyl)_2$-. In another aspect, $R^{4a}$ is —$(CH_2)C(=CH_2)$—.

In one embodiment, d is 1.

In one embodiment, $A^1$ is an optionally substituted (3-7C) cycloalkylene group; including a cyclohexylene group, such as cyclohex-1,4-ylene and cyclohex-1,3-ylene; and a cyclopentylene group, such as cyclopent-1,3-ylene.

In another embodiment, $A^1$ is an optionally substituted (6-10C)arylene group, including a phenylene group, such as phen-1,4-ylene, phen-1,3-ylene and phen-1,2-ylene; and a naphthylene group, such as naphth-1,4-ylene and napth-1,5-ylene.

In yet another embodiment, $A^1$ is an optionally substituted (2-9C)heteroarylene group, including a pyridylene group, such as pyrid-1,4-ylene; a furylene group, such as fur-2,5-ylene and fur-2,4-ylene; a thienylene group, such as thien-2,5-ylene and thien-2,4-ylene; and a pyrrolylene, such as pyrrol-2,5-ylene and pyrrol-2,4-ylene.

In still another embodiment, $A^1$ is an optionally substituted (3-6C)heterocyclene group, including a piperidinylene group, such as piperidin-1,4-ylene; and a pyrrolidinylene group, such as pyrrolidin-2,5-ylene.

In a particular embodiment, $A^1$ is an optionally substituted phenylene, thienylene, cyclopentylene, cyclohexylene or piperidinylene.

In one embodiment, e is 0.

In a particular embodiment, $R^{4b}$ is (1-5C)alkylene. Representative examples of particular values for $R^{4b}$ are —$CH_2$—, —$(CH_2)_2$—, —$(CH_2)_3$—, —$(CH_2)_4$—, —$(CH_2)_5$—; including methylene, ethylene and propylene.

In one embodiment, f is 0.

In a particular embodiment, Q is selected from a bond, —$N(Q^a)C(O)$—, —$C(O)N(Q^b)$-, —$N(Q^c)S(O)_2$—, —$S(O)_2N(Q^d)$-, —$N(Q^e)C(O)N(Q^f)$-, —$OC(O)N(Q^i)$-, —$N(Q^j)C(O)O$— or —$N(Q^k)$; such as where Q is a bond, —$N(Q^a)C(O)$— or —$C(O)N(Q^b)$-. Representative examples of particular values for Q are a bond, O, NH, —C(O)NH—, —$C(O)N(CH_3)$—, —NHC(O)—, —$N(CH_3)C(O)$—, —$S(O)_2NH$—, —$S(O)_2N(CH_3)$—, —$NHS(O)_2$—, —$N(CH_3)S(O)_2$— and —NHC(O)NH—. Another example of a value for Q, together with $R^{4c}$, is —C(O)(piperidin-1,4-ylene).

In one embodiment, $Q^a$, $Q^b$, $Q^c$, $Q^d$, $Q^e$, $Q^f$, $Q^g$, $Q^h$, $Q^i$, $Q^j$ and $Q^k$ are each independently selected from hydrogen and (1-6C)alkyl, wherein the alkyl group is unsubstituted or substituted with from 1 to 3 substituents independently selected from fluoro, hydroxy and (1-4C)alkoxy. For example, $Q^a$, $Q^b$, $Q^c$, $Q^d$, $Q^e$, $Q^f$, $Q^g$, $Q^h$, $Q^i$, $Q^j$ and $Q^k$ are each independently selected from hydrogen, and (1-3C)alkyl, including hydrogen, methyl, ethyl, n-propyl and isopropyl. An example of a value for each of $Q^a$, $Q^b$, $Q^c$, $Q^d$, $Q^e$, $Q^f$, $Q^g$, $Q^h$, $Q^i$, $Q^j$ and $Q^k$ is hydrogen.

In another embodiment, $Q^a$, $Q^b$, $Q^c$, $Q^d$, $Q^e$, $Q^f$, $Q^g$, $Q^h$, $Q^i$, $Q^j$ and $Q^k$ together with the nitrogen atom and the group $R^{4b}$ or $R^{4c}$ to which they are attached, form a 4-6 membered azacycloalkylene group. For example, $Q^a$ or $Q^b$ together with the nitrogen atom and the group $R^{4b}$ or $R^{4c}$ to which they are attached, form a piperidin-4-ylene group. By way of illustration, when Q represents —$N(Q^a)C(O)$— and $Q^a$ together with the nitrogen atom and the group $R^{4b}$ to which it is attached, forms a piperidin-4-ylene group, $R^4$ is a group of formula:

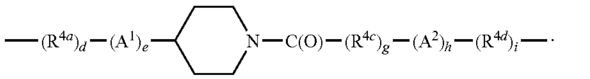

Similarly, when Q represents —$C(O)N(Q^b)$- and $Q^b$ together with the nitrogen atom and the group $R^{4c}$ to which it is attached, forms a piperidin-4-ylene group, $R^4$ is a group of formula:

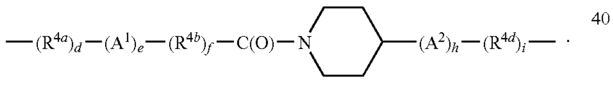

In a particular embodiment, $R^{4c}$ is (1-5C)alkylene. Representative examples of particular values for $R^{4c}$ are —$CH_2$—, —$(CH_2)_2$—, —$(CH_2)_3$—, —$(CH_2)_4$—, —$(CH_2)_5$—; including methylene, ethylene and propylene.

In one embodiment, $A^2$ is an optionally substituted (3-7C) cycloalkylene group; including a cyclohexylene group, such as cyclohex-1,4-ylene and cyclohex-1,3-ylene; and a cyclopentylene group, such as cyclopent-1,3-ylene.

In another embodiment, $A^2$ is an optionally substituted (6-10C)arylene group, including a phenylene group, such as phen-1,4-ylene, phen-1,3-ylene and phen-1,2-ylene; and a naphthylene group, such as naphth-1,4-ylene and napth-1,5-ylene.

In yet another embodiment, $A^2$ is an optionally substituted (2-9C)heteroarylene group, including a pyridylene group, such as pyrid-1,4-ylene; a furylene group, such as fur-2,5-ylene and fur-2,4-ylene; a thienylene group, such as thien-2,5-ylene and thien-2,4-ylene; and a pyrrolylene, such as pyrrol-2,5-ylene and pyrrol-2,4-ylene.

In still another embodiment, $A^2$ is an optionally substituted (3-6C)heterocyclene group, including a piperidinylene group, such as piperidin-1,4-ylene; and a pyrrolidinylene group, such as pyrrolidin-2,5-ylene.

In a particular embodiment, $A^2$ is optionally substituted phenylene, thienylene, cyclopentylene, cyclohexylene or piperidinylene.

By way of illustration, either $A^1$ or $A^2$ or both can be phenylene, such as phen-1,4-ylene or phen-1,3-ylene, where the phenylene group is unsubstituted or substituted with from 1 to 4 substituents independently selected from halo, (1-4C) alkyl, (1-4C)alkoxy, —S-(1-4C)alkyl, —S(O)-(1-4C)alkyl, —$S(O)_2$—(1-4C)alkyl, —C(O)O(1-4C)alkyl, carboxy, cyano, hydroxy, nitro, trifluoromethyl and trifluoromethoxy. Representative examples include phen-1,3-ylene, phen-1,4-ylene, 4-chlorophen-1,3-ylene, 6-chlorophen-1,3-ylene, 4-methylphen-1,3-ylene, 2-fluorophen-1,4-ylene, 2-chlorophen-1,4-ylene, 2-bromophen-1,4-ylene, 2-iodophen-1,4-ylene, 2-methylphen-1,4-ylene, 2-methoxyphen-1,4-ylene, 2-trifluoromethoxyphen-1,4-ylene, 3-nitrophen-1,4-ylene, 3-chlorophen-1,4-ylene, 2,5-difluorophen-1,4-ylene, 2,6-dichlorophen-1,4-ylene, 2,6-diiodophen-1,4-ylene, 2-chloro-6-methylphen-1,4-ylene, 2-chloro-5-methoxyphen-1,4-ylene, 2,3,5,6-tetrafluorophen-1,4-ylene.

Alternatively, $A^1$ or $A^2$ or both can be cyclopentylene or cyclohexylene; wherein the cyclopentylene or cyclohexylene group is unsubstituted or substituted with (1-4C)alkyl. Representative examples include cis-cyclopent-1,3-ylene, trans-cyclopent-1,3-ylene, cis-cyclohex-1,4-ylene and trans-cyclohex-1,4-ylene. $A^1$ or $A^2$ or both can also be optionally substituted thienylene or piperidinylene, for example, thien-2,5-ylene or piperidin-1,4-ylene.

In one embodiment, $R^{4d}$ is selected from (1-10C)alkylene, (2-10C)alkenylene and (2-10C)alkynylene wherein the alkylene is unsubstituted or substituted with 1 or 2 substituents independently selected from (1-4C)alkyl, hydroxy and phenyl. Representative examples of particular values for $R^{4d}$ are —$(CH_2)$—, —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$— and —$(CH_2)CH(CH_3)$—$(CH_2)$—$C(CH_3)_2$—$(CH_2)_2$—. In another embodiment, $R^{4d}$ represents (1-6C)alkylene-NHC(O)-(1-6C)alkylene. Particular values for $R^{4d}$ in this embodiment are —$CH_2NHC(O)CH_2$— and —$CH_2CH_2NHC(O)CH_2$—.

In a particular embodiment, $R^4$ is a divalent group of the formula: —$(R^{4a})_d$— where $R^{4a}$ is (4-10C)alkylene. In one aspect of this embodiment, $R^4$ is a divalent group of the formula: —$(CH_2)_j$— where j is 8, 9 or 10. Examples of particular values for $R^4$ in this embodiment are —$(CH_2)_4$—, —$(CH_2)_5$—, —$(CH_2)_6$—, —$(CH_2)_7$—, —$(CH_2)_8$—, —$(CH_2)_9$, and —$(CH_2)_{10}$—; including —$(CH_2)_8$—, —$(CH_2)_9$, and —$(CH_2)_{10}$—.

In another particular embodiment, $R^4$ is a divalent group of the formula:

$$—(R^{4a})_d\text{-}(A^2)_h\text{-}(R^{4d})_i—$$

where $R^{4a}$ is (1-10C)alkylene, such as —$(CH_2)$—, —$(CH_2)_2$—, —$(CH_2)_3$—; $A^2$ is (6-10C)arylene, such as phen-1,4-ylene or phen-1,3-ylene, or (2-9C)heteroarylene, such as thien-2,5-ylene or thien-2,4-ylene; and $R^{4d}$ is (1-10C) alkylene, such as —$(CH_2)$—, —$(CH_2)_2$—, —$(CH_2)_3$—. Examples of particular values for $R^4$ in this embodiment are —$(CH_2)$-(phen-1,4-ylene)-$(CH_2)$—; —$(CH_2)$-(phen-1,4-ylene)-$(CH_2)_2$—; —$(CH_2)$-(phen-1,4-ylene)-$(CH_2)_3$—; —$(CH_2)_2$-(phen-1,4-ylene)-$(CH_2)$—; —$(CH_2)_2$-(phen-1,4-ylene)-$(CH_2)_2$—; —$(CH_2)_2$-(phen-1,4-ylene)-$(CH_2)_3$—; —$(CH_2)_3$-(phen-1,4-ylene)-$(CH_2)$—; —$(CH_2)_3$-(phen-1,4-ylene)-$(CH_2)_2$—, —$(CH_2)_3$-(phen-1,4-ylene)-$(CH_2)_3$—, —$(CH_2)_4$-(phen-1,4-ylene)-$(CH_2)$—; —$(CH_2)_4$-(phen-1,4-ylene)-$(CH_2)_2$— and —$(CH_2)_4$-(phen-1,4-ylene)-$(CH_2)_3$—.

In yet another particular embodiment, $R^4$ is a divalent group of the formula:

$$—(R^{4a})_d\text{-Q-}(A^2)_h\text{-}(R^{4d})_i—$$

where Q is —O— or —N($Q^k$)-; $Q^k$ is hydrogen or (1-3C) alkyl, such as methyl or ethyl; $R^{4a}$ is (1-10C)alkylene, such as —($CH_2$)—, —$(CH_2)_2$—, —$(CH_2)_3$—; $A^2$ is (6-10C)arylene, such as phen-1,4-ylene or phen-1,3-ylene, or (2-9C)heteroarylene, such as thien-2,5-ylene or thien-2,4-ylene; and $R^{4d}$ is (1-10C)alkylene, such as —($CH_2$)—, —$(CH_2)_2$—, —$(CH_2)_3$—. Examples of particular values for $R^4$ in this embodiment are —$(CH_2)_2$—O-(phen-1,4-ylene)-($CH_2$)—; —$(CH_2)_2$—O-(phen-1,4-ylene)-$(CH_2)_2$—; —$(CH_2)_2$—O-(phen-1,4-ylene)-$(CH_2)_3$—; —$(CH_2)_3$—O-(phen-1,4-ylene)-($CH_2$)—; —$(CH_2)_3$—O-(phen-1,4-ylene)-$(CH_2)_2$—; —$(CH_2)_3$—O-(phen-1,4-ylene)-$(CH_2)_3$—; —$(CH_2)_2$—NH-(phen-1,4-ylene)-($CH_2$)—; —$(CH_2)_2$—NH-(phen-1,4-ylene)-$(CH_2)_2$—; —$(CH_2)_2$—NH-(phen-1,4-ylene)-$(CH_2)_3$—; —$(CH_2)_3$—NH-(phen-1,4-ylene)-($CH_2$)—; —$(CH_2)_3$—NH-(phen-1,4-ylene)-$(CH_2)_2$— and —$(CH_2)_3$—NH-(phen-1,4-ylene)-$(CH_2)_3$—.

In yet another particular embodiment, $R^4$ is a divalent group of the formula:

$$—(R^{4a})_d\text{-}(A^1)_e\text{-}(R^{4b})_f\text{-Q-}(R^{4c})_g\text{-}(A^2)_h\text{-}(R^{4d})_i—$$

where Q is —N($Q^a$)C(O)— or —C(O)N($Q^b$)-. A particular value for $R^4$ in this embodiment is the formula:

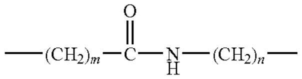

where m is an integer from 2 to 10; and n is an integer from 2 to 10; provided that m+n is an integer from 4 to 12. In this formula for $R^4$, d and g are 1 and e, f, h and i are 0; and $R^{4a}$ is —$(CH_2)_m$—, $R^{4c}$ is —$(CH_2)_n$— and Q is —C(O)NH—. Particular values for m are 2 or 3; and for n, 4, 5 or 6.

Another particular value for $R^4$ is the formula:

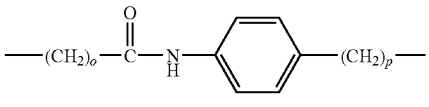

where o is an integer from 2 to 7; and p is an integer from 1 to 6; provided that o+p is an integer from 3 to 8. In this formula for $R^4$, d, h and i are 1 and e, f and g are 0; and $R^{4a}$ is —$(CH_2)_o$—, $A^2$ is phen-1,4-ylene, $R^{4d}$ is —$(CH_2)_p$— and Q is —C(O)NH—. Particular values for o are 2 or 3; and for p, 1 or 2. In this embodiment, the phen-1,4-ylene group may be optionally substituted as defined herein for $A^2$.

Another particular value for $R^4$ is the formula:

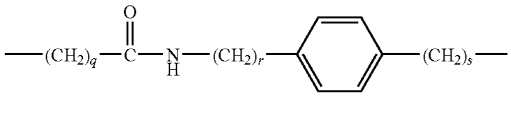

where q is an integer from 2 to 6; r is an integer from 1 to 5; and s is an integer from 1 to 5; provided that q+r+s is an integer from 4 to 8. In this formula for $R^4$, d, g, h and i are 1 and e and f are 0; and $R^{4a}$ is —$(CH_2)_q$, $R^{4c}$ is —$(CH_2)_r$—, $A^2$ is 1,4-phenylene, $R^{4d}$ is —$(CH_2)_s$— and Q is —C(O)NH—. Particular values for q are 2 or 3; for r, 1 or 2; and for s, 1 or 2. In this embodiment, the phen-1,4-ylene group may be optionally substituted as defined herein for $A^2$.

Another particular value for $R^4$ is the formula:

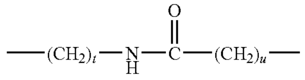

where t is an integer from 2 to 10; and u is an integer from 2 to 10; provided that t+u is an integer from 4 to 12. In this formula for $R^4$, d and g are 1 and e, f, h and i are 0; and $R^{4a}$ is —$(CH_2)_t$—, $R^{4c}$ is —$(CH_2)_u$— and Q is —NHC(O)—. Particular values for t are 2 or 3; and for u, 4, 5 or 6.

Another particular value for $R^4$ is the formula:

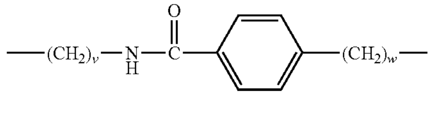

where v is an integer from 2 to 7; and w is an integer from 1 to 6; provided that v+w is an integer from 3 to 8. In this formula for $R^4$, d, h and i are 1 and e, f and g are 0; and $R^{4a}$ is —$(CH_2)_v$—, $A^2$ is 1,4-phenylene, $R^{4d}$ is —$(CH_2)_w$— and Q is —NHC(O)—. Particular values for v are 2 or 3; and for w, 1 or 2. In this embodiment, the phen-1,4-ylene group may be optionally substituted as defined herein for $A^2$.

Another particular value for $R^4$ is the formula:

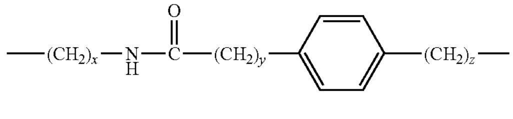

where x is an integer from 2 to 6; y is an integer from 1 to 5; and z is an integer from 1 to 5; provided that x+y+z is an integer from 4 to 8. In this formula for $R^4$, d, g, h and i are 1 and e and f are 0; and $R^{4a}$ is —$(CH_2)_x$—, $R^{4c}$ is —$(CH_2)_y$—, $A^2$ is 1,4-phenylene, $R^{4d}$ is —$(CH_2)_z$— and Q is —NHC(O)—. Particular values for x are 2 or 3; for y, 1 or 2; and for z, 1 or 2. In this embodiment, the phen-1,4-ylene group may be optionally substituted as defined herein for $A^2$.

By way of further illustration, $R^4$ can be selected from:

—$(CH_2)_7$—;
—$(CH_2)_8$—;
—$(CH_2)_9$—;
—$(CH_2)_{10}$—;
—$(CH_2)_{11}$—;
—$(CH_2)_2$C(O)NH$(CH_2)_5$—;
—$(CH_2)_2$N($CH_3$)C(O)—$(CH_2)_5$—;
—$(CH_2)_2$C(O)NH(phen-1,4-ylene)$CH_2$—;
—$(CH_2)_2$NHC(O)(phen-1,4-ylene)$CH_2$—;
—$(CH_2)_2$NHC(O)NH$(CH_2)_5$—;
—$(CH_2)_3$NHC(O)NH$(CH_2)_5$—;
—$(CH_2)_2$C(O)NH$CH_2$(cyclohex-1,3-ylene)$CH_2$—;
—$(CH_2)_2$NHC(O)(cyclopent-1,3-ylene)-;
—$(CH_2)_2$NHC(O)NH(phen-1,4-ylene)-$(CH_2)_2$—;
1-[—$(CH_2)_2$C(O)](piperidin-4-yl)-$(CH_2)_2$—;
—$(CH_2)_2$NHC(O)(trans-cyclohex-1,4-ylene)$CH_2$—;
—$(CH_2)_2$NHC(O)(cis-cyclopent-1,3-ylene)-;
—$(CH_2)_2$NH(phen-1,4-ylene)$(CH_2)_2$—;
1-[—$(CH_2)_2$NHC(O)](piperidin-4-yl)-$(CH_2)_2$—;
—$CH_2$(phen-1,4-ylene)NH(phen-1,4-ylene)$CH_2$—;
—$(CH_2)_2$C(O)NH$CH_2$(phen-1,3-ylene)$CH_2$—;
—$(CH_2)_2$C(O)NH$CH_2$(pyrid-2,6-ylene)$CH_2$—;
—$(CH_2)_2$C(O)NH(cis-cyclohex-1,4-ylene)$CH_2$—;
—$(CH_2)_2$C(O)NH(trans-cyclohex-1,4-ylene)$CH_2$—;
—$(CH_2)_2$NHC(O)(cis-cyclopent-1,3-ylene)$CH_2$—;
—$(CH_2)_2$N($CH_3$)C(O)(phen-1,3-ylene)$CH_2$—;
—$(CH_2)_2$N($CH_3$)C(O)(trans-cyclohex-1,4-ylene)$CH_2$—;

—(CH$_2$)$_2$C(O)NH(phen-1,4-ylene)CH$_2$—;
—(CH$_2$)$_2$C(O)NH(phen-1,4-ylene)C*H(CH$_3$)— ((S)-isomer);
—(CH$_2$)$_2$C(O)NH(phen-1,4-ylene)C*H(CH$_3$)— ((R)-isomer);
2-[(S)-(—CH$_2$—](pyrrolidin-1-yl)C(O)—(CH$_2$)$_4$—;
2-[(S)-(—CH$_2$—](pyrrolidin-1-yl)C(O)(phen-1,4-ylene)CH$_2$—;
—(CH$_2$)$_2$C(O)NH(4-chlorophen-1,3-ylene)CH$_2$—;
—CH$_2$(2-fluorophen-1,3-ylene)CH$_2$—;
—(CH$_2$)$_2$C(O)NH(4-methylphen-1,3-ylene)CH$_2$—;
—(CH$_2$)$_2$C(O)NH(6-chlorophen-1,3-ylene)CH$_2$—;
—(CH$_2$)$_2$C(O)NH(2-chlorophen-1,4-ylene)CH$_2$—;
—(CH$_2$)$_2$C(O)NH(2,6-dichlorophen-1,4-ylene)CH$_2$—;
—(CH$_2$)$_2$NHC(O)NHCH$_2$(phen-1,3-ylene)CH$_2$—;
4-[-CH$_2$—](piperidin-1-yl)C(O)(phen-1,4-ylene)CH$_2$—;
—(CH$_2$)$_2$C(O)N(CH$_2$CH$_3$)(phen-1,4-ylene)CH$_2$—;
1-[-(CH$_2$)$_2$NHC(O)](piperidin-4-yl)-;
—(CH$_2$)$_2$C(O)NH(phen-1,4-ylene)-(CH$_2$)$_2$—;
—(CH$_2$)$_2$NHC(O)(thien-2,5-ylene)CH$_2$—;
—(CH$_2$)$_2$N(CH$_3$)C(O)(3-nitrophen-1,4-ylene)CH$_2$—;
—(CH$_2$)$_2$N(CH$_3$)C(O)(trans-cyclohex-1,4-ylene)-;
1-[-CH$_2$(2-fluorophen-1,3-ylene)CH$_2$](piperidin-4-yl)-;
5-[—(CH$_2$)$_2$NHC(O)](pyrid-2-yl)CH$_2$—;
—(CH$_2$)$_2$(phen-1,4-ylene)-(CH$_2$)$_2$—;
—(CH$_2$)$_3$(thien-2,5-ylene)-(CH$_2$)$_3$—;
—(CH$_2$)$_2$(phen-1,4-ylene)NH(phen-1,4-ylene)-(CH$_2$)$_2$—;
—CH$_2$(phen-1,2-ylene)NH(phen-1,4-ylene)-(CH$_2$)$_2$—;
1-[-CH$_2$(2-fluorophen-1,3-ylene)CH$_2$](piperidin-4-yl)-(CH$_2$)$_2$—;
1-[-CH$_2$(2-fluorophen-1,3-ylene)CH$_2$](piperidin-4-yl)CH$_2$—;
—(CH$_2$)$_2$C(O)NH(3-chlorophen-1,4-ylene)CH$_2$—;
—(CH$_2$)$_2$C(O)NH(2-(CF$_3$O—)phen-1,4-ylene)CH$_2$—;
—(CH$_2$)$_3$(phen-1,3-ylene)NH(phen-1,4-ylene)-(CH$_2$)$_2$—;
—(CH$_2$)$_2$S(O)$_2$NH(CH$_2$)$_5$—;
—CH$_2$(phen-1,3-ylene)NH(phen-1,4-ylene)-(CH$_2$)$_2$—;
—(CH$_2$)$_2$C(O)NH(2-iodophen-1,4-ylene)CH$_2$—;
—(CH$_2$)$_2$C(O)NH(2-chloro-5-methoxyphen-1,4-ylene)CH$_2$—;
—(CH$_2$)$_2$C(O)NH(2-chloro-6-methylphen-1,4-ylene)CH$_2$—;
—(CH$_2$)$_2$C(O)NH(CH$_2$)$_5$—;
—(CH$_2$)$_2$N(CH$_3$)S(O)$_2$(phen-1,4-ylene)CH$_2$—;
—(CH$_2$)$_2$C(O)NH(2-bromophen-1,4-ylene)CH$_2$—;
—(CH$_2$)$_3$(phen-1,4-ylene)NH(phen-1,4-ylene)-(CH$_2$)$_2$—;
—(CH$_2$)$_3$(phen-1,2-ylene)NH(phen-1,4-ylene)-(CH$_2$)$_2$—;
1-[-CH$_2$(2-fluorophen-1,3-ylene)CH$_2$](piperidin-4-yl)-(CH$_2$)$_3$—;
—(CH$_2$)$_2$C(O)NH(2-methoxyphen-1,4-ylene)CH$_2$—;
—(CH$_2$)$_5$NH(phen-1,4-ylene)-(CH$_2$)$_2$—;
4-[—(CH$_2$)$_2$-](piperidin-1-yl)(phen-1,4-ylene)-(CH$_2$)$_2$—;
—(CH$_2$)$_2$C(O)NH(phen-1,4-ylene)CH(CH$_3$)CH$_2$—;
—(CH$_2$)$_2$-(trans-cyclohex-1,4-ylene)NH(phen-1,4-ylene)-(CH$_2$)$_2$—;
—(CH$_2$)$_2$C(O)NH(2-fluorophen-1,4-ylene)CH$_2$—;
—(CH$_2$)$_2$(phen-1,3-ylene)NH(phen-1,4-ylene)-(CH$_2$)$_2$—;
—(CH$_2$)$_2$C(O)NH(2,5-difluorophen-1,4-ylene)CH$_2$—;
—(CH$_2$)$_2$NHC(O)(phen-1,4-ylene)-(CH$_2$)$_2$—;
1-[-CH$_2$(pyrid-2,6-ylene)CH$_2$](piperidin-4-yl)CH$_2$—;
—(CH$_2$)$_3$NH(phen-1,4-ylene)-(CH$_2$)$_2$—;
—(CH$_2$)$_2$NH(naphth-1,4-ylene)-(CH$_2$)$_2$—;
—(CH$_2$)$_3$O(phen-1,4-ylene)CH$_2$—;
1-[—(CH$_2$)$_3$](piperidin-4-yl)CH$_2$—;
4-[—(CH$_2$)$_2$](piperidin-1-yl)C(O)(phen-1,4-ylene)CH$_2$—;
—(CH$_2$)$_3$(phen-1,4-ylene)NHC(O)—(CH$_2$)$_2$—;
—(CH$_2$)$_3$O(phen-1,4-ylene)-(CH$_2$)$_2$—;
2-[—(CH$_2$)$_2$](benzimidazol-5-yl)CH$_2$—;
—(CH$_2$)$_2$-(trans-cyclohex-1,4-ylene)NHC(O)—(CH$_2$)$_2$—;
—(CH$_2$)$_2$-(trans-cyclohex-1,4-ylene)NHC(O)—(CH$_2$)$_4$—;
—(CH$_2$)$_2$-(trans-cyclohex-1,4-ylene)NHC(O)—(CH$_2$)$_5$—;
4-[—(CH$_2$)$_2$](piperidin-1-yl)C(O)—(CH$_2$)$_2$—;
—(CH$_2$)$_2$NHC(O)NH(phen-1,4-ylene)CH$_2$—;
—(CH$_2$)$_2$N(CH$_3$)—(CH$_2$)$_2$(cis-cyclohex-1,4-ylene)-;
—(CH$_2$)$_2$C(O)NH(2,3,5,6-tetrafluorophen-1,4-ylene)CH$_2$—;
—(CH$_2$)$_2$C(O)NH(2,6-diiodophen-1,4-ylene)CH$_2$—;
4-[—(CH$_2$)$_2$](piperidin-1-yl)C(O)—(CH$_2$)$_3$—;
4-[—(CH$_2$)$_2$](piperidin-1-yl)C(O)—(CH$_2$)$_4$—;
4-[-(CH$_2$)$_2$](piperidin-1-yl)C(O)—(CH$_2$)$_5$—;
—(CH$_2$)$_2$C(O)NHCH$_2$(phen-1,4-ylene)CH$_2$—;
—(CH$_2$)$_2$NHC(O)NHCH$_2$(phen-1,4-ylene)CH$_2$—;
—(CH$_2$)$_2$C(O)NH(2-methylphen-1,4-ylene)CH$_2$—;
1-[-(CH$_2$)$_3$O(phen-1,4-ylene)-(CH$_2$)$_2$](piperidin-4-yl)CH$_2$—;
—(CH$_2$)$_2$C(O)NHCH$_2$(phen-1,3-ylene)-(CH$_2$)$_2$—;
—(CH$_2$)$_2$O(phen-1,3-ylene)CH$_2$—;
—(CH$_2$)$_2$N(CH$_3$)C(O)CH$_2$O(phen-1,4-ylene)CH$_2$—;
—(CH$_2$)$_2$N(CH$_3$)C(O)CH$_2$O(phen-1,3-ylene)CH$_2$—;
—(CH$_2$)$_2$N(CH$_3$)C(O)(fur-2,5-ylene)CH$_2$—;
—(CH$_2$)$_2$N(CH$_3$)C(O)(thien-2,5-ylene)CH$_2$—;
—(CH$_2$)$_2$O(phen-1,4-ylene)O(CH$_2$)$_2$—;
—(CH$_2$)$_2$(trans-cyclohex-1,4-ylene)NHC(O)(phen-1,4-ylene)CH$_2$—;
—(CH$_2$)$_2$(trans-cyclohex-1,4-ylene)NHC(O)CH$_2$O(phen-1,2-ylene)CH$_2$—;
—(CH$_2$)$_2$(trans-cyclohex-1,4-ylene)NHC(O)CH$_2$O(phen-1,3-ylene)CH$_2$—;
—(CH$_2$)$_2$(trans-cyclohex-1,4-ylene)NHC(O)CH$_2$O(phen-1,4-ylene)CH$_2$—;
—(CH$_2$)$_2$(trans-cyclohex-1,4-ylene)NHC(O)(fur-2,5-ylene)CH$_2$—;
—(CH$_2$)$_2$(trans-cyclohex-1,4-ylene)NHC(O)(thien-2,5-ylene)CH$_2$—;
4-[-(CH$_2$)$_2$](piperidin-1-yl)C(O)CH$_2$O(phen-1,2-ylene)CH$_2$—;
4-[—(CH$_2$)$_2$](piperidin-1-yl)C(O)CH$_2$O(phen-1,3-ylene)CH$_2$—;
4-[—(CH$_2$)$_2$](piperidin-1-yl)C(O)CH$_2$O(phen-1,4-ylene)CH$_2$—;
4-[-(CH$_2$)$_2$](piperidin-1-yl)C(O)(fur-2,5-ylene)CH$_2$—;
4-[—(CH$_2$)$_2$](piperidin-1-yl)C(O)(thien-2,5-ylene)CH$_2$—;
—(CH$_2$)$_2$(phen-1,4-ylene)NHC(O)(phen-1,3-ylene)CH$_2$—;
—(CH$_2$)$_2$(phen-1,4-ylene)NHC(O)(phen-1,4-ylene)CH$_2$—;
—(CH$_2$)$_2$(phen-1,4-ylene)NHC(O)CH$_2$O(phen-1,2-ylene)CH$_2$—;
—(CH$_2$)$_2$(phen-1,4-ylene)NHC(O)CH$_2$O(phen-1,3-ylene)CH$_2$—;
—(CH$_2$)$_2$(phen-1,4-ylene)NHC(O)CH$_2$O(phen-1,4-ylene)CH$_2$—;
—(CH$_2$)$_2$(phen-1,4-ylene)NHC(O)(fur-2,5-ylene)CH$_2$—;
—(CH$_2$)$_2$(phen-1,4-ylene)NHC(O)(thien-2,5-ylene)CH$_2$—;
—(CH$_2$)$_2$(trans-cyclohex-1,4-ylene)NHC(O)(phen-1,3-ylene)CH$_2$—;
—(CH$_2$)$_3$O(phen-1,3-ylene)CH$_2$—;
—CH$_2$CH(OH)CH$_2$NH(phen-1,4-ylene)-(CH$_2$)$_2$—;
—(CH$_2$)$_4$NH(phen-1,4-ylene)-(CH$_2$)$_2$—;
—(CH$_2$)$_2$C(O)NH(phen-1,4-ylene)CH$_2$NHC(O)CH$_2$—;
—(CH$_2$)$_2$C(O)NH(phen-1,4-ylene)-(CH$_2$)$_2$NHC(O)CH$_2$—;
—(CH$_2$)$_2$C(O)NHCH$_2$(trans-cyclohex-1,4-ylene)CH$_2$—;
—(CH$_2$)$_2$NHC(O)—(CH$_2$)$_s$—;
—(CH$_2$)$_2$O(phen-1,3-ylene)O(CH$_2$)$_2$—;
—(CH$_2$)$_2$O(phen-1,2-ylene)O(CH$_2$)$_2$—;
—CH$_2$(phen-1,2-ylene)O(phen-1,2-ylene)CH$_2$—;

$—(CH_2)_2C(O)NH(CH_2)_6—$;
$—(CH_2)_3$(phen-1,4-ylene)-$(CH_2)_3—$;
$—(CH_2)_3$(phen-1,4-ylene)-$(CH_2)_2—$;
$—(CH_2)_4$(phen-1,4-ylene)-$(CH_2)_2—$;
$—(CH_2)_3$(furan-2,5-ylene)-$(CH_2)_3—$;
$—(CH_2)_2N(CH_3)C(O)NH$(phen-1,4-ylene)-$(CH_2)_2—$;
4-[$—(CH_2)_2$](piperidin-1-yl)C(O)NH(phen-1,4-ylene)-$(CH_2)_2—$;
$—(CH_2)_3$(phen-1,3-ylene)-$(CH_2)_3—$;
$—(CH_2)_3$(tetrahydrofuran-2,5-ylene)-$(CH_2)_3—$; and
$—(CH_2)_2O$(phen-1,4-ylene)$C(O)(CH_2)_2—$.

Representative Subgeneric Groupings

The following subgeneric formulae and groupings are intended to provide representative examples of various aspects and embodiments of this invention and as such, they are not intended to exclude other embodiments or to limit the scope of this invention unless otherwise indicated.

A particular group of compounds of formula I are those disclosed in U.S. Provisional Application No. 60/473,761, filed on May 28, 2003. This group includes compounds of formula Ic:

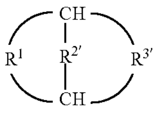

Ic in which:

$R^1$ represents $—CH_2CH_2—$, $—CH=CH—$, $—CH_2CH_2CH_2—$, $—CH_2CH(OCH_3)—$ or

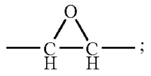

;

$R^{3'}$ represents $—CH_2CH(R^3)CH_2—$;

$R^3$ represents $—OC(O)CR^{3a}R^{3b}R^{3c}$ or $—NHC(O)R^{3d}$;

$R^{3a}$ represents hydrogen, hydroxy, (1-4C)alkyl or hydroxy (1-4C)alkyl;

$R^{3b}$ represents a (5-6C)cycloalkyl group that is unsubstituted or substituted by methyl, or a phenyl or thienyl group that is unsubstituted or substituted by one or two substituents selected independently from a halogen atom, a (1-4C)alkyl group and a (1-4C)alkoxy group, and $R^{3c}$ represents a hydrogen atom or a phenyl or thienyl group that is unsubstituted or substituted by one or two substituents selected independently from a halogen atom, a (1-4C)alkyl group and a (1-4C)alkoxy group;

or $R^{3b}$ and $R^{3c}$ together with $R^{3a}$ and the carbon atom to which they are attached form a group of formula:

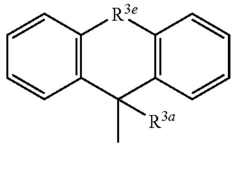

in which $R^{3e}$ represents O, S or $CH_2$;

$R^{3d}$ represents an indazol-3-yl group, which may bear a (1-4C)alkyl group at the 1-position;

$R^{2'}$ represents $—NR^{2a}—$ or $—N^+R^{2b}R^{2c}—X^-$;

$R^{2c}$ represents (1-6C)alkyl, which may bear a hydroxy substituent or from one to three fluoro substituents;

$X^-$ represents a pharmaceutically-acceptable anion;

each of $R^{2a}$ and $R^{2b}$ independently represents a group of formula

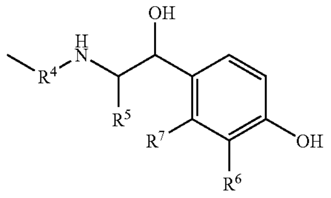

wherein:

$R^4$ is a divalent group of the formula:

$$—(R^{4a})_d-(A^1)_e-(R^{4b})_f-Q-(R^{4c})_g-(A^2)_h-(R^{4d})_i—$$

wherein d, e, f, g, h and i are each independently selected from 0 and 1;

$R^{4a}$, $R^{4b}$, $R^{4c}$ and $R^{4d}$ are each independently selected from the group consisting of (1-10C)alkylene, (2-10C)alkenylene and (2-10C)alkynylene wherein each alkylene, alkenylene or alkynylene group is unsubstituted or substituted with from 1 to 5 substituents independently selected from the group consisting of (1-4C)alkyl, fluoro, hydroxy, phenyl and phenyl(1-4C)-alkyl;

$A^1$ and $A^2$ are each independently selected from (3-7C) cycloalkylene, (6-10C)arylene, (2-9C)heteroarylene and (3-6C)heterocyclene; wherein each cycloalkylene is unsubstituted or substituted with from 1 to 4 substituents selected independently from (1-4C)alkyl and each arylene, heteroarylene or heterocyclene group is unsubstituted or substituted with from 1 to 4 substituents independently selected from the group consisting of halogen, (1-4C)alkyl and (1-4C) alkoxy;

Q is selected from the group consisting of a bond, —O—, —C(O)O—, —OC(O)—, —S—, —S(O)—, $—S(O)_2—$, $—N(Q^a)C(O)—$, $—C(O)N(Q^b)$-, $—N(Q^c)S(O)_2—$, $—S(O)_2N(Q^d)$-, $—N(Q^e)C(O)N(Q^f)$-, $—N(Q^g)S(O)_2N(Q^h)$-, $—OC(O)N(Q^i)$- and $—N(Q^j)C(O)O—$;

$Q^a$, $Q^b$, $Q^c$, $Q^d$, $Q^e$, $Q^f$, $Q^g$, $Q^h$, $Q^i$ and $Q^j$ are each independently selected from the group consisting of hydrogen, (1-6C) alkyl, $A^3$ and (1-4C)alkylene-$A^4$; wherein the alkyl group is unsubstituted or substituted with from 1 to 3 substituents independently selected from fluoro, hydroxy and (1-4C) alkoxy; or together with the nitrogen atom and the group $R^{4b}$ or $R^{4c}$ to which they are attached, form a 4-6 membered azacycloalkylene group;

$A^3$ and $A^4$ are each independently selected from (3-6C) cycloalkyl, (6-10C)aryl, (2-9C)heteroaryl and (3-6C)heterocyclyl; wherein each cycloalkyl is unsubstituted or substituted with from 1 to 4 substituents selected independently from (1-4C)alkyl and each aryl, heteroaryl or heterocyclyl group is unsubstituted or substituted with from 1 to 4 substituents independently selected from the group consisting of halogen, (1-4C)alkyl and (1-4C)alkoxy;

provided that the number of contiguous atoms in the shortest chain between the two nitrogen atoms to which $R^4$ is attached is in the range of from 4 to 14;

$R^5$ represents hydrogen or (1-4C)alkyl;

$R^6$ is $—NR^{6a}CR^{6b}(O)$ or $—CR^{6c}R^{6d}OR^{6e}$ and $R^7$ is hydrogen, or $R^6$ and $R^7$ together form $—NR^{7a}C(O)—CR^{7b}=CR^{7c}—$, $—CR^{7d}=CR^{7e}—C(O)—NR^{7f}—$, $—NR^{7g}C(O)—CR^{7h}R^{7i}—CR^{7j}R^{7k}—$ or $—CR^{7l}R^{7m}—CR^{7n}R^{7o}—C(O)—NR^{7p}—$;

each of $R^{6a}$, $R^{6b}$, $R^{6c}$, $R^{6d}$ and $R^{6e}$ is independently hydrogen or (1-4C)alkyl; and each of $R^{7a}$, $R^{7b}$, $R^{7c}$, $R^{7d}$, $R^{7e}$, $R^{7f}$, $R^{7g}$, $R^{7h}$, $R^{7i}$, $R^{7j}$, $R^{7k}$, $R^{7l}$, $R^{7m}$, $R^{7n}$, $R^{7o}$ and $R^{7p}$ is independently hydrogen or (1-4C)alkyl;

or a pharmaceutically-acceptable salt or solvate or stereoisomer thereof.

Another particular group of compounds of formula I are those where: $R^1$ is oxiran-1,2-diyl; $R^2$ is methyl; $R^3$ is —OC(O)CR$^{3a}$R$^{3b}$R$^{3c}$; $R^5$ is hydrogen; and $R^{3a}$, $R^{3b}$, $R^{3c}$, $R^4$, $R^6$ and $R^7$ are as defined herein; or a pharmaceutically acceptable salt or solvate or stereoisomer thereof.

Yet another particular group of compounds of formula I are those where: $R^1$ is —$CH_2CH_2$—; $R^2$ is methyl; $R^3$ is —OC(O)CR$^{3a}$R$^{3b}$R$^{3c}$; $R^5$ is hydrogen; and $R^{3a}$, $R^{3b}$, $R^{3c}$, $R^4$, $R^6$ and $R^7$ are as defined herein; or a pharmaceutically acceptable salt or solvate or stereoisomer thereof.

Still another particular group of compounds of formula I are those where: $R^1$ is oxiran-1,2-diyl; $R^2$ is methyl; $R^3$ is —OC(O)CR$^{3a}$R$^{3b}$R$^{3c}$; $R^{3a}$ is hydroxy; $R^{3b}$ is thien-2-yl; $R^{3c}$ is thien-2-yl; $R^5$ is hydrogen; and $R^4$, $R^6$ and $R^7$ are as defined herein; or a pharmaceutically acceptable salt or solvate or stereoisomer thereof.

Still another particular group of compounds of formula I are those where: $R^1$ is —$CH_2CH_2$—; $R^2$ is methyl; $R^3$ is —OC(O)CR$^{3a}$R$^{3b}$R$^{3c}$; $R^{3a}$ is hydroxymethyl; $R^{3b}$ is phenyl; $R^{3c}$ is hydrogen; $R^5$ is hydrogen; and $R^4$, $R^6$ and $R^7$ are as defined herein; or a pharmaceutically acceptable salt or solvate or stereoisomer thereof.

Another particular group of compounds of formula I are those of formula II as defined herein; or a pharmaceutically acceptable salt or solvate or stereoisomer thereof.

Another particular group of compounds of formula I are those of formula III as defined herein; or a pharmaceutically acceptable salt or solvate or stereoisomer thereof.

Another particular group of compounds of formula I are those of formula IV as defined herein; or a pharmaceutically acceptable salt or solvate or stereoisomer thereof.

Another particular group of compounds of formula I are those of formula V as defined herein; or a pharmaceutically acceptable salt or solvate or stereoisomer thereof.

Another particular group of compounds of formula I are compounds of formula VI:

VI

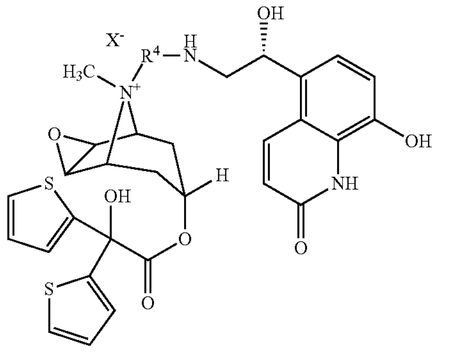

wherein $R^4$ is as defined in Table I; and $X^-$ is a pharmaceutically acceptable anion; or a pharmaceutically acceptable salt or solvate thereof.

TABLE I

| Ex. | $R^4$ |
|---|---|
| 1 | —$(CH_2)_9$— |
| 2 | —$(CH_2)_2C(O)NH(CH_2)_5$— |
| 3 | —$(CH_2)_2N(CH_3)C(O)(CH_2)_5$— |
| 4 | —$(CH_2)_2C(O)NH$(phen-1,4-ylene)$CH_2$— |

TABLE I-continued

| Ex. | $R^4$ |
|---|---|
| 5 | —$(CH_2)_2NHC(O)$(phen-1,4-ylene)$CH_2$— |
| 6 | —$(CH_2)_2NHC(O)NH(CH_2)_5$— |
| 7 | —$(CH_2)_3NHC(O)NH(CH_2)_5$— |
| 8 | —$(CH_2)_2C(O)NHCH_2$(cyclohex-1,3-ylene)$CH_2$— |
| 9 | —$(CH_2)_2NHC(O)$(cis-cyclopent-1,3-ylene)- |
| 10 | —$(CH_2)_2C(O)NH$(2-chlorophen-1,4-ylene)$CH_2$— |
| 11 | —$(CH_2)_2S(O)_2NH(CH_2)_5$— |
| 12 | —$(CH_2)_2N(CH_3)S(O)_2$(phen-1,4-ylene)$CH_2$— |
| 13 | —$(CH_2)_2NHC(O)NHCH_2$(phen-1,3-ylene)$CH_2$— |
| 14 | —$(CH_2)_3$(phen-1,4-ylene)NH(phen-1,4-ylene)$(CH_2)_2$— |
| 15 | 1-[-$CH_2$(2-fluorophen-1,3-ylene)$CH_2$](piperidin-4-yl)$CH_2$— |
| 16 | —$(CH_2)_3O$(phen-1,4-ylene)$(CH_2)_2$— |
| 17 | —$(CH_2)_4$(phen-1,4-ylene)$(CH_2)_2$— |
| 18 | —$(CH_2)_3$(thien-2,5-ylene)$(CH_2)_3$— |
| 19 | —$(CH_2)_2C(O)NH$(2-chloro-5-methoxyphen-1,4-ylene)$CH_2$— |
| 20 | —$(CH_2)_7$— |
| 21 | —$(CH_2)_8$— |
| 22 | —$(CH_2)_2NHC(O)NH$(phen-1,4-ylene)$(CH_2)_2$— |
| 23 | 1-[-$(CH_2)_2C(O)$](piperidin-4-yl)$(CH_2)_2$— |
| 24 | —$(CH_2)_2NHC(O)$(trans-cyclohex-1,4-ylene)$CH_2$— |
| 25 | —$(CH_2)_2NHC(O)$(cis-cyclopent-1,3-ylene)- |
| 26 | —$(CH_2)_2NH$(phen-1,4-ylene)$(CH_2)_2$— |
| 27 | 1-[-$(CH_2)_2NHC(O)$](piperidin-4-yl)$(CH_2)_2$— |
| 28 | —$CH_2$(phen-1,4-ylene)NH(phen-1,4-ylene)$CH_2$— |
| 29 | —$(CH_2)_2C(O)NHCH_2$(phen-1,3-ylene)$CH_2$— |
| 30 | —$(CH_2)_2C(O)NH$(phen-1,4-ylene)$CH_2$— |
| 31 | —$(CH_2)_2C(O)NHCH_2$(pyrid-2,6-ylene)$CH_2$— |
| 32 | —$(CH_2)_2C(O)NH$(cis-cyclohex-1,4-ylene)$CH_2$— |
| 33 | —$(CH_2)_2C(O)NH$(trans-cyclohex-1,4-ylene)$CH_2$— |
| 34 | —$(CH_2)_2NHC(O)$(cis-cyclopent-1,3-ylene)$CH_2$— |
| 35 | —$(CH_2)_2N(CH_3)C(O)$(phen-1,3-ylene)$CH_2$— |
| 36 | —$(CH_2)_2N(CH_3)C(O)$(trans-cyclohex-1,4-ylene)$CH_2$— |
| 37 | —$(CH_2)_2C(O)NH$(phen-1,4-ylene)$CH_2$— |
| 38 | —$(CH_2)_2C(O)NH$(phen-1,4-ylene)C*H$(CH_3)$-((S)-isomer) |
| 39 | —$(CH_2)_2C(O)NH$(phen-1,4-ylene)C*H$(CH_3)$-((R)-isomer) |
| 40 | 2-[(S)-(-$CH_2$-](pyrrolidin-1-yl)C(O)$(CH_2)_4$— |
| 41 | 2-[(S)-(-$CH_2$-](pyrrolidin-1-yl)C(O)(phen-1,4-ylene)$CH_2$— |
| 42 | —$(CH_2)_2C(O)NH$(4-chlorophen-1,3-ylene)$CH_2$— |
| 43 | —$(CH_2)_2C(O)NH$(phen-1,4-ylene)$CH_2$— |
| 44 | 1-[-$(CH_2)_2C(O)$](piperidin-4-yl)$(CH_2)_2$— |
| 45 | —$(CH_2)_2C(O)NHCH_2$(phen-1,3-ylene)$CH_2$— |
| 46 | —$CH_2$(2-fluorophen-1,3-ylene)$CH_2$— |
| 47 | —$(CH_2)_2C(O)NH$(4-methylphen-1,3-ylene)$CH_2$— |
| 48 | —$(CH_2)_2C(O)NH$(6-chlorophen-1,3-ylene)$CH_2$— |
| 49 | —$(CH_2)_2C(O)NH$(2,6-dichlorophen-1,4-ylene)$CH_2$— |
| 50 | 4-[-$CH_2$-](piperidin-1-yl)C(O)(phen-1,4-ylene)$CH_2$— |
| 51 | —$(CH_2)_2C(O)N(CH_2CH_3)$(phen-1,4-ylene)$CH_2$— |
| 52 | 1-[-$(CH_2)_2NHC(O)$](piperidin-4-yl)- |
| 53 | —$(CH_2)_2C(O)NH$(phen-1,4-ylene)$(CH_2)_2$— |
| 54 | —$(CH_2)_2NHC(O)$(thien-2,5-ylene)$CH_2$— |
| 55 | —$(CH_2)_2N(CH_3)C(O)$(3-nitrophen-1,4-ylene)$CH_2$— |
| 56 | —$(CH_2)_2N(CH_3)C(O)$(trans-cyclohex-1,4-ylene)- |
| 57 | 1-[-$CH_2$(2-fluorophen-1,3-ylene)$CH_2$](piperidin-4-yl)- |
| 58 | 5-[-$(CH_2)_2NHC(O)$](pyrid-2-yl)$CH_2$— |
| 59 | 1-[-$(CH_2)_3$](piperidin-4-yl)$CH_2$— |
| 60 | —$CH_2$(phen-1,2-ylene)NH(phen-1,4-ylene)$(CH_2)_2$— |
| 61 | 1-[-$CH_2$(2-fluorophen-1,3-ylene)$CH_2$](piperidin-4-yl)$(CH_2)_2$— |
| 62 | —$(CH_2)_3NH$(phen-1,4-ylene)$(CH_2)_2$— |
| 63 | —$(CH_2)_2C(O)NH$(3-chlorophen-1,4-ylene)$CH_2$— |
| 64 | —$(CH_2)_2C(O)NH$(2-($CF_3O$-)phen-1,4-ylene)$CH_2$— |
| 65 | —$(CH_2)_3$(phen-1,3-ylene)NH(phen-1,4-ylene)$(CH_2)_2$— |
| 66 | —$CH_2$(phen-1,3-ylene)NH(phen-1,4-ylene)$(CH_2)_2$— |
| 67 | —$(CH_2)_2C(O)NH$(2-iodophen-1,4-ylene)$CH_2$— |
| 68 | —$(CH_2)_2C(O)NH$(2-chloro-6-methylphen-1,4-ylene)$CH_2$— |
| 69 | —$(CH_2)_3C(O)NH(CH_2)_5$— |
| 70 | —$(CH_2)_2C(O)NH$(2-bromophen-1,4-ylene)$CH_2$— |
| 71 | —$(CH_2)_3$(phen-1,2-ylene)NH(phen-1,4-ylene)$(CH_2)_2$— |
| 72 | 1-[-$CH_2$(2-fluorophen-1,3-ylene)$CH_2$](piperidin-4-yl)$(CH_2)_3$— |
| 73 | —$(CH_2)_2C(O)NH$(2-methoxyphen-1,4-ylene)$CH_2$— |
| 74 | —$(CH_2)_5NH$(phen-1,4-ylene)$(CH_2)_2$— |
| 75 | 4-[-$(CH_2)_2$-](piperidin-1-yl)(phen-1,4-ylene)$(CH_2)_2$— |
| 76 | —$(CH_2)_2C(O)NH$(phen-1,4-ylene)$CH(CH_3)CH_2$— |
| 77 | —$(CH_2)_2$-(trans-cyclohex-1,4-ylene)NH(phen-1,4-ylene)$(CH_2)_2$— |
| 78 | —$(CH_2)_2C(O)NH$(2-fluorophen-1,4-ylene)$CH_2$— |
| 79 | —$(CH_2)_2$(phen-1,3-ylene)NH(phen-1,4-ylene)$(CH_2)_2$— |
| 80 | —$(CH_2)_2C(O)NH$(2,5-difluorophen-1,4-ylene)$CH_2$— |
| 81 | —$(CH_2)_2NHC(O)$(phen-1,4-ylene)$(CH_2)_2$— |

TABLE I-continued

| Ex. | $R^4$ |
|---|---|
| 82 | 1-[-$CH_2$(pyrid-2,6-ylene)$CH_2$](piperidin-4-yl)$CH_2$— |
| 83 | —$(CH_2)_2$NH(naphth-1,4-ylene)$(CH_2)_2$— |
| 84 | 4-[-$(CH_2)_2$](piperidin-1-yl)C(O)(phen-1,4-ylene)$CH_2$— |
| 85 | —$(CH_2)_3$(phen-1,4-ylene)NHC(O)$(CH_2)_2$— |
| 86 | —$(CH_2)_3$O(phen-1,4-ylene)$CH_2$— |
| 87 | 2-[-$(CH_2)_2$](benzimidazol-5-yl)$CH_2$— |
| 88 | —$(CH_2)_2$-(trans-cyclohex-1,4-ylene)NHC(O)$(CH_2)_2$— |
| 89 | —$(CH_2)_2$-(trans-cyclohex-1,4-ylene)NHC(O)$(CH_2)_4$— |
| 90 | —$(CH_2)_2$-(trans-cyclohex-1,4-ylene)NHC(O)$(CH_2)_5$— |
| 91 | 4-[—$(CH_2)_2$](piperidin-1-yl)C(O)$(CH_2)_2$— |
| 92 | —$(CH_2)_2$NHC(O)NH(phen-1,4-ylene)$CH_2$— |
| 93 | —$(CH_2)_2$N($CH_3$)$(CH_2)_2$(cis-cyclohex-1,4-ylene)- |
| 94 | —$(CH_2)_2$C(O)NH(2,3,5,6-tetrafluorophen-1,4-ylene)$CH_2$— |
| 95 | —$(CH_2)_2$C(O)NH(2,6-diiodophen-1,4-ylene)$CH_2$— |
| 96 | 4-[-$(CH_2)_2$](piperidin-1-yl)C(O)$(CH_2)_3$— |
| 97 | 4-[-$(CH_2)_2$](piperidin-1-yl)C(O)$(CH_2)_4$— |
| 98 | 4-[-$(CH_2)_2$](piperidin-1-yl)C(O)$(CH_2)_5$— |
| 99 | —$(CH_2)_2$C(O)NH$CH_2$(phen-1,4-ylene)$CH_2$— |
| 100 | —$(CH_2)_2$NHC(O)NH$CH_2$(phen-1,4-ylene)$CH_2$— |
| 101 | —$(CH_2)_2$C(O)NH(2-methylphen-1,4-ylene)$CH_2$— |
| 192 | 1-[-$(CH_2)_3$O(phen-1,4-ylene)$(CH_2)_2$](piperidin-4-yl)$CH_2$— |
| 103 | —$(CH_2)_2$C(O)NH$CH_2$(phen-1,3-ylene)$(CH_2)_2$— |
| 104 | —$(CH_2)_2$O(phen-1,3-ylene)$CH_2$— |
| 105 | —$(CH_2)_2$N($CH_3$)C(O)$CH_2$O(phen-1,4-ylene)$CH_2$— |
| 106 | —$(CH_2)_2$N($CH_3$)C(O)$CH_2$O(phen-1,3-ylene)$CH_2$— |
| 107 | —$(CH_2)_2$N($CH_3$)C(O)(fur-2,5-ylene)$CH_2$— |
| 108 | —$(CH_2)_2$N($CH_3$)C(O)(thien-2,5-ylene)$CH_2$— |
| 109 | —$(CH_2)_2$O(phen-1,4-ylene)O$(CH_2)_2$— |
| 110 | —$(CH_2)_2$(trans-cyclohex-1,4-ylene)NHC(O)(phen-1,4-ylene)$CH_2$— |
| 111 | —$(CH_2)_2$(trans-cyclohex-1,4-ylene)NHC(O)$CH_2$O(phen-1,2-ylene)$CH_2$— |
| 112 | —$(CH_2)_2$(trans-cyclohex-1,4-ylene)NHC(O)$CH_2$O(phen-1,3-ylene)$CH_2$— |
| 113 | —$(CH_2)_2$(trans-cyclohex-1,4-ylene)NHC(O)$CH_2$O(phen-1,4-ylene)$CH_2$— |
| 114 | —$(CH_2)_2$(trans-cyclohex-1,4-ylene)NHC(O)(fur-2,5-ylene)$CH_2$— |
| 115 | —$(CH_2)_2$(trans-cyclohex-1,4-ylene)NHC(O)(thien-2,5-ylene)$CH_2$— |
| 116 | 4-[-$(CH_2)_2$](piperidin-1-yl)C(O)$CH_2$O(phen-1,2-ylene)$CH_2$— |
| 117 | 4-[-$(CH_2)_2$](piperidin-1-yl)C(O)$CH_2$O(phen-1,3-ylene)$CH_2$— |
| 118 | 4-[-$(CH_2)_2$](piperidin-1-yl)C(O)$CH_2$O(phen-1,4-ylene)$CH_2$— |
| 119 | 4-[-$(CH_2)_2$](piperidin-1-yl)C(O)(fur-2,5-ylene)$CH_2$— |
| 120 | 4-[-$(CH_2)_2$](piperidin-1-yl)C(O)(thien-2,5-ylene)$CH_2$— |
| 121 | —$(CH_2)_2$(phen-1,4-ylene)NHC(O)(phen-1,3-ylene)$CH_2$— |
| 122 | —$(CH_2)_2$(phen-1,4-ylene)NHC(O)(phen-1,4-ylene)$CH_2$— |
| 123 | —$(CH_2)_2$(phen-1,4-ylene)NHC(O)$CH_2$O(phen-1,2-ylene)$CH_2$— |
| 124 | —$(CH_2)_2$(phen-1,4-ylene)NHC(O)$CH_2$O(phen-1,3-ylene)$CH_2$— |
| 125 | —$(CH_2)_2$(phen-1,4-ylene)NHC(O)$CH_2$O(phen-1,4-ylene)$CH_2$— |
| 126 | —$(CH_2)_2$(phen-1,4-ylene)NHC(O)(fur-2,5-ylene)$CH_2$— |
| 127 | —$(CH_2)_2$(phen-1,4-ylene)NHC(O)(thien-2,5-ylene)$CH_2$— |
| 128 | —$(CH_2)_2$(trans-cyclohex-1,4-ylene)NHC(O)(phen-1,3-ylene)$CH_2$— |
| 129 | —$(CH_2)_3$O(phen-1,3-ylene)$CH_2$— |
| 130 | —$CH_2$CH(OH)$CH_2$NH(phen-1,4-ylene)$(CH_2)_2$— |
| 131 | —$(CH_2)_4$NH(phen-1,4-ylene)$(CH_2)_2$— |
| 132 | —$(CH_2)_2$C(O)NH(phen-1,4-ylene)$CH_2$NHC(O)$CH_2$— |
| 133 | —$(CH_2)_2$C(O)NH(phen-1,4-ylene)$(CH_2)_2$NHC(O)$CH_2$— |
| 134 | —$(CH_2)_2$C(O)NH$CH_2$(trans-cyclohex-1,4-ylene)$CH_2$— |
| 135 | —$(CH_2)_2$NHC(O)$(CH_2)_5$— |
| 136 | —$(CH_2)_2$O(phen-1,3-ylene)O$(CH_2)_2$— |
| 137 | —$(CH_2)_2$O(phen-1,2-ylene)O$(CH_2)_2$— |
| 138 | —$CH_2$(phen-1,2-ylene)O(phen-1,2-ylene)$CH_2$— |
| 139 | —$(CH_2)_2$C(O)NH$(CH_2)_6$— |
| 140 | —$(CH_2)_2$NHC(O)(cis-cyclopent-1,3-ylene)- |
| 141 | —$(CH_2)_3$(phen-1,4-ylene)$(CH_2)_3$— |
| 142 | —$(CH_2)_3$(phen-1,4-ylene)$(CH_2)_2$— |
| 143 | —$(CH_2)_4$(phen-1,4-ylene)$(CH_2)_2$— |
| 144 | —$(CH_2)_3$(furan-2,5-ylene)$(CH_2)_3$— |
| 145 | —$(CH_2)_2$N($CH_3$)C(O)NH(phen-1,4-ylene)$(CH_2)_2$— |
| 146 | 4-[-$(CH_2)_2$](piperidin-1-yl)C(O)NH(phen-1,4-ylene)$(CH_2)_2$— |
| 147 | —$(CH_2)_3$(phen-1,3-ylene)$(CH_2)_3$— |
| 148 | —$(CH_2)_3$(tetrahydrofuran-2,5-ylene)$(CH_2)_3$— |
| 149 | —$(CH_2)_2$O(phen-1,4-ylene)C(O)$(CH_2)_2$— |

Another particular group of compounds of formula I are compounds of formula VII:

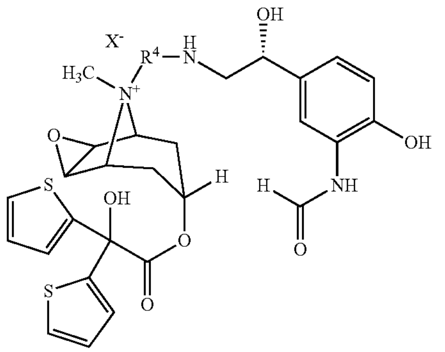

VII wherein $R^4$ is as defined in Table II; and $X^-$ is a pharmaceutically acceptable anion; or a pharmaceutically acceptable salt or solvate thereof.

TABLE II

| Ex. | $R^4$ |
|---|---|
| 150 | —$(CH_2)_9$— |
| 151 | —$(CH_2)_{10}$— |
| 152 | —$(CH_2)_2$C(O)NH$(CH_2)_5$— |
| 153 | —$(CH_2)_2$N($CH_3$)C(O)$(CH_2)_5$— |
| 154 | —$(CH_2)_2$C(O)NH(phen-1,4-ylene)$CH_2$— |
| 155 | —$(CH_2)_2$NHC(O)(phen-1,4-ylene)$CH_2$— |
| 156 | —$(CH_2)_2$NHC(O)NH$(CH_2)_5$— |
| 157 | —$(CH_2)_3$NHC(O)NH$(CH_2)_5$— |
| 158 | —$(CH_2)_2$C(O)NH$CH_2$(cyclohex-1,3-ylene)$CH_2$— |
| 159 | —$(CH_2)_2$NHC(O)(cis-cyclopent-1,3-ylene)- |
| 160 | —$(CH_2)_2$C(O)NH(2-chlorophen-1,4-ylene)$CH_2$— |
| 161 | —$(CH_2)_2$S(O)$_2$NH$(CH_2)_5$— |
| 162 | —$(CH_2)_2$N($CH_3$)S(O)$_2$(phen-1,4-ylene)$CH_2$— |
| 163 | —$(CH_2)_2$NHC(O)NH$CH_2$(phen-1,3-ylene)$CH_2$— |
| 164 | —$(CH_2)_3$(phen-1,4-ylene)NH(phen-1,4-ylene)$(CH_2)_2$— |
| 165 | 1-[-$CH_2$(2-fluorophen-1,3-ylene)$CH_2$](piperidin-4-yl)$CH_2$— |
| 166 | —$(CH_2)_3$O(phen-1,4-ylene)$(CH_2)_2$— |
| 167 | —$(CH_2)_4$(phen-1,4-ylene)$(CH_2)_2$— |
| 168 | —$(CH_2)_3$(thien-2,5-ylene)$(CH_2)_3$— |
| 169 | —$(CH_2)_2$C(O)NH(2-chloro-5-methoxyphen-1,4-ylene)$CH_2$— |
| 170 | —$(CH_2)_7$— |
| 171 | —$(CH_2)_8$— |
| 172 | —$(CH_2)_2$NHC(O)NH(phen-1,4-ylene)$(CH_2)_2$— |
| 173 | 1-[-$(CH_2)_2$C(O)](piperidin-4-yl)$(CH_2)_2$— |
| 174 | —$(CH_2)_2$NHC(O)(trans-cyclohex-1,4-ylene)$CH_2$— |
| 175 | —$(CH_2)_2$NHC(O)(cis-cyclopent-1,3-ylene)- |
| 176 | —$(CH_2)_2$NH(phen-1,4-ylene)$(CH_2)_2$— |
| 177 | 1-[-$(CH_2)_2$NHC(O)](piperidin-4-yl)$(CH_2)_2$— |
| 178 | —$CH_2$(phen-1,4-ylene)NH(phen-1,4-ylene)$CH_2$— |
| 179 | —$(CH_2)_2$C(O)NH$CH_2$(phen-1,3-ylene)$CH_2$— |
| 180 | —$(CH_2)_2$C(O)NH(phen-1,4-ylene)$CH_2$— |
| 181 | —$(CH_2)_2$C(O)NH$CH_2$(pyrid-2,6-ylene)$CH_2$— |
| 182 | —$(CH_2)_2$C(O)NH(cis-cyclohex-1,4-ylene)$CH_2$— |
| 183 | —$(CH_2)_2$C(O)NH(trans-cyclohex-1,4-ylene)$CH_2$— |
| 184 | —$(CH_2)_2$NHC(O)(cis-cyclopent-1,3-ylene)$CH_2$— |
| 185 | —$(CH_2)_2$N($CH_3$)C(O)(phen-1,3-ylene)$CH_2$— |
| 186 | —$(CH_2)_2$N($CH_3$)C(O)(trans-cyclohex-1,4-ylene)$CH_2$— |
| 187 | —$(CH_2)_2$C(O)NH(phen-1,4-ylene)$CH_2$— |
| 188 | —$(CH_2)_2$C(O)NH(phen-1,4-ylene)C*H($CH_3$)-((S)-isomer) |
| 189 | —$(CH_2)_2$C(O)NH(phen-1,4-ylene)C*H($CH_3$)-((R)-isomer) |
| 190 | 2-[(S)-(-$CH_2$-](pyrrolidin-1-yl)C(O)$(CH_2)_4$— |
| 191 | 2-[(S)-(-$CH_2$-](pyrrolidin-1-yl)C(O)(phen-1,4-ylene)$CH_2$— |
| 192 | —$(CH_2)_2$C(O)NH(4-chlorophen-1,3-ylene)$CH_2$— |
| 193 | —$(CH_2)_2$C(O)NH(phen-1,4-ylene)$CH_2$— |
| 194 | 1-[-$(CH_2)_2$C(O)](piperidin-4-yl)$(CH_2)_2$— |
| 195 | —$(CH_2)_2$C(O)NH$CH_2$(phen-1,3-ylene)$CH_2$— |
| 196 | —$CH_2$(2-fluorophen-1,3-ylene)$CH_2$— |
| 197 | —$(CH_2)_2$C(O)NH(4-methylphen-1,3-ylene)$CH_2$— |
| 198 | —$(CH_2)_2$C(O)NH(6-chlorophen-1,3-ylene)$CH_2$— |
| 199 | —$(CH_2)_2$C(O)NH(2,6-dichlorophen-1,4-ylene)$CH_2$— |
| 200 | 4-[-$CH_2$-](piperidin-1-yl)C(O)(phen-1,4-ylene)$CH_2$— |
| 201 | —$(CH_2)_2$C(O)N($CH_2CH_3$)(phen-1,4-ylene)$CH_2$— |
| 202 | 1-[-$(CH_2)_2$NHC(O)](piperidin-4-yl)- |

TABLE II-continued

| Ex. | $R^4$ |
| --- | --- |
| 203 | —$(CH_2)_2$C(O)NH(phen-1,4-ylene)$(CH_2)_2$— |
| 204 | —$(CH_2)_2$NHC(O)(thien-2,5-ylene)$CH_2$— |
| 205 | —$(CH_2)_2$N$(CH_3)$C(O)(3-nitrophen-1,4-ylene)$CH_2$— |
| 206 | —$(CH_2)_2$N$(CH_3)$C(O)(trans-cyclohex-1,4-ylene)- |
| 207 | 1-[-$CH_2$(2-fluorophen-1,3-ylene)$CH_2$](piperidin-4-yl)- |
| 208 | 5-[-$(CH_2)_2$NHC(O)](pyrid-2-yl)$CH_2$— |
| 209 | 1-[-$(CH_2)_3$](piperidin-4-yl)$CH_2$— |
| 210 | —$CH_2$(phen-1,2-ylene)NH(phen-1,4-ylene)$(CH_2)_2$— |
| 211 | 1-[-$CH_2$(2-fluorophen-1,3-ylene)$CH_2$](piperidin-4-yl)$(CH_2)_2$— |
| 212 | —$(CH_2)_3$NH(phen-1,4-ylene)$(CH_2)_2$— |
| 213 | —$(CH_2)_2$C(O)NH(3-chlorophen-1,4-ylene)$CH_2$— |
| 214 | —$(CH_2)_2$C(O)NH(2-($CF_3$O-)phen-1,4-ylene)$CH_2$— |
| 215 | —$(CH_2)_3$(phen-1,3-ylene)NH(phen-1,4-ylene)$(CH_2)_2$— |
| 216 | —$CH_2$(phen-1,3-ylene)NH(phen-1,4-ylene)$(CH_2)_2$— |
| 217 | —$(CH_2)_2$C(O)NH(2-iodophen-1,4-ylene)$CH_2$— |
| 218 | —$(CH_2)_2$C(O)NH(2-chloro-6-methylphen-1,4-ylene)$CH_2$— |
| 219 | —$(CH_2)_3$C(O)NH$(CH_2)_5$— |
| 220 | —$(CH_2)_2$C(O)NH(2-bromophen-1,4-ylene)$CH_2$— |
| 221 | —$(CH_2)_3$(phen-1,2-ylene)NH(phen-1,4-ylene)$(CH_2)_2$— |
| 222 | 1-[-$CH_2$(2-fluorophen-1,3-ylene)$CH_2$](piperidin-4-yl)$(CH_2)_3$— |
| 223 | —$(CH_2)_2$C(O)NH(2-methoxyphen-1,4-ylene)$CH_2$— |
| 224 | —$(CH_2)_5$NH(phen-1,4-ylene)$(CH_2)_2$— |
| 225 | 4-[-$(CH_2)_2$-](piperidin-1-yl)(phen-1,4-ylene)$(CH_2)_2$— |
| 226 | —$(CH_2)_2$C(O)NH(phen-1,4-ylene)CH$(CH_3)$$CH_2$— |
| 227 | —$(CH_2)_2$-(trans-cyclohex-1,4-ylene)NH(phen-1,4-ylene)$(CH_2)_2$— |
| 228 | —$(CH_2)_2$C(O)NH(2-fluorophen-1,4-ylene)$CH_2$— |
| 229 | —$(CH_2)_2$(phen-1,3-ylene)NH(phen-1,4-ylene)$(CH_2)_2$— |
| 230 | —$(CH_2)_2$C(O)NH(2,5-difluorophen-1,4-ylene)$CH_2$— |
| 231 | —$(CH_2)_2$NHC(O)(phen-1,4-ylene)$(CH_2)_2$— |
| 232 | 1-[-$CH_2$(pyrid-2,6-ylene)$CH_2$](piperidin-4-yl)$CH_2$— |
| 233 | —$(CH_2)_2$NH(naphth-1,4-ylene)$(CH_2)_2$— |
| 234 | 4-[-$(CH_2)_2$](piperidin-1-yl)C(O)(phen-1,4-ylene)$CH_2$— |
| 235 | —$(CH_2)_3$(phen-1,4-ylene)NHC(O)$(CH_2)_2$— |
| 236 | —$(CH_2)_3$O(phen-1,4-ylene)$CH_2$— |
| 237 | 2-[-$(CH_2)_2$](benzimidazol-5-yl)$CH_2$— |
| 238 | —$(CH_2)_2$-(trans-cyclohex-1,4-ylene)NHC(O)$(CH_2)_2$— |
| 239 | —$(CH_2)_2$-(trans-cyclohex-1,4-ylene)NHC(O)$(CH_2)_4$— |
| 240 | —$(CH_2)_2$-(trans-cyclohex-1,4-ylene)NHC(O)$(CH_2)_5$— |
| 241 | 4-[-$(CH_2)_2$](piperidin-1-yl)C(O)$(CH_2)_2$— |
| 242 | —$(CH_2)_2$NHC(O)NH(phen-1,4-ylene)$CH_2$— |
| 243 | —$(CH_2)_2$N$(CH_3)$$(CH_2)_2$(cis-cyclohex-1,4-ylene)- |
| 244 | —$(CH_2)_2$C(O)NH(2,3,5,6-tetrafluorophen-1,4-ylene)$CH_2$— |
| 245 | —$(CH_2)_2$C(O)NH(2,6-diiodophen-1,4-ylene)$CH_2$— |
| 246 | 4-[-$(CH_2)_2$](piperidin-1-yl)C(O)$(CH_2)_3$— |
| 247 | 4-[-$(CH_2)_2$](piperidin-1-yl)C(O)$(CH_2)_4$— |
| 248 | 4-[-$(CH_2)_2$](piperidin-1-yl)C(O)$(CH_2)_5$— |
| 249 | —$(CH_2)_2$C(O)NH$CH_2$(phen-1,4-ylene)$CH_2$— |
| 250 | —$(CH_2)_2$NHC(O)NH$CH_2$(phen-1,4-ylene)$CH_2$— |
| 251 | —$(CH_2)_2$C(O)NH(2-methylphen-1,4-ylene)$CH_2$— |
| 252 | 1-[-$(CH_2)_3$O(phen-1,4-ylene)$(CH_2)_2$](piperidin-4-yl)$CH_2$— |
| 253 | —$(CH_2)_2$C(O)NH$CH_2$(phen-1,3-ylene)$(CH_2)_2$— |
| 254 | —$(CH_2)_2$O(phen-1,3-ylene)$CH_2$— |
| 255 | —$(CH_2)_2$N$(CH_3)$C(O)$CH_2$O(phen-1,4-ylene)$CH_2$— |
| 256 | —$(CH_2)_2$N$(CH_3)$C(O)$CH_2$O(phen-1,3-ylene)$CH_2$— |
| 257 | —$(CH_2)_2$N$(CH_3)$C(O)(fur-2,5-ylene)$CH_2$— |
| 258 | —$(CH_2)_2$N$(CH_3)$C(O)(thien-2,5-ylene)$CH_2$— |
| 259 | —$(CH_2)_2$O(phen-1,4-ylene)O$(CH_2)_2$— |
| 260 | —$(CH_2)_2$(trans-cyclohex-1,4-ylene)NHC(O)(phen-1,4-ylene)$CH_2$— |
| 261 | —$(CH_2)_2$(trans-cyclohex-1,4-ylene)NHC(O)$CH_2$O(phen-1,2-ylene)$CH_2$— |
| 262 | —$(CH_2)_2$(trans-cyclohex-1,4-ylene)NHC(O)$CH_2$O(phen-1,3-ylene)$CH_2$— |
| 263 | —$(CH_2)_2$(trans-cyclohex-1,4-ylene)NHC(O)$CH_2$O(phen-1,4-ylene)$CH_2$— |
| 264 | —$(CH_2)_2$(trans-cyclohex-1,4-ylene)NHC(O)(fur-2,5-ylene)$CH_2$— |
| 265 | —$(CH_2)_2$(trans-cyclohex-1,4-ylene)NHC(O)(thien-2,5-ylene)$CH_2$— |
| 266 | 4-[-$(CH_2)_2$](piperidin-1-yl)C(O)$CH_2$O(phen-1,2-ylene)$CH_2$— |
| 267 | 4-[-$(CH_2)_2$](piperidin-1-yl)C(O)$CH_2$O(phen-1,3-ylene)$CH_2$— |
| 268 | 4-[-$(CH_2)_2$](piperidin-1-yl)C(O)$CH_2$O(phen-1,4-ylene)$CH_2$— |
| 269 | 4-[-$(CH_2)_2$](piperidin-1-yl)C(O)(fur-2,5-ylene)$CH_2$— |
| 270 | 4-[-$(CH_2)_2$](piperidin-1-yl)C(O)(thien-2,5-ylene)$CH_2$— |
| 271 | —$(CH_2)_2$(phen-1,4-ylene)NHC(O)(phen-1,3-ylene)$CH_2$— |
| 272 | —$(CH_2)_2$(phen-1,4-ylene)NHC(O)(phen-1,4-ylene)$CH_2$— |
| 273 | —$(CH_2)_2$(phen-1,4-ylene)NHC(O)$CH_2$O(phen-1,2-ylene)$CH_2$— |
| 274 | —$(CH_2)_2$(phen-1,4-ylene)NHC(O)$CH_2$O(phen-1,3-ylene)$CH_2$— |
| 275 | —$(CH_2)_2$(phen-1,4-ylene)NHC(O)$CH_2$O(phen-1,4-ylene)$CH_2$— |

TABLE II-continued

| Ex. | $R^4$ |
| --- | --- |
| 276 | —$(CH_2)_2$(phen-1,4-ylene)NHC(O)(fur-2,5-ylene)$CH_2$— |
| 277 | —$(CH_2)_2$(phen-1,4-ylene)NHC(O)(thien-2,5-ylene)$CH_2$— |
| 278 | —$(CH_2)_2$(trans-cyclohex-1,4-ylene)NHC(O)(phen-1,3-ylene)$CH_2$— |
| 279 | —$(CH_2)_3$O(phen-1,3-ylene)$CH_2$— |
| 280 | —$CH_2$CH(OH)$CH_2$NH(phen-1,4-ylene)$(CH_2)_2$— |
| 281 | —$(CH_2)_4$NH(phen-1,4-ylene)$(CH_2)_2$— |
| 282 | —$(CH_2)_2$C(O)NH(phen-1,4-ylene)$CH_2$NHC(O)$CH_2$— |
| 283 | —$(CH_2)_2$C(O)NH(phen-1,4-ylene)$(CH_2)_2$NHC(O)$CH_2$— |
| 284 | —$(CH_2)_2$C(O)NH$CH_2$(trans-cyclohex-1,4-ylene)$CH_2$— |
| 285 | —$(CH_2)_2$NHC(O)$(CH_2)_5$— |
| 286 | —$(CH_2)_2$O(phen-1,3-ylene)O$(CH_2)_2$— |
| 287 | —$(CH_2)_2$O(phen-1,2-ylene)O$(CH_2)_2$— |
| 288 | —$CH_2$(phen-1,2-ylene)O(phen-1,2-ylene)$CH_2$— |
| 289 | —$(CH_2)_2$C(O)NH$(CH_2)_6$— |
| 290 | —$(CH_2)_2$NHC(O)(cis-cyclopent-1,3-ylene)- |
| 291 | —$(CH_2)_3$(phen-1,4-ylene)$(CH_2)_3$— |
| 292 | —$(CH_2)_3$(phen-1,4-ylene)$(CH_2)_2$— |
| 293 | —$(CH_2)_4$(phen-1,4-ylene)$(CH_2)_2$— |
| 294 | —$(CH_2)_3$(furan-2,5-ylene)$(CH_2)_3$— |
| 295 | —$(CH_2)_2$N$(CH_3)$C(O)NH(phen-1,4-ylene)$(CH_2)_2$— |
| 296 | 4-[-$(CH_2)_2$](piperidin-1-yl)C(O)NH(phen-1,4-ylene)$(CH_2)_2$— |
| 297 | —$(CH_2)_3$(phen-1,3-ylene)$(CH_2)_3$— |
| 298 | —$(CH_2)_3$(tetrahydrofuran-2,5-ylene)$(CH_2)_3$— |
| 299 | —$(CH_2)_2$O(phen-1,4-ylene)C(O)$(CH_2)_2$— |

DEFINITIONS

When describing the compounds, compositions, methods and processes of this invention, the following terms have the following meanings unless otherwise indicated.

The term "alkyl" means a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkylene" means a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "alkoxy" means a monovalent group of the formula (alkyl)-O—, where alkyl is as defined herein. Representative alkoxy groups include, by way of example, methoxy, ethoxy, n-propoxy, isopropoxy, n-butoxy, sec-butoxy, isobutoxy, tert-butoxy and the like.

The term "alkenyl" means a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms. Representative alkenyl groups include, by way of example, ethenyl, n-propenyl, isopropenyl, n-but-2-enyl, n-hex-3-enyl and the like. The term "alkenylene" means a divalent alkenyl group.

The term "alkynyl" means a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms. Representative alkynyl groups include, by way of example, ethynyl, n-propynyl, n-but-2-ynyl, n-hex-3-ynyl and the like. The term "alkynylene" means a divalent alkynyl group.

The term "aryl" means a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like. The term "arylene" means a divalent aryl group.

The term "azacycloalkyl" means a monovalent heterocyclic ring containing one nitrogen atom, i.e., a cycloalkyl group in which one carbon atom has been replaced with a nitrogen atom. Unless otherwise defined, such azacycloalkyl groups typically contain from 2 to 9 carbon atoms. Representative examples of an azacycloalkyl group are pyrrolidinyl and piperidinyl groups. The term "azacycloalkylene" means a divalent azacycloalkyl group. Representative examples of an azacycloalkylene group are pyrrolidinylene and piperidinylene groups.

The term "cycloalkyl" means a monovalent saturated carbocyclic hydrocarbon group. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl and the like. The term "cycloalkylene" means a divalent cycloalkyl group.

The term "halo" means fluoro, chloro, bromo and iodo.

The term "heteroaryl" means a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom. The term "heteroarylene" means a divalent heteroaryl group.

The term "heterocyclyl" or "heterocyclic" means a monovalent saturated or unsaturated (non-aromatic) group having a single ring or multiple condensed rings and containing in the ring at least one heteroatom (typically 1 to 3 heteroatoms) selected from nitrogen, oxygen or sulfur. Unless otherwise defined, such heterocyclic groups typically contain from 2 to 9 total ring carbon atoms. Representative heterocyclic groups include, by way of example, monovalent species of pyrrolidine, imidazolidine, pyrazolidine, piperidine, 1,4-dioxane, morpholine, thiomorpholine, piperazine, 3-pyrroline and the like, where the point of attachment is at any available carbon or nitrogen ring atom. The term "heterocyclene" means a divalent heterocyclyl or heterocyclic group.

When a specific number of carbon atoms is intended for a particular term used herein, the number of carbon atoms is shown in parentheses preceding the term. For example, the term "(1-4C)alkyl" means an alkyl group having from 1 to 4 carbon atoms.

The term "pharmaceutically acceptable salt" means a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids. Salts derived from pharmaceutically acceptable inorganic bases include ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable acids include acetic, ascorbic, benzenesulfonic, benzoic, camphosulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic, xinafoic and the like. Particularly preferred are citric, hydrobromic, hydrochloric, isethionic, maleic, naphthalene-1,5-disulfonic, phosphoric, sulfuric and tartaric acids.

The term "salt thereof" means a compound formed when the hydrogen of an acid is replaced by a cation, such as a metal cation or an organic cation and the like. Preferably, the salt is a pharmaceutically acceptable salt, although this is not required for salts of intermediate compounds that are not intended for administration to a patient.

The term "pharmaceutically acceptable anion" means an anion which is acceptable for administration to a patient, such as a mammal (e.g., salts having acceptable mammalian safety for a given dosage regime). Representative pharmaceutically acceptable anions include acetate, ascorbate, benzenesulfonate, benzoate, camphosulfonate, citrate, ethanesulfonate, edisylate, fumarate, gentisate, gluconate, glucoronate, glutamate, hippurate, bromide, chloride, isethionate, lactate, lactobionate, maleate, malate, mandelate, methanesulfonate, mucate, naphthalenesulfonate, naphthalene-1,5-disulfonate, naphthalene-2,6-disulfonate, nicotinate, nitrate, orotate, pamate, pantothenate, phosphate, succinate, sulfate, tartrate, p-toluenesulfonate, xinafate and the like.

The term "solvate" means a complex or aggregate formed by one or more molecules of a solute, i.e. a compound of formula I or a pharmaceutically acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

It will be appreciated that the term "or a pharmaceutically acceptable salt or solvate or stereoisomer thereof" is intended to include all permutations of salts, solvates and stereoisomers, such as a solvate of a pharmaceutically acceptable salt of a stereoisomer of a compound of formula I.

The term "therapeutically effective amount" means an amount sufficient to effect treatment when administered to a patient in need of treatment.

The term "treating" or "treatment" as used herein means the treating or treatment of a disease or medical condition (such as COPD) in a patient, such as a mammal (particularly a human) that includes:

(a) preventing the disease or medical condition from occurring, i.e., prophylactic treatment of a patient;

(b) ameliorating the disease or medical condition, i.e., eliminating or causing regression of the disease or medical condition in a patient;

(c) suppressing the disease or medical condition, i.e., slowing or arresting the development of the disease or medical condition in a patient; or (d) alleviating the symptoms of the disease or medical condition in a patient.

The term “leaving group” means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term “protected derivatives thereof” means a derivative of the specified compound in which one or more functional groups of the compound are protected from undesired reactions with a protecting or blocking group. Functional groups which may be protected include, by way of example, carboxylic acid groups, amino groups, hydroxy groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxy groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

The term “amino-protecting group” means a protecting group suitable for preventing undesired reactions at an amino group. Representative amino-protecting groups include, but are not limited to, tert-butoxycarbonyl (BOC), trityl (Tr), benzyloxycarbonyl (Cbz), 9-fluorenylmethoxycarbonyl (Fmoc), formyl, trimethylsilyl (TMS), tert-butyldimethylsilyl (TBS), and the like.

The term “carboxy-protecting group” means a protecting group suitable for preventing undesired reactions at a carboxy group. Representative carboxy-protecting groups include, but are not limited to, esters, such as methyl, ethyl, tert-butyl, benzyl (Bn), p-methoxybenzyl (PMB), 9-fluoroenylmethyl (Fm), trimethylsilyl (TMS), tert-butyldimethylsilyl (TBS), diphenylmethyl (benzhydryl, DPM) and the like.

The term “hydroxy-protecting group” means a protecting group suitable for preventing undesirable reactions at a hydroxy group. Representative hydroxy-protecting groups include, but are not limited to, silyl groups including tri(1-6C)alkylsilyl groups, such as trimethylsilyl (TMS), triethylsilyl (TES), tert-butyldimethylsilyl (TBS) and the like; esters (acyl groups) including (1-6C)alkanoyl groups, such as formyl, acetyl and the like; arylmethyl groups, such as benzyl (Bn), p-methoxybenzyl (PMB), 9-fluorenylmethyl (Fm), diphenylmethyl (benzhydryl, DPM) and the like. Additionally, two hydroxy groups can also be protected as an alkylidene group, such as prop-2-ylidine, formed, for example, by reaction with a ketone, such as acetone.

General Synthetic Procedures

The compounds of this invention can be prepared from readily available starting materials using the following general methods and procedures or by using other information readily available to those of ordinary skill in the art. Although a particular embodiment of the present invention may be shown or described herein, those skilled in the art will recognize that all embodiments or aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by one skilled in the art by routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions for protection and deprotection of such functional groups are well-known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Third Edition, Wiley, New York, 1999, and references cited therein.

By way of illustration, the compounds of this invention can be prepared by a process comprising:

(a) reacting a compound of formula 1:

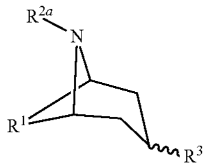

1 wherein $R^{2a}$ represents hydrogen or $R^2$; or a salt or protected derivative thereof; with a compound of formula 2:

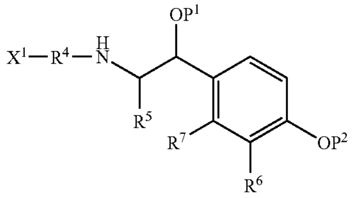

2 wherein $X^1$ represents a leaving group, and $P^1$ and $P^2$ each independently represent hydrogen or a hydroxy-protecting group;

(b) reacting a compound of formula 3:

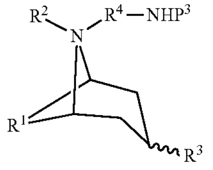

3 wherein $P^3$ represents hydrogen or an amino-protecting group, or a salt or protected derivative thereof; with a compound of formula 4:

4

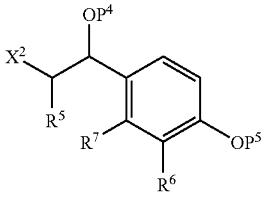

wherein $X^2$ represents a leaving group, and $P^4$ and $P^5$ each independently represent hydrogen or a hydroxy-protecting group;

(c) coupling a compound of formula 5:

5

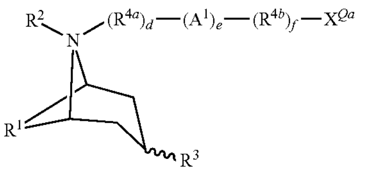

or a salt or protected derivative thereof, with a compound of formula 6:

6

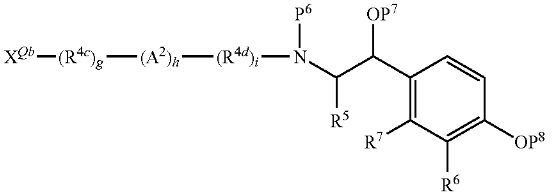

wherein $X^{Qa}$ and $X^{Qb}$ each independently represent functional groups that couple to form a group Q, $P^6$ represents hydrogen or an amino-protecting group; and $P^7$ and $P^8$ each independently represent hydrogen or a hydroxy-protecting group;

(d) for a compound of formula I wherein $R^5$ represents hydrogen, reacting a compound of formula 3 with a compound of formula 7:

7

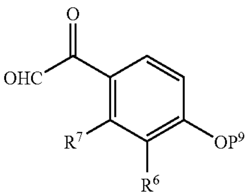

or a hydrate thereof (e.g., a glyoxal), wherein $P^9$ represents hydrogen or a hydroxy-protecting group, in the presence of a reducing agent;

(e) reacting a compound of formula 1 with a compound of formula 8:

8

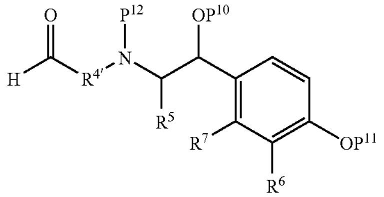

or a hydrate thereof, in the presence of a reducing agent, wherein $P^{10}$ and $P^{11}$ each independently represent hydrogen or a hydroxy-protecting group; $P^{12}$ represents hydrogen or an amino-protecting group; and $R^{4'}$ represents a residue that, together with the carbon to which it is attached, affords a group $R^4$ upon completion of the reaction;

(f) reacting a compound of formula 9:

9

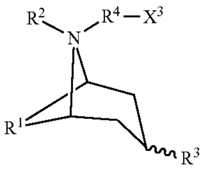

wherein $X^3$ represents a leaving group, or a salt or protected derivative thereof, with a compound of formula 10:

10

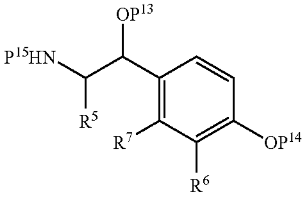

wherein $P^{13}$ and $P^{14}$ each independently represent hydrogen or a hydroxy-protecting group, and $P^{15}$ represents hydrogen or an amino-protecting group;

(g) reacting a compound of formula 11:

11

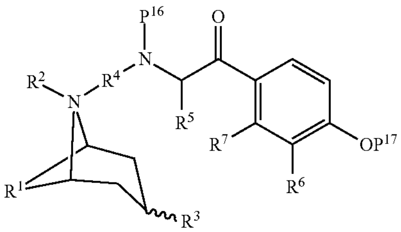

with a reducing agent; wherein $P^{16}$ represents hydrogen or an amino-protecting group; and $P^{17}$ represents hydrogen or a hydroxy-protecting group; or a salt or protected derivative thereof;

(h) reacting a compound of formula 12:

12

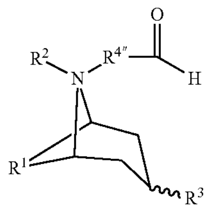

or a salt or hydrate or protected derivative thereof; wherein $R^{4''}$ represents a residue that, together with the carbon to which it is attached, affords an $R^4$ group upon completion of the reaction; with a compound of formula 10 in the presence of a reducing agent;

and then removing any protecting groups including $P^1$, $P^2$, $P^3$, $P^4$, $P^5$, $P^6$, $P^7$, $P^8$, $P^9$, $P^{10}$, $P^{11}$, $P^{12}$, $P^{13}$, $P^{14}$, $P^{15}$, $P^{16}$ or $P^{17}$ to provide a compound of formula I; and optionally, forming a pharmaceutically acceptable salt thereof.

Generally, if a salt of one of the starting materials is used in the processes described above, such as an acid addition salt, the salt is typically neutralized before or during the reaction process. This neutralization reaction is typically accomplished by contacting the salt with one molar equivalent of a base for each molar equivalent of acid addition salt.

In process (a), i.e., the reaction between the compounds of formula 1 and 2, the leaving group represented by $X^1$ can be, for example, halo, such as chloro, bromo or iodo, or a sulfonic ester group, such as mesylate or tosylate. The groups $P^1$ and $P^2$ can be, for example, trimethylsilyl and benzyl, respectively. When the compound of formula 1 has an $R^3$ group of the formula: $—OC(O)CR^{3a}R^{3b}R^{3c}$ where $R^{3a}$ is hydroxy, the hydroxy group is optionally protected, for example, with a tert-butyldimethylsilyl group. This reaction is typically conducted in an inert diluent, such as acetonitrile, in the presence of a base. For example, this reaction can be conducted in the presence of a tertiary amine, such as diisopropylethylamine. Generally, this reaction is conducted at a temperature in the range of from 0° C. to 100° C. until the reaction is substantially complete. The reaction product is then isolated using conventional procedures, such as extraction, recrystallization, chromatography and the like.

Compounds of formula 1 are generally known in the art or can be prepared from commercially available starting materials and reagents using well-known procedures. For example, representative compounds of formula 1 can be prepared using the procedures described in U.S. Pat. Nos. 5,654,314 and 5,770,738, the disclosures of which are incorporated herein by reference in their entirety.

Compounds of formula 2 can be prepared by various procedures described herein or by procedures that are well known to those skilled in the art. For example, the hydroxy group of a compound of formula 20 below, can be readily converted into a leaving group using well-known reagents and procedures. By way of illustration, a hydroxy group can be converted into a halo group using an inorganic acid halide, such as thionyl chloride, phosphorous trichloride, phosphorous tribromide, phosphorous oxychloride and the like, or a halogen acid, such a hydrogen bromide.

In process (b), i.e., the reaction of a compound of formula 3 with a compound of formula 4, the leaving represented by $X^2$ can be, for example, halo, such as chloro, bromo or iodo, or a sulfonic ester group, such as mesylate or tosylate. The groups $P^3$, $P^4$ and $P^5$ can be, for example, benzyl, tert-butyldimethylsilyl and benzyl, respectively. This reaction is typically conducted in the presence of a base, such as sodium bicarbonate, and optionally in the presence of an alkali metal iodide, such as sodium iodide. Generally, this reaction is conducted in an inert diluent, such as tetrahydrofuran, at a temperature ranging from 25° C. to 100° C. until the reaction is substantially complete. The reaction product is then isolated using conventional procedures, such as extraction, recrystallization, chromatography and the like.

Compounds of formula 3 can be prepared by reacting a compound of formula 1 with a compound of formula 13:

$X^4—R^4—NHP^3$ 13 wherein $X^3$ represents a leaving group such as halo, such as chloro, bromo or iodo, or sulfonic ester group, such as mesylate or tosylate. This reaction is typically conducted by contacting a compound of formula 1 with a compound of formula 13 in an inert diluent, such as acetonitrile, DMF or mixtures thereof, at a temperature ranging from about 0° C. to about 100° C. until the reaction is substantially complete.

Alternatively, compounds of formula 3 can be obtained by reductive amination of a compound of formula 12. The reductive amination can be performed by reacting the compound of formula 12 with, for example, benzylamine in the presence of a reducing agent, including a borohydride reducing agent, such as sodium triacetoxyborohydride.

Compounds of formula 12 may be prepared by oxidizing the corresponding alcohol of formula 14:

14

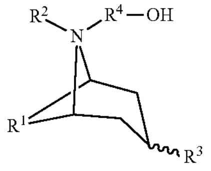

using a suitable oxidizing agent, such as sulfur trioxide pyridine complex and dimethyl sulfoxide. This oxidation reaction is typically conducted in an inert diluent, such as dichloromethane, the presence of a tertiary amine, such as diisopropylethylamine, at a temperature ranging from about −20° C. to about 25° C.

Compounds of formula 14 can be prepared by reacting a compound of formula 1 with a compound of formula 15:

$X^5—R^4—OH$ 15 wherein $X^5$ represents a leaving group such as halo, such as chloro, bromo or iodo, or a sulfonic ester group, such as mesylate or tosylate.

Compounds of formula 4 can be prepared by reacting a compound of formula 16:

16

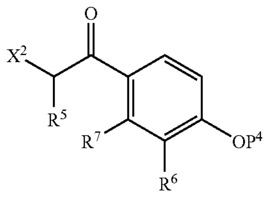

with a reducing agent, such as borane. If desired, such a reduction can be performed in the presence of a chiral catalyst to provide compounds of formula 4 in chiral form. For example, compounds of formula 16 can be reduced in the presence of a chiral catalyst formed from (R)-(+)-α,α-diphenyl-2-pyrrolidinemethanol and trimethylboroxine; or alternatively, from (S)-(−)-α,α-diphenyl-2-pyrrolidinemethanol and trimethylboroxine. The resulting hydroxy group can then be protected with a hydroxy-protecting group, $P^4$, by reaction with, for example, tert-butyldimethylsilyl trifluoromethanesulfonate.

Compounds of formula 16 in which $X^2$ represents a bromine atom can be prepared by reacting a compound of formula 17:

17

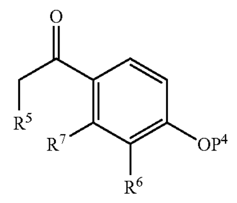

with bromine in the presence of a Lewis acid, such as boron trifluoride diethyl etherate. Compounds of formula 17 are well known in the art or can be prepared by well-known procedures using commercially available starting materials and reagents.

Referring to process (c), i.e., the reaction of a compound of formula 5 with a compound of formula 6, it will be appreciated that the groups $X^{Qa}$ and $X^{Qb}$ should be selected so as to afford the desired group Q upon completion of the reaction. For example, when the desired group Q is an amide group, i.e., —N($Q^a$)C(O)— or —C(O)N($Q^b$), one of $X^{Qa}$ and $X^{Qb}$ can be an amine group (i.e., —NH$Q^a$ or —NH$Q^b$) and the other can be a carboxyl group (i.e., —COOH) or a reactive derivative thereof (such as acyl halide, such as an acyl chloride or acyl bromide). The groups $P^6$, $P^7$ and $P^8$ can be, for example, benzyl, trimethylsilyl and benzyl, respectively. When Q is an amide group, the reaction can be performed under conventional amide coupling conditions. Similarly, when the desired group Q is a sulfonamide, i.e., —N($Q^c$)S$(O)_2$— or —S$(O)_2$N($Q^d$)-, one of $X^{Qa}$ and $X^{Qb}$ can be an amine group, —NH$Q^c$ or —NH$Q^d$ and the other can be a sulfonyl halide group (such as sulfonyl chloride or sulfonyl bromide).

Compounds of formula 5 can be prepared by reacting a compound of formula 1 with a compound of formula 18:

$$X^6—(R^{4a})_d-(A^1)_e-(R_{4b})_f—X^{Qa'} \qquad 18$$

wherein $X^6$ represents a leaving group including halo, such as chloro, bromo or iodo, and a sulfonic ester group, such as mesylate or tosylate; and $X^{Qa'}$ represents $X^{Qa}$, such as a carboxyl group or an amino group NH$Q^a$, or a protected derivative thereof, such as a (1-6C)alkoxycarbonylamino group or a tert-butoxycarbonylamino group. This reaction is typically conducted by a method analogous to that used to prepare compounds of formula 3, followed by removing any protecting group in $XQ^{a'}$.

Compounds of formula 6 can be prepared by reacting a compound of formula 4 with a compound of formula 19:

$$X^{Qb'}—(R^{4c})_g-(A^2)_h-(R^{4d})_i—N(P^6)H \qquad 19$$

wherein $X^{Qb'}$ represents $X^{Qb}$, such as a carboxyl group or an amino group NH$Q^b$, or a protected derivative thereof, such as a (1-6C)alkoxycarbonyl group or a tert-butoxycarbonylamino group. This reaction is typically conducted by a method analogous to that used to prepare compounds of formula 3, followed by removing any protecting group in $X^{Qb'}$.

Referring to process (d), i.e., the reaction of a compound of formula 3 with a compound of formula 7, any suitable reducing agent may be used in this reaction. For example, the reducing agent can be hydrogen in the presence of a Group VIII metal catalyst, such as palladium on carbon; or a metal hydride reagent, such as sodium triacetoxyborohydride. The group $P^9$ can be, for example, benzyl. This reaction is typically conducted in an inert diluent and a protic solvent, such as a mixture of dichloroethane and methanol, at a temperature in the range of from 0° C. to 100° C. until the reaction is substantially complete.

Compounds of formula 7 in the form of a hydrate can be prepared by conventional procedures, for example, by dibrominating a compound of formula 17, and then hydrolyzing the resulting dibromide to form a glyoxal or a hydrate thereof. For example, a compound of formula 17 can be reacted with hydrogen bromide and then hydrolyzed with water to form the corresponding glyoxal hydrate.

Referring to process (e), i.e., the reaction of a compound of formula 1 with a compound of formula 8, any suitable reducing agent may be used in this reaction. For example, the reducing agent may be hydrogen in the presence of a Group VIII metal catalyst, such as palladium on carbon; or a metal hydride reagent, such as sodium triacetoxyborohydride. The groups $P^{10}$, $P^{11}$ and $P^{12}$ can be, for example, trimethylsilyl, benzyl and benzyl, respectively. Typically, this reduction reaction is conducted in an inert diluent and a protic solvent, such as dichloroethane and methanol, at a temperature in the range of from 0° C. to 100° C. until the reaction is substantially complete.

Compounds of formula 8 may be prepared by oxidizing a compound of formula 20:

20

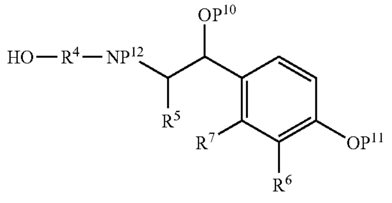

using any suitable oxidizing agent, such as sulfur trioxide pyridine complex and dimethyl sulfoxide. This reaction is typically conducted in the presence of a tertiary amine, such as diisopropylethylamine, at a temperature in the range of from about −20° C. to about 25° C. until the oxidation is substantially complete.

Compounds of formula 20 can be prepared by reacting a compound of formula 10 with a compound of formula 21:

$$HO—R^4—X^8 \qquad 21$$

wherein $X^8$ represents a leaving group including halo, such as chloro, bromo or iodo, and a sulfonic ester group, such as mesylate or tosylate.

Referring to process (f), i.e., the reaction of a compound of formula 9 with a compound of formula 10, the leaving group represented by $X^3$ can be, for example, halo, such as chloro, bromo or iodo, or a sulfonic ester group, such as mesylate or tosylate. The groups $P^{13}$, $P^{14}$ and $P^{15}$ can be, for example, trimethylsilyl, benzyl and benzyl, respectively. This reaction is typically conducted an inert diluent, such as acetonitrile, in the presence of a suitable base. For example, this reaction can be conducted in the presence of a tertiary amine, such as diisopropylethylamine. Generally, this reaction is conducted at a temperature in the range of from 0° C. to 100° C. until the reaction is substantially complete.

Compounds of formula 9 can be prepared by steps analogous to those of methods (a) to (e) herein, starting from a compound of formula 1. Additionally, compounds of formula 10 can be prepared from compounds of formula 4 by reaction with an amine of formula $P^{15}NH_2$.

Referring to process (g), representative examples for $P^{16}$ and $P^{17}$ are benzyl or tert-butyldimethylsilyl. This reduction reaction can be conducted using any suitable reducing agent including borohydrides, such as sodium borohydride. Any suitable solvent or diluent may be employed, such as N,N-dimethylformamide. This reaction is typically conducted at a temperature in the range of from 0° C. to 100° C. until the reaction is substantially complete.

Compounds of formula 11 can be prepared by reacting a compound of formula 3 with a compound of formula 16. This reaction is conveniently performed in the presence of a base, such as potassium carbonate.

Referring to process (h), i.e., the reaction of a compound of formula 12 with a compound of formula 10, any suitable reducing agent may be used in this reaction. For example, the reducing agent may be hydrogen in the presence of a Group VIII metal catalyst, such as palladium on carbon; or a metal hydride reagent, such as sodium triacetoxyborohydride. The groups $P^{13}$, $P^{14}$ and $P^{15}$ can be, for example, tert-butyldimethylsilyl, benzyl and benzyl, respectively. Typically, this reduction reaction is conducted in an inert diluent and a protic solvent, such as dichloroethane and methanol, at a temperature in the range of from 0° C. to 100° C. until the reaction is substantially complete.

Compounds of formula 14 are readily prepared by oxidation of the corresponding alcohol or by hydrolysis of the corresponding acetal. Any suitable oxidizing agent may be employed in this reaction to provide the aldehyde, such as sulfur trioxide pyridine complex and dimethyl sulfoxide. The acetal may be hydrolyzed under conventional conditions using aqueous acid to provide the aldehyde.

Additionally, compounds of formula I in which $R^6$ and $R^7$ together form $—NR^{7g}C(O)—CR^{7h}R^{7i}—CR^{7j}R^{7k}—$ or $—CR^{7l}R^{7m}—CR^{7n}R^{7o}—C(O)—NR^{7p}—$ may be prepared by reducing a corresponding compound of formula I in which $R^6$ and $R^7$ together form $—NR^{7a}C(O)—CR^{7b}{=}CR^{7c}—$ or $—CR^{7d}{=}CR^{7e}—C(O)—NR^{7f}—$, for example by catalytic hydrogenation.

Further details regarding specific reaction conditions and other procedures for preparing representative compounds of this invention or intermediates thereof are described in the Examples set forth below.

Pharmaceutical Compositions and Formulations

The compounds of this invention are typically administered to a patient in the form of a pharmaceutical composition or formulation. Such pharmaceutical compositions may be administered to the patient by any acceptable route of administration including, but not limited to, inhaled, oral, nasal, topical (including transdermal) and parenteral modes of administration. It will be understood that any form of the compounds of this invention, (i.e., free base, pharmaceutically acceptable salt, solvate, etc.) that is suitable for the particular mode of administration can be used in the pharmaceutical compositions discussed herein.

Accordingly, in one of its compositions aspects, this invention is directed to a pharmaceutical composition comprising a pharmaceutically acceptable carrier or excipient and a therapeutically effective amount of a compound of formula I, or a pharmaceutically acceptable salt thereof. Optionally, such pharmaceutical compositions may contain other therapeutic and/or formulating agents if desired.

The pharmaceutical compositions of this invention typically contain a therapeutically effective amount of a compound of the present invention or a pharmaceutically acceptable salt thereof. Typically, such pharmaceutical compositions will contain from about 0.01 to about 95% by weight of the active agent; including, from about 0.01 to about 30% by weight; such as from about 0.01 to about 10% by weight of the active agent.

Any conventional carrier or excipient may be used in the pharmaceutical compositions of this invention. The choice of a particular carrier or excipient, or combinations of carriers or exipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in *Remington: The Science and Practice of Pharmacy,* $20^{th}$ Edition, Lippincott Williams & White, Baltimore, Md. (2000); and H. C. Ansel et al., *Pharmaceutical Dosage Forms and Drug Delivery Systems,* $7^{th}$ Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) compressed propellant gases, such as chlorofluorocarbons and hydrofluorocarbons; and (22) other non-toxic compatible substances employed in pharmaceutical compositions.

The pharmaceutical compositions of this invention are typically prepared by thoroughly and intimately mixing or blending a compound of the invention with a pharmaceutically acceptable carrier and one or more optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical compositions of this invention are suitable for inhaled administration. Suitable pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI) or a similar delivery device.

In a specific embodiment of this invention, the pharmaceutical composition comprising the active agent is administered by inhalation using a nebulizer inhaler. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the active agent is typically dissolved in a suitable carrier to form a solution. Alternatively, the active agent can be micronized and combined with a suitable carrier to form a suspension of micronized particles of respirable size, where micronized is typically defined as having about 90% or more of the particles with a diameter of less than about 10 μm. Suitable nebulizer devices are provided commercially, for example, by PARI GmbH (Starnberg, German). Other nebulizer devices include Respimat (Boehringer Ingelheim) and those disclosed, for example, in U.S. Pat. No. 6,123,068 and WO 97/12687.

A representative pharmaceutical composition for use in a nebulizer inhaler comprises an isotonic aqueous solution comprising from about 0.05 μg/mL to about 10 mg/mL of a compound of formula I or a pharmaceutically acceptable salt or solvate or stereoisomer thereof.

In another specific embodiment of this invention, the pharmaceutical composition comprising the active agent is administered by inhalation using a dry powder inhaler. Such dry powder inhalers typically administer the active agent as a free-flowing powder that is dispersed in a patient's air-stream during inspiration. In order to achieve a free flowing powder, the active agent is typically formulated with a suitable excipient such as lactose or starch.

A representative pharmaceutical composition for use in a dry powder inhaler comprises dry lactose having a particle size between about 1 μm and about 100 μm and micronized particles of a compound of formula I, or a pharmaceutically acceptable salt or solvate or stereoisomer thereof.

Such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device.

Examples of dry powder inhaler delivery devices include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); Rotahaler (GlaxoSmithKline) (see, e.g., U.S. Pat. No. 4,353,365) and Handihaler (Boehringer Ingelheim). Further examples of suitable DPI devices are described in U.S. Pat. Nos. 5,415,162, 5,239,993, and 5,715,810 and references cited therein.

In yet another specific embodiment of this invention, the pharmaceutical composition comprising the active agent is administered by inhalation using a metered-dose inhaler. Such metered-dose inhalers typically discharge a measured amount of the active agent or a pharmaceutically acceptable salt thereof using compressed propellant gas. Accordingly, pharmaceutical compositions administered using a metered-dose inhaler typically comprise a solution or suspension of the active agent in a liquefied propellant. Any suitable liquefied propellant may be employed including chlorofluorocarbons, such as $CCl_3F$, and hydrofluoroalkanes (HFAs), such as 1,1,1,2-tetrafluoroethane (HFA 134a) and 1,1,1,2,3,3,3-heptafluoro-n-propane, (HFA 227). Due to concerns about chlorofluorocarbons affecting the ozone layer, formulations containing HFAs are generally preferred. Additional optional components of HFA formulations include co-solvents, such as ethanol or pentane, and surfactants, such as sorbitan trioleate, oleic acid, lecithin, and glycerin. See, for example, U.S. Pat. No. 5,225,183, EP 0717987 A2, and WO 92/22286.

A representative pharmaceutical composition for use in a metered-dose inhaler comprises from about 0.01% to about 5% by weight of a compound of formula I, or a pharmaceutically acceptable salt or solvate or stereoisomer thereof; from about 0% to about 20% by weight ethanol; and from about 0% to about 5% by weight surfactant; with the remainder being an HFA propellant.

Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of a metered-dose inhaler device. Examples of metered-dose inhaler devices developed specifically for use with HFA propellants are provided in U.S. Pat. Nos. 6,006,745 and 6,143,277. Alternatively, a suspension formulation can be prepared by spray drying a coating of surfactant on micronized particles of the active agent. See, for example, WO 99/53901 and WO 00/61108.

For additional examples of processes of preparing respirable particles, and formulations and devices suitable for inhalation dosing see U.S. Pat. Nos. 6,268,533, 5,983,956, 5,874,063, and 6,221,398, and WO 99/55319 and WO 00/30614.

In another embodiment, the pharmaceutical compositions of this invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of this invention will typically comprise a compound of the present invention as the active ingredient and one or more pharmaceutically acceptable carriers, such as sodium citrate or dicalcium phosphate. Optionally or alternatively, such solid dosage forms may also comprise: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of this invention. Examples of pharmaceutically acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of this invention are preferably packaged in a unit dosage form. The term "unit dosage form" means a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

The compounds of this invention can also be administered transdermally using known transdermal delivery systems and excipents. For example, a compound of this invention can be admixed with permeation enhancers, such as propylene glycol, polyethylene glycolm monolaurate, azacycloalkan-2-ones and the like, and incorporated into a patch or similar delivery system. Additional excipients including gelling agents, emulsifiers and buffers, may be used in such transdermal compositions if desired.

The pharmaceutical compositions of this invention may also contain other therapeutic agents that are co-administered with a compound of formula I, or pharmaceutically acceptable salt or solvate or stereoisomer thereof. For example, the pharmaceutical compositions of this invention may further comprise one or more therapeutic agents selected from other bronchodilators (e.g., $PDE_3$ inhibitors, adenosine 2b modulators and $\beta_2$ adrenergic receptor agonists); anti-inflammatory agents (e.g. steroidal anti-inflammatory agents, such as corticosteroids; non-steroidal anti-inflammatory agents (NSAIDs), and $PDE_4$ inhibitors); other muscarinic receptor antagonists (i.e., antichlolinergic agents); antiinfective agents (e.g. Gram positive and Gram negative antibiotics or antivirals); antihistamines; protease inhibitors; and afferent blockers (e.g., $D_2$ agonists and neurokinin modulators). The other therapeutic agents can be used in the form of pharmaceutically acceptable salts or solvates. Additionally, if appropriate, the other therapeutic agents can be used as optically pure stereoisomers.

Representative $\beta_2$ adrenergic receptor agonists that can be used in combination with, and in addition to, the compounds of this invention include, but are not limited to, salmeterol, salbutamol, formoterol, salmefamol, fenoterol, terbutaline, albuterol, isoetharine, metaproterenol, bitolterol, pirbuterol, levalbuterol and the like, or pharmaceutically acceptable salts thereof. Other $\beta_2$ adrenergic receptor agonists that can be used in combination with the compounds of this invention include, but are not limited to, 3-(4-{[6-({(2R)-2-hydroxy-2-[4-hydroxy-3-(hydroxymethyl)-phenyl]ethyl}amino)-hexyl]oxy}butyl)benzenesulfonamide and 3-(-3-{[7-({(2R)-2-hydroxy-2-[4-hydroxy-3-(hydroxymethyl)phenyl]ethyl}-amino)heptyl]oxy}-propyl)benzenesulfonamide and related compounds disclosed in WO 02/066422, published on Aug. 29, 2002; 3-[3-(4-{[6-([(2R)-2-hydroxy-2-[4-hydroxy-3-(hydroxymethyl)phenyl]ethyl}amino)hexyl]oxy}butyl)-phenyl]imidazolidine-2,4-dione and related compounds disclosed in WO 02/070490, published Sep. 12, 2002; 3-(4-{[6-({(2R)-2-[3-(formylamino)-4-hydroxyphenyl]-2-hydroxyethyl}amino)hexyl]oxy}butyl)-benzenesulfonamide, 3-(4-{[6-({(2S)-2-[3-(formylamino)-4-hydroxyphenyl]-2-hydroxyethyl}amino)hexyl]oxy}butyl)-benzenesulfonamide, 3-(4-{[6-({(2R/S)-2-[3-(formylamino)-4-hydroxyphenyl]-2-hydroxyethyl}amino)hexyl]oxy}butyl)-benzenesulfonamide, N-(tert-butyl)-3-(4-{[6-({(2R)-2-[3-(formylamino)-4-hydroxyphenyl]-2-hydroxyethyl}amino)hexyl]-oxy}butyl) benzenesulfonamide, N-(tert-butyl)-3-(4-{[6-({(2S)-2-[3-(formylamino)-4-hydroxyphenyl]-2-hydroxyethyl}amino)-hexyl]oxy}butyl)-benzenesulfonamide, N-(tert-butyl)-3-(4-{[6-({(2R/S)-2-[3-(formylamino)-4-hydroxyphenyl]-2-hydroxyethyl}amino)hexyl]-oxy}butyl) benzenesulfonamide and related compounds disclosed in WO 02/076933, published on Oct. 3, 2002; 4-{(1R)-2-[(6-{2-[(2,6-dichlorobenzyl)oxy]ethoxy}hexyl)amino]-1-hydroxyethyl}-2-(hydroxymethyl)phenol and related compounds disclosed in WO 03/024439, published on Mar. 27, 2003; N-{2-[4-((R)-2-hydroxy-2-phenylethylamino)phenyl]ethyl}-(R)-2-hydroxy-2-(3-formamido-4-hydroxyphenyl) ethylamine and related compounds disclosed in U.S. Pat. No. 6,576,793 B1, issued on Jun. 10, 2003; N-{2-[4-(3-phenyl-4-methoxyphenyl)aminophenyl]ethyl}-(R)-2-hydroxy-2-(8-hydroxy-2(1H)-quinolinon-5-yl)ethylamine and related compounds disclosed in U.S. Pat. No. 6,653,323 B2, issued on Nov. 25, 2003; and pharmaceutically acceptable salts thereof. When employed, the $\beta_2$-adrenoreceptor agonist will be present in the pharmaceutical composition in a therapeutically effective amount. Typically, the $\beta_2$-adrenoreceptor agonist will be present in an amount sufficient to provide from about 0.05 μg to about 500 μg per dose.

Representative steroidal anti-inflammatory agents that can be used in combination with the compounds of this invention include, but are not limited to, methyl prednisolone, prednisolone, dexamethasone, fluticasone propionate, 6,9-difluoro-17-[(2-furanylcarbonyl)oxy]-11-hydroxy-16-methyl-3-oxoandrosta-1,4-diene-17-carbothioic acid S-fluoromethyl ester, 6,9-difluoro-11-hydroxy-16-methyl-3-oxo-17-propionyloxy-androsta-1,4-diene-17-carbothioic acid S-(2-oxo-tetrahydrofuran-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, ST-126 and the like, or pharmaceutically-acceptable salts thereof. When employed, the steroidal anti-inflammatory agent will be present in the pharmaceutical composition in a therapeutically effective amount. Typically, the steroidal anti-inflammatory agent will be present in an amount sufficient to provide from about 0.05 μg to about 500 μg per dose.

Other suitable combinations include, for example, other anti-inflammatory agents, e.g., NSAIDs (such as sodium cromoglycate; nedocromil sodium; phosphodiesterase (PDE) inhibitors (e.g. theophylline, PDE4 inhibitors or mixed PDE3/PDE4 inhibitors); leukotriene antagonists (e.g. monteleukast); inhibitors of leukotriene synthesis; iNOS inhibitors; protease inhibitors, such as tryptase and elastase inhibitors; beta-2 integrin antagonists and adenosine receptor agonists or antagonists (e.g. adenosine 2a agonists); cytokine antagonists (e.g. chemokine antagonists such as, an interleukin antibody (IL antibody), specifically, an IL-4 therapy, an IL-13 therapy, or a combination thereof); or inhibitors of cytokine synthesis.

For example, representative phosphodiesterase-4 (PDE4) inhibitors or mixed PDE3/PDE4 inhibitors that can be used in combination with the compounds of this invention include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl) cyclohexan-1-ol]; cis-4-cyano-4-[3-(cyclopentyloxy)-4-methoxyphenyl]cyclohexane-1-carboxylic acid and the like, or pharmaceutically acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds disclosed in WO99/16766 (Kyowa Hakko); K-34 (Kyowa Hakko); V-11294A (Napp); roflumilast (Byk-Gulden); pthalazinone compounds disclosed in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

Representative muscarinic antagonists (i.e., anticholinergic agents) that can be used in combination with, and in addition to, the compounds of this invention include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like, or a pharmaceutically acceptable salt thereof; or, for those compounds listed as a salt, alternate pharmaceutically acceptable salt thereof.

Representative antihistamines (i.e., $H_1$-receptor antagonists) that can be used in combination with the compounds of this invention include, but are not limited to, ethanolamines, such as carbinoxamine maleate, clemastine fumarate, diphenylhydramine hydrochloride and dimenhydrinate; ethylenediamines, such as pyrilamine amleate, tripelennamine hydrochloride and tripelennamine citrate; alkylamines, such as chlorpheniramine and acrivastine; piperazines, such as hydroxyzine hydrochloride, hydroxyzine pamoate, cyclizine hydrochloride, cyclizine lactate, meclizine hydrochloride and cetirizine hydrochloride; piperidines, such as astemizole, levocabastine hydrochloride, loratadine or its descarboethoxy analogue, terfenadine and fexofenadine hydrochloride; azelastine hydrochloride; and the like, or a pharmaceutically acceptable salt thereof; or, for those compounds listed as a salt, alternate pharmaceutically acceptable salt thereof.

Suitable doses for the other therapeutic agents administered in combination with a compound of the invention are in the range of about 0.05 μg/day to about 100 mg/day.

The following formulations illustrate representative pharmaceutical compositions of the present invention:

Formulation Example A

A dry powder for administration by inhalation is prepared as follows:

| Ingredients | Amount |
|---|---|
| Compound of the invention | 0.2 mg |
| Lactose | 25 mg |

Representative Procedure: The compound of the invention is micronized and then blended with lactose. This blended mixture is then loaded into a gelatin inhalation cartridge. The contents of the cartridge are administered using a powder inhaler.

Formulation Example B

A dry powder formulation for use in a dry powder inhalation device is prepared as follows:

Representative Procedure: A pharmaceutical composition is prepared having a bulk formulation ratio of micronized compound of the invention to lactose of 1:200. The composition is packed into a dry powder inhalation device capable of delivering between about 10 μg and about 100 μg of the compound of the invention per dose.

Formulation Example C

A dry powder for administration by inhalation in a metered dose inhaler is prepared as follows:

Representative Procedure: A suspension containing 5 wt. % of a compound of the invention and 0.1 wt. % lecithin is prepared by dispersing 10 g of the compound of the invention as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into cartridges with pressurized 1,1,1,2-tetrafluoroethane.

Formulation Example D

A pharmaceutical composition for use in a metered dose inhaler is prepared as follows:

Representative Procedure: A suspension containing 5% compound of the invention, 0.5% lecithin, and 0.5% trehalose is prepared by dispersing 5 g of active ingredient as micronized particles with mean size less than 10 m in a colloidal solution formed from 0.5 g of trehalose and 0.5 g of lecithin dissolved in 100 mL of demineralized water. The suspension is spray dried and the resulting material is micronized to particles having a mean diameter less than 1.5 μm. The particles are loaded into canisters with pressurized 1,1,1,2-tetrafluoroethane.

Formulation Example E

A pharmaceutical composition for use in a nebulizer inhaler is prepared as follows:

Representative Procedure: An aqueous aerosol formulation for use in a nebulizer is prepared by dissolving 0.1 mg of the compound of the invention in 1 mL of a 0.9% sodium chloride solution acidified with citric acid. The mixture is stirred and sonicated until the active ingredient is dissolved. The pH of the solution is adjusted to a value in the range of from 3 to 8 by the slow addition of NaOH.

Formulation Example F

Hard gelatin capsules for oral administration are prepared as follows:

| Ingredients | Amount |
|---|---|
| Compound of the invention | 250 mg |
| Lactose (spray-dried) | 200 mg |
| Magnesium stearate | 10 mg |

Representative Procedure: The ingredients are thoroughly blended and then loaded into a hard gelatin capsule (460 mg of composition per capsule).

Formulation Example G

A suspension for oral administration is prepared as follows:

| Ingredients | Amount |
|---|---|
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure: The ingredients are mixed to form a suspension containing 100 mg of active ingredient per 10 mL of suspension.

Formulation Example H

An injectable formulation is prepared as follows:

| Ingredients | Amount |
|---|---|
| Compound of the invention | 0.2 g |
| Sodium acetate buffer solution (0.4 M) | 2.0 mL |
| HCl (0.5 N) or NaOH (0.5 N) | q.s. to pH 4 |
| Water (distilled, sterile) | q.s. to 20 mL |

Representative Procedure: The above ingredients are blended and the pH is adjusted to 4±0.5 using 0.5 N HCl or 0.5 N NaOH.

Utility

The compounds of this invention possess both $\beta_2$ adrenergic receptor agonist and muscarinic receptor antagonist activity and therefore, such compounds are useful for treating medical conditions mediated by $\beta_2$ adrenergic receptors or muscarinic receptors, i.e., medical conditions that are ameliorated by treatment with a $\beta_2$ adrenergic receptor agonist or a muscarinic receptor antagonist. Such medical conditions include, by way of example, pulmonary disorders or diseases including those associated with reversible airway obstruction, such as chronic obstructive pulmonary disease (e.g., chronic and wheezy bronchitis and emphysema), asthma, pulmonary fibrosis, allergic rhinitis, rhinorrhea and the like. Other conditions which may be treated include premature labor, depression, congestive heart failure, skin diseases (e.g., inflammatory, allergic, psoriatic and proliferative skin diseases, conditions where lowering peptic acidity is desirable (e.g., peptic and gastric ulceration) and muscle wasting disease.

Accordingly, in one embodiment, this invention is directed to a method for treating a pulmonary disorder, the method comprising administering to a patient in need of treatment a therapeutically effective amount of a compound of formula I or a pharmaceutically acceptable salt or solvate or stereoisomer thereof. When used to treat a pulmonary disorder, the compounds of this invention will typically be administered by inhalation in multiple doses per day, in a single daily dose or a single weekly dose. Generally, the dose for treating a pulmonary disorder will range from about 10 μg/day to about 200 μg/day.

When administered by inhalation, the compounds of this invention typically have the effect of providing bronchodilation. Accordingly, in another of its method aspects, this invention is directed to a method of providing bronchodilation in a patient, the method comprising administering to a patient requiring bronchodilation a therapeutically effective amount of a compound of formula I or a pharmaceutically acceptable salt or solvate or stereoisomer thereof. Generally, the dose for providing bronchodilation will range from about 10 μg/day to about 200 μg/day.

In one embodiment, this invention is directed to a method of treating chronic obstructive pulmonary disease or asthma, the method comprising administering to a patient in need of treatment a therapeutically effective amount of a compound of formula I or a pharmaceutically acceptable salt or solvate or stereoisomer thereof. When used to treat a COPD or asthma, the compounds of this invention will typically be administered by inhalation in multiple doses per day or in a single daily dose. Generally, the dose for treating COPD or asthma will range from about 10 μg/day to about 200 μg/day.

As used herein, COPD includes chronic obstructive bronchitis and emphysema (see, for example, Barnes, Chronic Obstructive Pulmonary Disease, *N Engl J Med* 2000: 343: 269-78).

When used to treat a pulmonary disorder, the compounds of this invention are optionally administered in combination with other therapeutic agents. In particular, by combining the compounds of this invention with a steroidal anti-inflammatory agent (e.g. a corticosteroid), the pharmaceutical compositions of this invention can provide triple therapy, i.e., $\beta_2$ adrenergic receptor agonist, muscarinic receptor antagonist and anti-inflammatory activity, using only two active components. Since pharmaceutical compositions containing two active components are typically easier to formulate compared to compositions containing three active components, such two component compositions provide a significant advantage over compositions containing three active components.

Accordingly, in a particular embodiment, the pharmaceutical compositions and methods of this invention further comprise a therapeutically effective amount of a steroidal anti-inflammatory agent.

Compounds of this invention exhibit both muscarinic receptor antagonist and $\beta_2$ adrenergic receptor agonist activity. Accordingly, among other properties, compounds of particular interest are those that demonstrate an inhibitory constant $K_i$ value for binding at the $M_3$ muscarinic receptor and an $EC_{50}$ value for $\beta_2$ adrenergic receptor agonist activity of less than about 100 nM; particularly less than 10 nM. Among these compounds, compounds of special interest include those having muscarinic activity, expressed in terms of the inhibitory constant $K_i$ for binding at the $M_3$ muscarinic receptor, that is about equal to the compound's $\beta_2$ adrenergic agonist activity, expressed in terms of the half maximal effective concentration $EC_{50}$, as determined in the in vitro assays described herein, or in similar assays. For example, compounds of particular interest are those having a ratio of the inhibitory constant $K_i$ for the $M_3$ muscarinic receptor to the $EC_{50}$ for the $\beta_2$ adrenergic receptor ranging from about 30:1 to about 1:30; including about 20:1 to about 1:20; such as about 10:1 to about 1:10.

In one of its method aspects, the present invention also provides a method for treating a pulmonary disorder, the method comprising administering to a patient in need of treatment a therapeutically effective amount of a compound having both muscarinic receptor antagonist and $\beta_2$ adrenergic receptor agonist activity. In a particular embodiment of this method, the compound administered has an inhibitory constant $K_i$ for the $M_3$ muscarinic receptor that is less than about 100 nM and a half maximal effective concentration $EC_{50}$ for agonism at the $\beta_2$ adrenergic receptor that is less than about 100 nM. In another embodiment, the method for treating a pulmonary disorder comprises administering a therapeutically effective amount of a compound for which the ratio of the inhibitory constant $K_i$ for the $M_3$ muscarinic receptor to the $EC_{50}$ for agonism of the $\beta_2$ adrenergic receptor is between about 30:1 and about 1:30.

Since compounds of this invention possess both $\beta_2$ adrenergic agonist activity and muscarinic receptor antagonist activity, such compounds are also useful as research tools for investigating or studying biological systems or samples having $\beta_2$ adrenergic receptors or muscarinic receptors, or for discovering new compounds having both $\beta_2$ adrenergic agonist activity and muscarinic receptor antagonist activity. Such biological systems or samples may comprise $\beta_2$ adrenergic receptors and/or muscarinic receptors. Any suitable biological system or sample having $\beta_2$ adrenergic and/or muscarinic receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.), and the like.

In this embodiment, a biological system or sample comprising a $\beta_2$ adrenergic receptor or a muscarinic receptor is contacted with a $\beta_2$ adrenergic receptor-agonizing or muscarinic receptor-antagonizing amount of a compound of this invention. The effects are then determined using conventional procedures and equipment, such as radioligand binding assays and functional assays. Such functional assays include ligand-mediated changes in intracellular cyclic adenosine monophosphate (cAMP), ligand-mediated changes in activity of the enzyme adenylyl cyclase (which synthesizes cAMP), ligand-mediated changes in incorporation of guanosine 5'-O-(-thio)triphosphate ($[^{35}S]$GTP S) into isolated membranes via receptor catalyzed exchange of $[^{35}S]$GTP S for GDP, ligand-mediated changes in free intracellular calcium ions (measured, for example, with a fluorescence-linked imaging plate reader or FLIPR® from Molecular Devices, Inc.). A compound of this invention will agonize or cause activation of a $\beta_2$ adrenergic receptor and antagonize or decrease the activation of muscarinic receptors in any of the functional assays listed above, or assays of a similar nature. The amount of compound used in these studies will typically range from about 0.1 nanomolar to about 100 nanomolar.

Additionally, the compounds of this invention can be used as research tools for discovering new compounds that have both a $\beta_2$ adrenergic receptor agonist and muscarinic receptor antagonist activity. In this embodiment, a $\beta_2$ adrenergic receptor and muscarinic receptor binding data (for example, as determined by in vitro radioligand displacement assays) for a test compound or a group of test compounds is compared to the $\beta_2$ adrenergic receptor and muscarinic receptor binding data for a compound of this invention to identify those test compounds that have about equal or superior $\beta_2$ adrenergic receptor and/or muscarinic receptor binding, if any. This aspect of the invention includes, as separate embodiments, both the generation of comparison data (using the appropriate assays) and the analysis of the test data to identify test compounds of interest.

In some cases, compounds of this invention may possess either weak muscarinic receptor antagonist activity or weak $\beta_2$ adrenergic receptor agonist activity. In these cases, those of ordinary skill in the art will recognize that such compounds still have utility as primarily either a $\beta_2$ adrenergic receptor agonist or a muscarinic receptor antagonist, respectively.

The properties and utility of the compounds of this invention can be demonstrated using various in vitro and in vivo assays well-known to those skilled in the art. For example, representative assays are described in further detail in the following Examples.

EXAMPLES

The following Preparations and Examples are provided to illustrate specific embodiments of this invention. These specific embodiments, however, are not intended to limit the scope of this invention in any way unless specifically indicated.

The following abbreviations have the following meanings unless otherwise indicated and any other abbreviations used herein and not defined have their standard meaning:

| | |
|---|---|
| AC | adenylyl cyclase |
| Ach | acetylcholine |
| ATCC | American Type Culture Collection |
| BSA | bovine serum albumin |
| cAMP | 3'-5' cyclic adenosine monophosphate |
| CHO | Chinese hamster ovary |
| $cM_5$ | cloned chimpanzee $M_5$ receptor |
| DCM | dichloromethane (i.e., methylene chloride) |
| DIBAL-H | diisobutylaluminum hydride |
| DIPEA | N,N-diisopropylethylamine |
| dPBS | Dulbecco's phosphate buffered saline |
| DMEM | Dulbecco's Modified Eagle's Medium |
| DMSO | dimethyl sulfoxide |
| EDTA | ethylenediaminetetraacetic acid |
| Emax | maximal efficacy |
| EtOAc | ethyl acetate |
| EtOH | ethanol |
| FBS | fetal bovine serum |
| FLIPR | fluorometric imaging plate reader |
| Gly | glycine |
| HATU | O-(7-azabenzotriazol-1-yl-N,N,N',N'-tetramethyluronium hexafluorophosphate |

-continued

| | |
|---|---|
| HBSS | Hank's buffered salt solution |
| HEK | human embryonic kidney cells |
| HEPES | 4-(2-hydroxyethyl)-1-piperazineethanesulfonic acid |
| $hM_1$ | cloned human $M_1$ receptor |
| $hM_2$ | cloned human $M_2$ receptor |
| $hM_3$ | cloned human $M_3$ receptor |
| $hM_4$ | cloned human $M_4$ receptor |
| $hM_5$ | cloned human $M_5$ receptor |
| HPLC | high-performance liquid chromatography |
| IBMX | 3-isobutyl-1-methylxanthine |
| %Eff | % efficacy |
| PBS | phosphate buffered saline |
| PyBOP | benzotriazol-1-yloxytripyrrolidinophosphonium hexafluorophosphate |
| rpm | rotations per minute |
| TFA | trifluoroacetic acid |
| THF | tetrahydrofuran |
| Tris | tris(hydroxymethyl)aminomethane |

Unless noted otherwise, reagents, starting materials and solvents were purchased from commercial suppliers (such as Aldrich, Fluka, Sigma and the like) and were typically used without further purification.

Liquid chromatography mass spectrometry (LCMS) data were obtained with an Applied Biosystems (Foster City, Calif.) model API-150EX instrument.

Small-scale purification was conducted using an API 150EX Prep Workstation system from Applied Biosystems. The mobile phase was A: water+0.05% v/v TFA; and B: acetonitrile+0.05% v/v TFA. For arrays (typically about 3 to 50 mg recovered sample size) the following conditions were used: 20 mL/min flow rate; 15 min gradients and a 20 mm×50 mm Prism RP column with 5 micron particles (Thermo Hypersil-Keystone, Bellefonte, Pa.). For larger scale purifications (typically greater than 100 mg crude sample), the following conditions were used: 60 mL/min flow rate; 30 min gradients and a 41.4 mm×250 mm Microsorb BDS column with 10 micron particles (Varian, Palo Alto, Calif.).

The specific rotation for chiral compounds (indicated as $[\alpha]^{20}_D$) was measured using a Jasco Polarimeter (Model P-1010) with a tungsten halogen light source and a 589 nm filter at 20° C. Samples of test compounds were typically measured at 1 mg/mL water.

Preparation 1

Hydroxydithien-2-ylacetic Acid 9-Methyl-3-oxa-9-azatricyclo[3.3.1.0$^{2,4}$]non-7-yl Ester

(a) Hydroxydithien-2-ylacetic Acid Methyl Ester

2-Bromothiophene (9.68 mL, 0.1 mol) was slowly added to a stirred mixture of magnesium turnings (2.7 g, 0.11 mol) in diethyl ether (100 mL) under a nitrogen atmosphere at 0° C. The reaction mixture was stirred at 35° C. for 3 h and then dimethyl oxalate (5.9 g, 0.05 mol) in diethyl ether (150 mL) was added dropwise. The reaction mixture was heated at reflux (45° C.) for 45 min and then the mixture was allowed to cool to ambient temperature and 1.25 M sulfuric acid (150 mL) was added. The reaction mixture was stirred at ambient temperature for 1 h and then the organic layer was separated and washed with dilute aqueous sodium bicarbonate solution (100 mL), water (100 mL), dried with sodium sulfate, filtered and concentrated under reduced pressure. The resulting solid residue was recrystallized from tetrachloromethane (~1 g/3 mL) to yield the title compound (7.68 g, 30 mmol, 60%).

(b) 9-Methyl-3-oxa-9-azatricyclo[3.3.1.0$^{2,4}$]nonan-7-ol

Sodium borohydride (39.0 g, 1.03 mol) was added portion-wise to a stirred suspension of scopolamine (75 g, 171 mmol) in ethanol (743 mL), at 0° C. under a nitrogen atmosphere and the reaction mixture was stirred at ambient temperature for 24 h. The mixture was then acidified with 2M hydrochloric acid in diethyl ether (600 mL) and stirred for another 24 h at ambient temperature. The reaction mixture was filtered and the resulting solid was washed with diethyl ether. The dried solid was dissolved in the minimum amount of 10% aqueous potassium carbonate solution and extracted with trichloromethane (6×150 mL). The combined organic extracts were dried (magnesium sulfate), filtered and the solvent was removed under reduced pressure to give the title compound as crystals (13.2 g, 85.5 mmol, 50%).

(c) Hydroxydithien-2-ylacetic Acid 9-Methyl-3-oxa-9-aza-tricyclo[3.3.1.0$^{2,4}$]non-7-yl Ester The product of step (b) (2.00 g, 12.9 mmol) and the product of step (a) (3.61 g, 14.2 mmol) were melted together at 70° C., under a vacuum of 210 Torr for 1 h. Sodium hydride (60% suspension in oil, 620 mg, 15.5 mmol) was added and the reaction mixture was stirred at 70° C. under 210 Torr for 3 h. The reaction mixture was allowed to cool to ambient temperature and then water (30 mL) and dichloromethane (30 mL) were added. The organic layer was separated and washed with water (2×20 mL), dried (magnesium sulfate), filtered and the solvent was removed under reduced pressure. The resulting residue was purified by flash chromatography (5% MeOH/DCM) to give the title compound as a solid (2.03 g, 5.4 mmol, 42%).

Preparation 2

9-(9-Bromononyl)-7-(2-hydroxy-2,2-dithiophen-2-ylacetoxy)-9-methyl-3-oxa-9-azoniatricyclo[3.3.1.0$^{2,4}$]nonane Bromide 1,9-Dibromononane (610 μL, 3 mmol) was added to a stirred solution of the product of Preparation 1 (377 mg, 1 mmol) and DIPEA (1.05 mL, 6 mmol) in DMF (5 mL) at 50° C. The reaction mixture was heated at 80° C. for 72 h and then the solvent was removed under reduced pressure. The crude residue was purified by flash chromatography (10% MeOH in DCM containing 0.5% $NH_4OH$) to give the title compound (292 mg, 0.5 mmol, 50%).

Preparation 3

8-Benzyloxy-5-(2-bromoacetyl)-1H-quinolin-2-one

(a) 8-Acetoxy-1H-quinolin-2-one

8-Hydroxyquinoline-N-oxide (160.0 g, 1.0 mol), commercially-available from Aldrich, Milwaukee, Wis., and acetic anhydride (800 mL, 8.4 mol) were heated at 100° C. for 3 h and then cooled in ice. The product was collected on a Buchner funnel, washed with acetic anhydride (2×100 mL) and dried under reduced pressure to give 8-acetoxy-1H-quinolin-2-one (144 g) as a solid.

(b) 5-Acetyl-8-hydroxy-1H-quinolin-2-one

A slurry of aluminum chloride (85.7 g, 640 mmol) in 1,2-dichloroethane (280 mL) was cooled in ice, and the product from step (a) (56.8 g, 280 mmol) was added. The mixture was warmed to room temperature and then heated at 85° C. After 30 min, acetyl chloride (1.5 mL, 21 mmol) was added and the mixture was heated an additional 60 min. The reaction mixture was then cooled and added to 1N hydrochloric acid (3 L) at 0° C. with good stirring. After stirring for 2 h, the solids were collected on a Buchner funnel, washed with water (3×250 mL) and dried under reduced pressure. The crude product isolated from several batches (135 g) was combined and triturated with dichloromethane (4 L) for 6 h. The resulting solid was collected on a Buchner funnel and dried under reduced pressure to give the title compound (121 g).

(c) 5-Acetyl-8-benzyloxy-1H-quinolin-2-one

To the product from step (b) (37.7 g, 186 mmol) was added N,N-dimethylformamide (200 mL) and potassium carbonate (34.5 g, 250 mmol) followed by benzyl bromide (31.8 g, 186 mmol). The mixture was stirred at room temperature for 2.25 hour and then poured into saturated sodium chloride (3.5 L) at 0° C. and stirred for 1 hour. The product was collected and dried on a Buchner funnel for 1 hour, and the resulting solids were dissolved in dichloromethane (2 L) and this mixture was dried over sodium sulfate. The solution was filtered through a pad of Celite which was then washed with dichloromethane (5×200 mL). The combined filtrate was then concentrated to dryness and the resulting solids were triturated with ether (500 mL) for 2 h. The product was collected on a Buchner funnel, washed with ether (2×250 mL) and dried under reduced pressure to give the title compound (44 g) as a powder.

(d) 8-Benzyloxy-5-(2-bromoacetyl)-1H-quinolin-2-one

The product from step (c) (20.0 g, 68.2 mmol) was dissolved in dichloromethane (200 mL) and cooled to 0° C. Boron trifluoride diethyl etherate (10.4 mL, 82.0 mmol) was added via syringe and the mixture was warmed to room temperature to give a thick suspension. The suspension was heated at 45° C. (oil bath) and a solution of bromine (11.5 g, 72.0 mmol) in dichloromethane (100 mL) was added over 40 min. The mixture was kept at 45° C. for an additional 15 min and then cooled to room temperature. The mixture was concentrated under reduced pressure and then triturated with 10% aqueous sodium carbonate (200 mL) for 1 hour. The solids were collected on a Buchner funnel, washed with water (4×100 mL) and dried under reduced pressure. The product of two runs was combined for purification. The crude product (52 g) was triturated with 50% methanol in chloroform (500 mL) for 1 hour. The product was collected on a Buchner funnel and washed with 50% methanol in chloroform (2×50 mL) and methanol (2×50 mL). The solid was dried under reduced pressure to give the title compound (34.1 g) as a powder.

Preparation 4

8-Benzyloxy-5-[(R)-2-bromo-1-(tert-butyldimethylsilanyloxy)ethyl]-1H-quinolin-2-one (a) 8-Benzyloxy-5-((R)-2-bromo-1-hydroxyethyl)-1H-quinolin-2-one (R)-(+)-α,α-Diphenylprolinol (30.0 g, 117 mmol) and trimethylboroxine (11.1 mL, 78 mmol) were combined in toluene (300 mL) and stirred at room temperature for 30 min. The mixture was placed in a 150° C. oil bath and liquid was distilled off. Toluene was added in 20 mL aliquots and distillation was continued for 4 h. A total of 300 mL toluene was added. The mixture was then cooled to room temperature. A 500 μL aliquot was evaporated to dryness and weighed (246 mg) to determine that the concentration of catalyst was 1.8 M.

8-Benzyloxy 5-(2-bromoacetyl)-1H-quinolin-2-one (90.0 g, 243 mmol) was placed under nitrogen and tetrahydrofuran (900 mL) was added followed by the catalyst described above (1.8 M in toluene, 15 mL, 27 mmol). The suspension was cooled to −10±5° C. in an ice/isopropanol bath. Borane (1.0 M in THF, 294 mL, 294 mmol) was added over 4 h. The reaction was then stirred an additional 45 min at ±10° C. and then methanol (250 mL) was added slowly. The mixture was concentrated under vacuum and the residue was dissolved in boiling acetonitrile (1.3 L), filtered while hot and then cooled to room temperature. The crystals were filtered, washed with acetonitrile and dried under vacuum to give the title compound (72.5 g, 196 mmol, 81% yield, 95% ee, 95% pure by HPLC).

(b) 8-Benzyloxy-5-[(R)-2-bromo-1-(tert-butyldimethylsilanyloxy)ethyl]-1H-quinolin-2-one To the product of step (b) (70.2 g, 189 mmol) was added N,N-dimethylformamide (260 mL) and this mixture was cooled in an ice bath under nitrogen. 2,6-Lutidine (40.3 g, 376 mmol) was added over 5 min and then tert-butyldimethylsilyl trifluoromethanesulfonate (99.8 g, 378 mmol) was added slowly while maintaining the temperature below 20° C. The mixture was allowed to warm to room temperature for 45 min. Methanol (45 mL) was added to the mixture dropwise over 10 min and the mixture was partitioned between ethyl acetate/cyclohexane (1:1, 500 mL) and water/brine (1:1, 500 mL). The organics were washed twice more with water/brine (1:1, 500 mL each). The combined organics were evaporated under reduced pressure to give a light yellow oil. Two separate portions of cyclohexane (400 mL) were added to the oil and distillation continued until a thick white slurry was formed. Cyclohexane (300 mL) was added to the slurry and the resulting white crystals were filtered, washed with cyclohexane (300 mL) and dried under reduced pressure to give the title compound (75.4 g, 151 mmol, 80% yield, 98.6% ee).

Preparation 5

8-Benzyloxy-5-[(R)-2-(N-benzylamino)-1-(tert-butyldimethylsilanyloxy)ethyl]1H-quinolin-2-one A stirred solution of the product of Preparation 4 (1.00 g, 2.05 mmol) and benzylamine (493 μL, 4.51 mmol) in DMSO (1.7 mL) was heated at 105° C. for 4 h. The reaction mixture was allowed to cool and was then diluted with EtOAc (10 mL) and the organic layer was washed with saturated aqueous ammonium chloride solution (5 mL) and 1N sodium hydroxide (5 mL), dried ($MgSO_4$) and solvent removed under reduced pressure. The crude residue was purified by column chromatography (50% EtOAc/hexanes) to give the title compound (700 mg, 67%). MS m/z: $[M+H^+]$ calcd for $C_{31}H_{38}N_2O_3Si$ 515.27; found 515.5.

Preparation 6

5-[(R)-2-Amino-1-(tert-butyldimethylsilanyloxy)ethyl]-8-hydroxy-1H-quinolin-2-one A stirred solution of the product of Preparation 5 (3.16 g, 6.15 mmol) and palladium (10 wt. % (dry basis) on activated carbon) (1.58 g) in ethanol (62 mL) was placed under an atmosphere of hydrogen for 24 h. The reaction mixture was filtered through Celite, washed with methanol (15 mL), and then the solvent was removed under reduced pressure to give the title compound as a solid (1.52 g, 4.55 mmol, 74%).

Preparation 7

9-{9-[(R)-2-(tert-Butyldimethylsilanyloxy)-2-(8-hydroxy-2-oxo-1,2-dihydroquinolin-5-yl)ethylamino]nonyl}-7-(2-hydroxy-2,2-dithiophen-2-ylacetoxy)-9-methyl-3-oxa-9-azoniatricyclo[3.3.1.$0^{2,4}$]nonane A stirred solution of the product of Preparation 2 (292 mg, 0.5 mmol), the product of Preparation 6 (335 mg, 1 mmol) and cesium carbonate (244 mg, 0.75 mmol) in DMF (2.5 mL) was heated at 70° C. for 24 h. The reaction mixture was allowed to cool and the solvent was removed under reduced pressure. The crude product was used without further purification.

Example 1

7-(2-Hydroxy-2,2-dithiophen-2-ylacetoxy)-9-{9-[(R)-2-hydroxy-2-(8-hydroxy-2-oxo-1,2-dihydroquinolin-5-yl)ethylamino]nonyl}-9-methyl-3-oxa-9-azonia-tricyclo[3.3.1.$0^{2,4}$]nonane Ditrifluoroacetate Triethylamine trihydrofluoride (163 µL, 1 mmol) was added to a stirred solution of the product of Preparation 7 (418 mg, 0.5 mmol) in DCM (5 mL) and DMF (3 mL). The reaction mixture was stirred at ambient temperature for 24 h and then the solvent was removed under reduced pressure. The crude residue was purified by preparative HPLC to afford the title compound (14 mg, 2 TFA salt). MS m/z: $[M+H^+]$ calcd for $C_{38}H_{48}N_3O_7S_2$ 723.295; found 722.3; HPLC (10-70) $R_t$=2.56.

Preparation 8

(tert-Butyldimethylsilanyloxy)dithien-2-ylacetic Acid 9-Methyl-3-oxa-9-azatricyclo[3.3.1.$0^{2,4}$]non-7-yl Ester To the product of Preparation 1 (34.8 mmol) and imidazole (4.7 g, 69.7 mmol) dissolved in 100 mL of DMF is added tert-butyldimethylsilyl chloride (5.78 g, 38.3 mmol). The reaction mixture is stirred for 18 hours. The reaction mixture is then partitioned between 200 mL of saturated sodium chloride and 200 mL of diethyl ether. The aqueous layer is extracted with 200 mL of diethyl ether. The organic layers are then combined, washed with saturated sodium chloride (3×100 mL), dried over $MgSO_4$ and concentrated. The residue is purified by silica gel chromatography to give the title compound.

Preparation 9

7-[2-(tert-Butyldimethylsilanyloxy)-2,2-dithiophen-2-ylacetoxy]-9-(2-methoxycarbonylethyl)-9-methyl-3-oxa-9-azoniatricyclo[3.3.1.$0^{2,4}$]nonane Methyl 3-bromopropionate (553 µL, 5.07 mmol) is added to a stirred solution of the product of Preparation 8 (3.38 mmol) and DIPEA (1.76 mL, 10.1 mmol) in acetonitrile (34 mL) at 50° C. and the reaction mixture is heated at 50° C. overnight. The solvent is then removed under reduced pressure and the residue is purified by flash chromatography to give the title compound.

Preparation 10

9-(2-Carboxyethyl)-7-[2-(tert-butyldimethylsilanyloxy)-2,2-dithiophen-2-ylacetoxy]-9-methyl-3-oxa-9-azoniatricyclo[3.3.1.$0^{2,4}$]nonane A stirred solution of the product of Preparation 9 (2.37 mmol) and lithium hydroxide (171 mg, 7.11 mmol) in 50% THF/$H_2O$ (24 mL) is heated at 30° C. overnight, and then acidified with concentrated hydrochloric acid and lyophilized to give the title compound.

Preparation 11

{5-[(R)-2-(8-Benzyloxy-2-oxo-1,2-dihydroquinolin-5-yl)-2-(tert-butyldimethyl-silanyloxy)ethylamino]pentyl}carbamic Acid tert-Butyl Ester The product of Preparation 4 (600 mg, 1.23 mmol) and N-tert-butoxycarbonyl-1,5-diaminopentane (622 mg, 3.07 mmol) were dissolved in dimethyl sulfoxide (1.23 mL) and heated to 105° C. for 6 h. The reaction mixture was then cooled and diluted with ethyl acetate (10 mL) and washed with saturated aqueous sodium bicarbonate solution (4 mL). The organic phase was dried (magnesium sulfate) and the solvent was removed under reduced pressure. The crude residue was purified by column chromatography (5-10% methanol/dichloromethane) to give the title compound (~100% yield).

Preparation 12

5-[(R)-2-(5-Aminopentylamino)-1-(tert-butyldimethylsilanyloxy)ethyl]-8-benzyloxy-1H-quinolin-2-one A solution of the product of Preparation 11 (800 mg, 1.31 mmol) in trifluoroacetic acid/dichloromethane (25%, 12 mL) was stirred at ambient temperature for 1 hour. The solvent was then removed under reduced pressure and the crude residue was dissolved in dichloromethane (15 mL) and washed with 1N sodium hydroxide (8 mL). The organic phase was separated, dried (magnesium sulfate) and the solvent was removed under reduced pressure to give the title compound (509 mg, 81% yield over 2 steps).

Preparation 13

9-(2-{5-[(R)-2-(8-Benzyloxy-2-oxo-1,2-dihydroquinolin-5-yl)-2-(tert-butyldimethyl-silanyloxy)ethylamino]pentylcarbamoyl}ethyl)-7-[2-(tert-butyldimethylsilanyloxy)-2,2-dithiophen-2-ylacetoxy]-9-methyl-3-oxa-9-azoniatricyclo[3.3.1.$0^{2,4}$]nonane To the product of Preparation 10 (1.13 mmol) and HATU (430 mg, 1.13 mmol) is added the product of Preparation 12 (458 mg, 0.90 mmol) in DMF (1.8 mL), followed by DIPEA (204 µL, 1.17 mmol). The reaction mixture is stirred at 50° C. for 12 h, and then the solvent is removed under reduced pressure and the crude residue is purified by flash chromatography to give the title compound.

Preparation 14

9-(2-{5-[(R)-2-(8-Benzyloxy-2-oxo-1,2-dihydro-quinolin-5-yl)-2-hydroxyethylamino]-pentylcarbamoyl}ethyl)-7-(2-hydroxy-2,2-dithiophen-2-ylacetoxy)-9-methyl-3-oxa-9-azoniatricyclo[$3.3.1.0^{2,4}$]nonane To a stirred solution of the product of Preparation 13 (0.28 mmol) in dichloromethane (2.8 mL) is added triethylamine trihydrofluoride (91 μL, 0.56 mmol). The reaction mixture is stirred for 10 h and then the solvent is removed under reduced pressure and the crude residue is purified by flash chromatography to give the title compound.

Example 2

7-(2-Hydroxy-2,2-dithiophen-2-ylacetoxy)-9-(2-{5-[(R)-2-hydroxy-2-(8-hydroxy-2-oxo-1,2-dihydro-quinolin-5-yl)ethylamino]pentylcarbamoyl}ethyl)-9-methyl-3-oxa-9-azoniatricyclo[$3.3.1.0^{2,4}$]nonane To a stirred solution of the product of Preparation 14 (0.28 mmol) in ethanol (2.8 mL) is added palladium (10 wt. % (dry basis) on activated carbon) (81 mg) and the reaction mixture is placed under an atmosphere of hydrogen and stirred overnight. The reaction mixture is then filtered and solvent is removed under reduced pressure. The crude residue is purified by preparative HPLC to give the title compound as the ditrifluoroacetate salt.

Preparation 15

7-[2-(tert-Butyldimethylsilanyloxy)-2,2-dithiophen-2-ylacetoxy]-9-methyl-9-(2-methylaminoethyl)-3-oxa-9-azoniatricyclo[$3.3.1.0^{2,4}$]nonane 2-(N-Benzyloxycarbonyl-N-methylamino)ethyl bromide (5.07 mmol) is added to a stirred solution of the product of Preparation 8 (3.38 mmol) and DIPEA (1.76 mL, 10.1 mmol) in acetonitrile (34 mL) at 50° C. and the reaction mixture is heated at 50° C. overnight. The solvent is then removed under reduced pressure and the residue is dissolved in methanol (100 mL) and palladium (10 wt. % (dry basis) on activated carbon) (5 g) is added. The reaction mixture is stirred under hydrogen (30 psi) for 12 h and then filtered through Celite, which is washed with methanol, and solvent is evaporated to give the title compound.

Preparation 16

9-{2-[(6-Bromohexanoyl)methylamino]ethyl}-7-[2-(tert-butyldimethylsilanyloxy)-2,2-dithiophen-2-ylacetoxy]-9-methyl-3-oxa-9-azoniatricyclo[$3.3.1.0^{2,4}$]nonane 6-Bromohexanoyl chloride (3.23 mL, 21.1 mmol) is added to a stirred solution of the product of Preparation 15 (17.6 mmol) and DIPEA (6.13 mL, 35.2 mmol) in dichloroethane (170 mL). The reaction mixture is stirred for 1 hour and then the solvent is removed under reduced pressure and the crude residue is purified by flash chromatography to give the title compound.

Preparation 17

9-[2-({6-Benzyl-[(R)-2-(8-benzyloxy-2-oxo-1,2-dihydroquinolin-5-yl)-2-(tert-butyldimethylsilanyloxy)ethylamino]hexanoyl}methylamino)ethyl]-7-[2-(tert-butyldimethylsilanyloxy)-2,2-dithiophen-2-ylacetoxy]-9-methyl-3-oxa-9-azoniatricyclo[$3.3.1.0^{2,4}$]nonane To a stirred solution of the product of Preparation 5 (1.57 mmol) and DIPEA (819 μL, 4.7 mmol) in acetonitrile (3.14 mL) is added the product of Preparation 16 (995 mg, 1.88 mmol). The reaction mixture is heated to 80° C. for 24 h. The solvent is removed under reduced pressure and the residue purified by flash chromatography to obtain the title compound.

Preparation 18

9-{2-[(6-{Benzyl-[(R)-2-(8-benzyloxy-2-oxo-1,2-dihydroquinolin-5-yl)-2-hydroxy-ethyl]amino}hexanoyl)methylamino]ethyl}-7-(2-hydroxy-2,2-dithiophen-2-yl-acetoxy)-9-methyl-3-oxa-9-azoniatricyclo[$3.3.1.0^{2,4}$]nonane To a stirred solution of the product of Preparation 17 (0.47 mmol) in dichloromethane (4.7 mL) is added triethylamine trihydrofluoride (116 μL, 0.71 mmol). The reaction mixture is stirred for 10 h. and then the solvent is removed under reduced pressure and the crude residue is purified by flash chromatography to give the title compound.

Example 3

7-(2-Hydroxy-2,2-dithiophen-2-ylacetoxy)-9-[2-({6-[(R)-2-hydroxy-2-(8-hydroxy-2-oxo-1,2-dihydro-quinolin-5-yl)ethylamino]hexanoyl}methylamino)ethyl]-9-methyl-3-oxa-9-azoniatricyclo[$3.3.1.0^{2,4}$]nonane To a stirred solution of the product of Preparation 18 (0.47 mmol) in ethanol (4.7 mL) is added palladium (10 wt. % (dry basis) on activated carbon) (160 mg) and the reaction mixture is placed under an atmosphere of hydrogen and stirred overnight. The reaction mixture is then filtered and solvent is removed under reduced pressure. The crude residue is purified by preparative HPLC to give the title compound as the ditrifluoroacetate salt.

Preparation 19

9-[2-(4-Aminomethylphenylcarbamoyl)ethyl]-7-[2-(tert-butyldimethylsilanyloxy)-2,2-dithiophen-2-ylacetoxy]-9-methyl-3-oxa-9-azoniatricyclo[$3.3.1.0^{2,4}$]nonane To a stirred solution of 4-(N-tert-butoxycarbonylaminomethyl)aniline (756 mg, 3.4 mmol), the product of Preparation 10 (4.08 mmol) and HATU (1.55 g, 4.08 mmol) in DMF (6.8 mL) is added DIPEA (770 μL, 4.42 mmol). The reaction mixture is stirred at 50° C. overnight and then the solvent is removed under reduced pressure. The resulting residue is purified by flash chromatography. The product is dissolved in TFA/DCM (25%, 30 mL) and stirred at room temperature for 2 h. The solvent is then removed under reduced pressure and the crude residue is purified by flash chromatography to give the title compound.

Preparation 20

9-[2-(4-{[(R)-2-(8-Benzyloxy-2-oxo-1,2-dihydro-quinolin-5-yl)-2-(tert-butyldimethyl-silanyloxy)ethylamino]methyl}phenylcarbamoyl)ethyl]7-[2-(tert-butyldimethylsilanyloxy)-2,2-dithiophen-2-ylacetoxy]-9-methyl-3-oxa-9-azoniatricyclo[$3.3.1.0^{2,4}$]nonane A solution of the product of Preparation 19 (1.04 mmol), the product of Preparation 4 (610 mg, 1.25 mmol), sodium bicarbonate (262 mg, 3.12 mmol) and sodium iodide (203 mg, 1.35 mmol) in THF (0.52 mL) are heated at 80° C. for 12 h. The solvent is removed under reduced pressure and the crude residue is purified by flash chromatography to give the title compound.

Preparation 21

9-[2-(4-{[(R)-2-(8-Benzyloxy-2-oxo-1,2-dihydro-quinolin-5-yl)-2-hydroxyethylamino]-methyl}phenylcarbamoyl)ethyl]-7-(2-hydroxy-2,2-dithiophen-2-ylacetoxy)-9-methyl-3-oxa-9-azoniatricyclo[$3.3.1.0^{2,4}$]nonane To a stirred solution of the product of Preparation 20 (0.8 mmol) in dichloromethane (8 mL) is added triethylamine trihydrofluoride (261 μL, 1.6 mmol). The reaction mixture is stirred for 10 h and then the solvent is removed under reduced pressure and the crude residue is purified by flash chromatography to give the title compound.

Example 4

7-(2-Hydroxy-2,2-dithiophen-2-ylacetoxy)-9-[2-(4-{[(R)-2-hydroxy-2-(8-hydroxy-2-oxo-1,2-dihydro-quinolin-5-yl)ethylamino]methyl}phenylcarbamoyl)ethyl]-9-methyl-3-oxa-9-azoniatricyclo[$3.3.1.0^{2,4}$]nonane To a stirred solution of the product of Preparation 21 (0.65 mmol) in ethanol (6.5 mL) is added palladium (10 wt. % (dry basis) on activated carbon) (200 mg) and the reaction mixture is placed under a hydrogen atmosphere and stirred overnight. The reaction mixture is then filtered and the solvent is removed under reduced pressure. The crude residue is purified by preparative HPLC to give the title compound as the ditrifluoroacetate salt.

Preparation 22

9-(2-tert-Butoxycarbonylaminoethyl)-7-[2-(tert-butyldimethylsilanyloxy)-2,2-dithiophen-2-ylacetoxy]-9-methyl-3-oxa-9-azoniatricyclo[$3.3.1.0^{2,4}$]nonane To a stirred solution of the product of Preparation 8 (6.76 mmol) and DIPEA (3.54 mL, 20.3 mmol) in acetonitrile (67.6 mL) at 50° C. is added 2-tert-butoxycarbonylaminoethyl bromide (1.82 g, 8.11 mmol) and the reaction mixture is heated at 50° C. overnight. The solvent is then removed under reduced pressure and the residue is purified by flash chromatography to yield the title compound.

Preparation 23

9-(2-Aminoethyl)-7-[2-(tert-butyldimethylsilanyloxy)-2,2-dithiophen-2-ylacetoxy]-9-methyl-3-oxa-9-azoniatricyclo[$3.3.1.0^{2,4}$]nonane The product of Preparation 22 is dissolved in TFA/DCM (25%, 52 mL) and stirred at room temperature for 2 h. The solvent is then removed under reduced pressure and the residue is purified by flash chromatography to yield the title compound.

Preparation 24

9-[2-(4-Aminomethylbenzoylamino)ethyl]-7-[2-(tert-butyldimethylsilanyloxy)-2,2-dithiophen-2-ylacetoxy]-9-methyl-3-oxa-9-azoniatricyclo[$3.3.1.0^{2,4}$]nonane To a stirred solution of the product of Preparation 23 (1 mmol), 4-(tert-butoxycarbonylaminomethyl)benzoic acid (301 mg, 1.2 mmol) and HATU (456 mg, 1.2 mmol) in DMF (2 mL) is added DIPEA (226 μL, 1.3 mmol). The reaction mixture is stirred at room temperature overnight and then the solvent is removed under reduced pressure. The resulting residue is dissolved in TFA/DCM (25%, 10 mL) and this mixture is stirred at room temperature for 2 h. The solvent is removed under reduced pressure and the residue is purified by flash chromatography to yield the title compound.

Preparation 25

9-[2-(4-{[(R)-2-(8-Benzyloxy-2-oxo-1,2-dihydro-quinolin-5-yl)-2-(tert-butyldimethyl-silanyloxy)ethylamino]methyl}benzoylamino)ethyl]-7-[2-(tert-butyldimethylsilanyloxy)-2,2-dithiophen-2-ylacetoxy]-9-methyl-3-oxa-9-azoniatricyclo[$3.3.1.0^{2,4}$]nonane A solution of the product of Preparation 24 (1.1 mmol), the product of Preparation 4 (634 mg, 1.3 mmol), sodium bicarbonate (277 mg, 3.3 mmol) and sodium iodide (215 mg, 1.43 mmol) in THF (0.55 mL) is heated at 80° C. for 12 h. The solvent is removed under reduced pressure and the crude residue is purified by flash chromatography to give the title compound.

Example 5

9-[2-(4-{[(R)-2-(8-Hydroxy-2-oxo-1,2-dihydro-quinolin-5-yl)-2-hydroxyethylamino]-methyl}benzoylamino)ethyl]-7-(2-hydroxy-2,2-dithiophen-2-yl-acetoxy)-9-methyl-3-oxa-9-azoniatricyclo[$3.3.1.0^{2,4}$]nonane Using the product of Preparation 25 and following the procedures described in Preparation 21 and Example 4, the title compound is prepared as the ditrifluoroacetate salt.

Preparation 26

5-[(R)-2-(5-Aminopentylamino)-1-(tert-butyldimethylsilanyloxy)ethyl]-8-benzyloxy-1H-quinolin-2-one N-tert-butoxycarbonyl-1,5-diaminopentane (1.04 g, 5.12 mmol) was added to a solution of the product of Preparation 4 (1.00 g, 2.05 mmol) in dimethyl sulfoxide (2 mL). The solution was stirred at 75° C. for 12 hours, at which time LCMS analysis showed that the reaction was complete. The reaction mixture was then concentrated under vacuum to dryness. To the residue was added dichloromethane (2 mL) and trifluoroacetic acid (1 mL) was then added. The solution was stirred at room temperature for about 3 hours, at which time MS analysis showed that the reaction was complete. The solution was concentrated to half its volume and 1N sodium hydroxide was added until the pH was adjusted to 14. The organic layer was collected, washed with brine, dried over magnesium sulfate and then concentrated to yield 782 mg of the title compound as an oil. MS m/z: [M+H$^+$] calcd for $C_{29}H_{43}N_3O_3Si$ 510.8; found 510.

Preparation 27

9-[2-(3-{5-[(R)-2-(8-Benzyloxy-2-oxo-1,2-dihydroquinolin-5-yl)-2-(tert-butyldimethyl-silanyloxy)ethylamino]pentyl}ureido)ethyl]-7-[2-(tert-butyldimethylsilanyloxy)-2,2-dithiophen-2-ylacetoxy]-9-methyl-3-oxa-9-azoniatricyclo[3.3.1.0$^{2,4}$]nonane Carbonyl diimidazole (127 mg, 0.78 mmol) is added to a solution of the product of Preparation 23 (78 mmol) in dimethyl formamide (4 mL) and the resulting mixture is stirred at room temperature for 3 hours. After 3 hours, the product of Preparation 26 (399 mg, 0.78 mmol) is added to the reaction mixture and this mixture is stirred for 12 hours at room temperature. The reaction mixture is concentrated in vacuo and the residue is purified by flash chromatography to give the title compound.

Example 6

7-(2-Hydroxy-2,2-dithiophen-2-yl-acetoxy)-9-[2-(3-{5-[(R)-2-hydroxy-2-(8-hydroxy-2-oxo-1,2-dihydroquinolin-5-yl)ethylamino]pentyl}ureido)ethyl]-9-methyl-3-oxa-9-azoniatricyclo[3.3.1.0$^{2,4}$]nonane Using the product of Preparation 27 and following the procedures described in Preparation 21 and Example 4, the title compound is prepared as the ditrifluoroacetate salt.

Example 7

7-(2-Hydroxy-2,2-dithiophen-2-ylacetoxy)-9-[3-(3-{5-[(R)-2-hydroxy-2-(8-hydroxy-2-oxo-1,2-dihydroquinolin-5-yl)ethylamino]pentyl}ureido)propyl]-9-methyl-3-oxa-9-azoniatricyclo[3.3.1.0$^{2,4}$]nonane Using the method described above for the preparation of the compound of Example 6, and substituting 3-tert-Butoxycarbonylaminoprop-1-yl bromide for 2-tert-butoxycarbonylaminoethyl bromide, the title compound is prepared as the ditrifluoroacetate salt.

Preparation 28

5-[(R)-2-[(3-Aminomethylcyclohexylmethyl)amino]-1-(tert-butyldimethylsilanyloxy)ethyl]-8-benzyloxy-1H-quinolin-2-one A stirred solution of the product of Preparation 4 (1.46 g, 3 mmol) and 1,3-cyclohexanebis(methylamine) (426 mg, 3 mmol) in DMSO (3 mL) was heated at 100° C. for 6 h. The reaction mixture was allowed to cool and it was then diluted with dichloromethane (20 mL) and washed with saturated aqueous sodium bicarbonate solution (10 mL). The organic layer was dried ($MgSO_4$) and the solvent was removed under reduced pressure. The crude residue was purified by flash chromatography (10% MeOH/DCM and 0.5% $NH_4OH$) to give the title compound as a solid (775 mg, 50% yield). MS m/z: [M+H$^+$] calcd for $C_{32}H_{47}N_3O_3Si$ 550.3; found 550.6.

Preparation 29

7-[2-(tert-Butyldimethylsilanyloxy)-2,2-dithiophen-2-ylacetoxy]-9-{2-[(3-{[(R)-2-(tert-butyldimethylsilanyloxy)-2-(8-benzyloxy-2-oxo-1,2-dihydroquinolin-5-yl)ethylamino]-methyl}cyclohexylmethyl)carbamoyl]-ethyl}-9-methyl-3-oxa-9-azoniatricyclo[3.3.1.0$^{2,4}$]nonane To a stirred solution of the product of Preparation 28 (552 mg, 1.01 mmol), the product of Preparation 10 (0.84 mmol) and HATU (384 mg, 1.01 mmol) in DMF (1.68 mL) is added DIPEA (190 μL, 1.09 mmol). The reaction mixture is stirred at 50° C. overnight and then the solvent is removed under reduced pressure. The resulting residue is purified by flash chromatography to give the title compound.

Example 8

7-(2-Hydroxy-2,2-dithiophen-2-ylacetoxy)-9-{2-[(3-{[(R)-2-hydroxy-2-(8-hydroxy-2-oxo-1,2-dihydroquinolin-5-yl)ethylamino]methyl}cyclohexylmethyl)carbamoyl]-ethyl}-9-methyl-3-oxa-9-azoniatricyclo[3.3.1.0$^{2,4}$]nonane Using the product of Preparation 29 and following the procedures described in Preparation 21 and Example 4, the title compound is prepared as the ditrifluoroacetate salt.

Preparation 30

9-{2-[((1S,3R)-3-Aminocyclopentanecarbonyl)amino]ethyl}-7-[2-(tert-butyldimethylsilanyloxy)-2,2-dithiophen-2-ylacetoxy]-9-methyl-3-oxa-9-azoniatricyclo[3.3.1.0$^{2,4}$]nonane To a stirred solution of the product of Preparation 23 (0.94 mmol), (1R,3S)-3-tert-butoxycarbonylaminocyclopentanecarboxylic acid (258 mg, 1.1 mmol) and HATU (428 mg, 1.1 mmol) in DMF (5 mL) is added DIPEA (245 μL, 1.09 mmol). The reaction mixture is stirred at room temperature overnight and then the solvent is removed under reduced pressure. The crude product is purified by flash chromatography and then is dissolved in a trifluoroacetic acid/DCM mixture (1 mL/5 mL) and stirred at room temperature for 1 h. The solvent is removed under reduced pressure and the residue is purified by flash chromatography to give the title compound.

Preparation 31

7-[2-(tert-Butyldimethylsilanyloxy)-2,2-dithiophen-2-ylacetoxy]-9-[2-({(1S,3R)-3-[(R)-2-(tert-butyldimethyl-silanyloxy)-2-(8-benzyloxy-2-oxo-1,2-dihydroquinolin-5-yl)ethylamino]-cyclopentanecarbonyl}amino)-ethyl]-9-methyl-3-oxa-9-azoniatricyclo[3.3.1.0$^{2,4}$]-nonane A stirred solution of the product of Preparation 30 (0.38 mmol) and the product of Preparation 4 (92 mg, 0.19 mmol) in DMSO (0.38 mL) is heated at 90° C. for 5 h. The solvent is removed under reduced pressure and the crude product is purified by flash chromatography to yield the title compound.

Example 9

7-(2-Hydroxy-2,2-dithiophen-2-ylacetoxy)-9-[2-({(1S,3R)-3-[(R)-2-hydroxy-2-(8-hydroxy-2-oxo-1,2-dihydroquinolin-5-yl)ethylamino]cyclopentanecarbonyl}amino)-ethyl]-9-methyl-3-oxa-9-azoniatricyclo[3.3.1.$0^{2,4}$]nonane Using the product of Preparation 31 and following the procedures described in Preparation 21 and Example 4, the title compound is prepared as the ditrifluoroacetate salt.

Preparation 32

4-(tert-Butoxycarbonylaminomethyl)-2-chlorophenylamine

A stirred solution of 4-aminomethyl-2-chlorophenylamine (940 mg, 6 mmol) and di-tert-butyl dicarbonate (1.44 g, 6.6 mmol) in dichloromethane (30 mL) was stirred at room temperature for 4 h, at which time the reaction was determined to be complete by LCMS. The reaction mixture was then washed with saturated aqueous sodium bicarbonate (15 mL) and the organic layer was dried over sodium sulfate and the solvent was removed under reduced pressure. The resulting orange solid was recrystallized from ethyl acetate to give the title intermediate as a white solid (~100% yield).

Preparation 33

N-[4-(tert-Butoxycarbonylaminomethyl)-2-chlorophenyl]-2-bromoacetamide

To a stirred solution of the product of Preparation 32 (1.54 g, 6.0 mmol) in a mixture of dichloromethane (35 mL) and DIPEA (12 mmol) is added dropwise 2-bromoacetyl bromide (8.45 mmol). After 1 h, the solvent is removed under reduced pressure and the crude product is purified by flash chromatography to yield the title compound.

Preparation 34

9-[2-(4-Aminomethyl-2-chlorophenylcarbamoyl)ethyl]-7-[2-(tert-butyldimethylsilanyloxy)-2,2-dithiophen-2-ylacetoxy]-9-methyl-3-oxa-9-azoniatricyclo[3.3.1.$0^{2,4}$]nonane A solution of the product of Preparation 8 (3.5 mmol) and the product of Preparation 33 (3.85 mmol) in a DMF (12 mL, 1:1) is heated at 80° C. for 24 h. The reaction mixture is allowed to cool and the solvent is removed under reduced pressure. To the residue is added dichloromethane (24 mL) and TFA (8 mL). The resulting mixture is stirred for 1 h and then the solvent is removed under reduced pressure. The residue the crude product is then purified by flash chromatography to yield the title compound.

Preparation 35

9-[2-(2-Chloro-4-{[(R)-2-(tert-butyldimethylsilanyloxy)-2-(8-benzyloxy-2-oxo-1,2-dihydroquinolin-5-yl)-ethylamino]methyl}phenylcarbamoyl)ethyl]-7-[2-(tert-butyldimethylsilanyloxy)-2,2-dithiophen-2-ylacetoxy]-9-methyl-3-oxa-9-azoniatricyclo[3.3.1.$0^{2,4}$]nonane A stirred solution of the product of Preparation 34 (2.79 mmol) and the product of Preparation 4 (680 mg, 1.39 mmol) in DMSO (1.39 mL) is heated at 90° C. for 8 h and then cooled to room temperature. The solvent is removed under reduced pressure and the resulting crude residue is purified by flash chromatography to give the title intermediate.

Example 10

9-[2-(2-Chloro-4-{[(R)-2-hydroxy-2-(8-hydroxy-2-oxo-1,2-dihydroquinolin-5-yl)-ethylamino]methyl}phenylcarbamoyl)ethyl]7-(2-hydroxy-2,2-dithiophen-2-yl-acetoxy)-9-methyl-3-oxa-9-azoniatricyclo[3.3.1.$0^{2,4}$]nonane Using the product of Preparation 35 and following the procedures described in Preparation 21 and Example 4, the title compound is prepared as the ditrifluoroacetate salt.

Preparation 36

2-Chloroethanesulfonic Acid (5-tert-Butoxycarbonylaminopentyl)amide

To a stirred solution of 5-(tert-butoxycarbonylamino)pentylamine (1.00 g, 4.94 mmol) and triethylamine (689 μL g, 4.94 mmol) in dichloromethane (22 mL) at 0° C. was added 2-chloro-1-ethanesulfonyl chloride (470 μL, 4.50 mmol). The reaction mixture was stirred for 2 h at room temperature and then washed with saturated aqueous sodium bicarbonate solution (15 mL). The organic layer was dried ($Na_2SO_4$) and the solvent was removed under reduced pressure to give the title compound (100% yield), which was used in the next step without further purification.

Preparation 37

9-[2-(5-tert-Butoxycarbonylaminopentyl sulfamoyl)ethyl]-7-[2-(tert-butyldimethylsilanyloxy)-2,2-dithiophen-2-ylacetoxy]-9-methyl-3-oxa-9-azoniatricyclo[3.3.1.$0^{2,4}$]nonane A solution of the product of Preparation 8 (3.5 mmol) and the product of Preparation 36 (1.62 g, 4.94 mmol) in dichloromethane and methanol (22 mL, 1:1) is heated at 60° C. for 5 h. The reaction mixture is allowed to cool to room temperature and the solvent is removed under reduced pressure. The crude residue is purified by flash chromatography to give the title intermediate.

Preparation 38

9-[2-(5-Aminopentylsulfamoyl)ethyl]-7-[2-(tert-butyldimethylsilanyloxy)-2,2-dithiophen-2-ylacetoxy]-9-methyl-3-oxa-9-azoniatricyclo[3.3.1.0$^{2,4}$]nonane A solution of the product of Preparation 37 (2.72 mmol) is stirred in dichloromethane (21 mL) and TFA (7 mL) for 1 h and then the solvent is removed under reduced pressure. The crude residue is purified by flash chromatography to give the title intermediate.

Preparation 39

7-[2-(tert-Butyldimethylsilanyloxy)-2,2-dithiophen-2-ylacetoxy]-9-(2-{5-[(R)-2-(tert-butyl-dimethylsilanyl-oxy)-2-(8-benzyloxy-2-oxo-1,2-dihydroquinolin-5-yl)ethylamino]pentylsulfamoyl}-ethyl)-9-methyl-3-oxa-9-azoniatricyclo[3.3.1.0$^{2,4}$]nonane A stirred solution of the product of Preparation 38 (1.88 mmol) and the product of Preparation 4 (460 mg, 0.94 mmol) in DMSO (0.92 mL) is heated at 90° C. for 8 h and then cooled to room temperature. The solvent is removed under reduced pressure and the resulting crude residue is purified by flash chromatography to give the title intermediate.

Example 11

7-(2-Hydroxy-2,2-dithiophen-2-ylacetoxy)-9-(2-{5-[(R)-2-hydroxy-2-(8-hydroxy-2-oxo-1,2-dihydroquinolin-5-yl)-ethylamino]pentylsulfamoyl}ethyl)-9-methyl-3-oxa-9-azoniatricyclo[3.3.1.0$^{2,4}$]nonane Using the product of Preparation 39 and following the procedures described in Preparation 21 and Example 4, the title compound is prepared as the ditrifluoroacetate salt.

Preparation 40

9-{2-[(4-Formylbenzenesulfonyl)methylamino]ethyl}-7-[2-(tert-butyldimethylsilanyloxy)-2,2-dithiophen-2-ylacetoxy]-9-methyl-3-oxa-9-azoniatricyclo[3.3.1.0$^{2,4}$]nonane To a stirred solution of the product of Preparation 15 (1 mmol) and triethylamine (167 µL, 1.2 mmol) in dichloromethane (5 mL) is added 4-formylbenzenesulfonyl chloride (225 mg, 1.1 mmol). After stirring for 1 h at room temperature, the solvent is removed under reduced pressure and the resulting crude residue is purified by flash chromatography to give the title intermediate.

Preparation 41

7-[2-(tert-Butyldimethylsilanyloxy)-2,2-dithiophen-2-ylacetoxy]-9-{2-[(4-{[(R)-(tert-butyl-dimethylsilanyl-oxy)-2-(8-hydroxy-2-oxo-1,2-dihydroquinolin-5-yl)ethylamino]methyl}-benzenesulfonyl)methylamino]ethyl}-9-methyl-3-oxa-9-azoniatricyclo[3.3.1.0$^{2,4}$]nonane A solution of the product of Preparation 6 (293 mg, 0.74 mmol) and the product of Preparation 40 in dichloromethane and methanol (6.2 mL, 1/1) is stirred at room temperature for 1 h and then sodium triacetoxyborohydride (394 mg, 1.86 mmol) is added. The reaction mixture is stirred for 4 h and then the solvent is removed under reduced pressure and the resulting crude residue is purified by flash chromatography to give the title intermediate.

Example 12

7-(2-Hydroxy-2,2-dithiophen-2-ylacetoxy)-9-{2-[(4-{[(R)-2-hydroxy-2-(8-hydroxy-2-oxo-1,2-dihydroquinolin-5-yl)ethylamino]methyl}benzenesulfonyl)methylamino]-ethyl}-9-methyl-3-oxa-9-azoniatricyclo[3.3.1.0$^{2,4}$]nonane A stirred solution of the product of Preparation 41 (0.62 mmol) in 1M hydrochloric acid (5 mL) and acetonitrile (5 mL) is heated at 60° C. for 8 h. The reaction mixture is cooled to room temperature and the solvent is removed under reduced pressure. The crude residue is purified by preparative HPLC to give the title compound as the ditrifluoroacetate salt.

Preparation 42

(3-Aminomethylphenyl)methanol Hydrochloride (a) (3-tert-Butoxycarbonylmethylphenyl)methanol Borane dimethyl sulfide (2.05 mL, 21.6 mmol) was added to a solution of 3-(tert-butoxycarbonylaminomethyl)benzoic acid (1.81 g, 7.20 mmol) in tetrahydrofuran (24 mL). and the resulting mixture was stirred at room temperature for 3 hours. The reaction mixture was then diluted with ethyl acetate (20 mL) and the layers were separated. The organic layer was washed with saturated sodium bicarbonate, saturated sodium chloride, dried over magnesium sulfate and concentrated to give the title compound as a yellow oil (1.71 g).

(b) (3-Aminomethylphenyl)methanol Hydrochloride

To the product of step (a) (1.71 g, 7.2 mmol) was added a solution of 4 M hydrochloric acid in dioxane (9 mL, 36 mmol) and the resulting mixture was stirred at room temperature for 1 h. The reaction mixture was then concentrated and the residue was diluted with diethyl ether (50 mL) and filtered to provide the title compound as a white solid (1.09 g).

Preparation 43

7-[2-(tert-Butyldimethylsilanyloxy)-2,2-dithiophen-2-ylacetoxy]-9-{2-[3-(3-hydroxymethylbenzyl)ureido]-ethyl}-9-methyl-3-oxa-9-azoniatricyclo[3.3.1.0$^{2,4}$]nonane A 0.2 M solution of the product of Preparation 23 (2.24 mmol) in N,N-dimethylformamide is added dropwise to a solution of 1,1'-carbonyldiimidazole (364 mg, 2.24 mmol) and diisopropylethylamine (0.31 mL, 2.24 mmol) in N,N-dimethylformamide (11 mL) and the resulting mixture is stirred at room temperature for 2 h. Diisopropylethylamine (0.31 mL, 2.24 mmol) and the product of Preparation 42 (578 mg, 3.4 mmol) are added and this mixture is stirred at 50° C. for 12 hours. The reaction mixture is then concentrated to dryness and the residue is purified by flash chromatography to give the title intermediate.

Preparation 44

9-{2-[3-(3-Formylbenzyl)ureido]ethyl}-7-[2-(tert-butyldimethylsilanyloxy)-2,2-dithiophen-2-ylacetoxy]-9-methyl-3-oxa-9-azoniatricyclo[3.3.1.0$^{2,4}$]nonane A solution of the product of Preparation 43 (2.23 mmol) in dichloromethane (11.1 mL) is cooled to 0° C. and diisopropylethylamine (1.17 mL, 6.70 mmol) and dimethyl sulfoxide (0.949 mL, 13.4 mmol) are added. After about 10 minutes, pyridine sulfur trioxide complex (1.06 g, 6.70 mmol) is added and the resulting mixture is stirred at 0° C. for 2 h. The reaction mixture is then concentrated to dryness and the residue is purified by flash chromatography to give the title intermediate.

Preparation 45

7-[2-(tert-Butyldimethylsilanyloxy)-2,2-dithiophen-2-ylacetoxy]-9-{2-[3-(3-{[(R)-2-(tert-butyl-dimethylsilanyloxy)-2-(8-hydroxy-2-oxo-1,2-dihydroquinolin-5-yl)ethylamino]-methyl}benzyl)ureido]ethyl}-9-methyl-3-oxa-9-azoniatricyclo[3.3.1.0$^{2,4}$]nonane The product of Preparation 6 (575 mg, 1.40 mmol) is added to a solution of the product of Preparation 44 (1.2 mmol) and diisopropylamine (0.25 mL, 1.40 mmol) in dichloromethane (6 mL) and the resulting mixture is stirred at room temperature for 45 min. Sodium triacetoxyborohydride (385 mg, 1.80 mmol) is then added and this mixture is stirred at room temperature for 12 h. The reaction mixture is then concentrated to dryness and the residue is purified by flash chromatography to give the title intermediate.

Example 13

7-(2-Hydroxy-2,2-dithiophen-2-yl-acetoxy)-9-{2-[3-(3-{[(R)-2-hydroxy-2-(8-hydroxy-2-oxo-1,2-dihydroquinolin-5-yl)ethylamino]methyl}benzyl)ureido]ethyl}-9-methyl-3-oxa-9-azoniatricyclo[3.3.1.0$^{2,4}$]nonane Triethylamine trihydrofluoride (2.4 mL, 13.6 mmol) is added to a solution of the product of Preparation 44 (1.36 mmol) in dichloromethane (2 mL) and the resulting mixture is stirred at room temperature for 15 h. The reaction mixture is then concentrated under vacuum to dryness and the residue is dissolved in a 1:1 mixture of water and acetonitrile with 0.1% TFA and this mixture is purified by HPLC to provide the title compound as the ditrifluoroacetate salt.

Preparation 46

7-[2-(tert-Butyldimethylsilanyloxy)-2,2-dithiophen-2-ylacetoxy]-9-methyl-9-[3-(4-nitrophenyl)allyl]-3-oxa-9-azoniatricyclo[3.3.1.0$^{2,4}$]nonane A stirred solution of the product of Preparation 8 (0.5 mmol), 1-((E)-4-chlorobut-1-enyl)-4-nitrobenzene (1 mmol) and cesium carbonate (244 mg, 0.75 mmol) in DMF (2.5 mL) is heated at 70° C. for 24 h. The reaction mixture was allowed to cool and the solvent is removed under reduced pressure. The crude product is used without further purification.

Preparation 47

9-[3-(4-Aminophenyl)propyl]-7-[2-(tert-butyldimethylsilanyloxy)-2,2-dithiophen-2-ylacetoxy]-9-methyl-3-oxa-9-azoniatricyclo[3.3.1.0$^{2,4}$]nonane The product of Preparation 46 (5.4 mmol) is dissolved in 100 mL of ethanol and the resulting solution is purged with nitrogen for 30 min. Palladium on carbon (2.5 g; 50% w/w water; 10% Pd; 1.1 mmol Pd) is then added while degassing with nitrogen. This mixture is then placed under hydrogen (50 psi) until hydrogen is no longer consumed (~30 minutes). The mixture is then purged with nitrogen, filtered through Celite and concentrated. The residue is purified by flash chromatography to give the title intermediate.

Preparation 48

7-[2-(tert-Butyldimethylsilanyloxy)-2,2-dithiophen-2-ylacetoxy]-9-{3-[4-(4-{2-[(R)-2-(tert-butyldimethylsilanyloxy)-2-(8-benzyloxy-2-oxo-1,2-dihydroquinolin-5-yl)ethylamino]-ethyl}phenylamino)phenyl]propyl}-9-methyl-3-oxa-9-azoniatricyclo[3.3.1.0$^{2,4}$]nonane To a 25 mL round-bottomed flask is added the product of Preparation 47 (0.8 mmol); 8-benzyloxy-5-[(R)-2-[2-(4-bromophenyl)ethylamino]-1-(tert-butyldimethylsilanyloxy)ethyl]-1H-quinolin-2-one (769 mg, 1.2 mmol); tris(dibenzylideneacetone)dipalladium(0) (73 mg, 0.08 mmol, 20% Pd); and 2-(dicyclohexylphosphino)biphenyl (84 mg, 0.24 mmol). This mixture is purged with nitrogen and then dry, degassed toluene (8 mL, 0.1 M) is added and the resulting mixture is heated at 70° C. for 30 min. Sodium tert-butoxide (382 mg, 4.0 mmol) is then added, and the temperature is raised to 95° C. for 4 h. The reaction mixture is then cooled to room temperature and diluted with ethyl acetate. This mixture is then concentrated to dryness and the residue is purified by flash chromatography to give the title intermediate.

Example 14

7-(2-Hydroxy-2,2-dithiophen-2-ylacetoxy)-9-{3-[4-(4-{2-[(R)-2-hydroxy-2-(8-hydroxy-2-oxo-1,2-dihydroquinolin-5-yl)ethylamino]ethyl}phenylamino)phenyl]propyl}-9-methyl-3-oxa-9-azoniatricyclo[3.3.1.0$^{2,4}$]nonane Using the product of Preparation 48 and following the procedures described in Preparation 21 and Example 4, the title compound is prepared as the ditrifluoroacetate salt.

Preparation 49

9-[2-Fluoro-3-(4-hydroxymethylpiperidin-1-ylmethyl)benzyl]-7-[2-(tert-butyldimethylsilanyloxy)-2,2-dithiophen-2-ylacetoxy]-9-methyl-3-oxa-9-azoniatricyclo[3.3.1.0$^{2,4}$]nonane The product of Preparation 8 (1.69 mmol), 2,6-bis(bromomethyl)-1-fluorobenzene (476 mg, 1.69 mmol, piperidin-4-ylmethanol (195 mg, 1.69 mmol) and potassium carbonate (466 mg, 3.37 mmol) are suspended in acetonitrile (5 mL) and stirred at room temperature for 18 h. The reaction mixture is then concentrated and the residue purified by flash chromatography to give the title compound.

Preparation 50

9-[2-Fluoro-3-(4-formylpiperidin-1-ylmethyl)benzyl]-7-[2-(tert-butyldimethylsilanyloxy)-2,2-dithiophen-2-ylacetoxy]-9-methyl-3-oxa-9-azoniatricyclo[3.3.1.$0^{2,4}$]nonane The product of Preparation 49 (0.53 mmol) is dissolved in dichloromethane and to this mixture is added diisopropylethylamine (280 μL, 1.6 mmol) and dimethyl sulfoxide (115 μL, 1.6 mmol). The reaction mixture is cooled to −15° C. under nitrogen and pyridine sulfur trioxide complex (255 mg, 1.6 mmol) is added and the resulting mixture is stirred for 40 min. The reaction mixture is then concentrated and the residue purified by flash chromatography to give the title compound.

Example 15

9-[2-Fluoro-3-(4-{[(R)-2-hydroxy-2-(8-hydroxy-2-oxo-1,2-dihydroquinolin-5-yl)-ethylamino]methyl}piperidin-1-ylmethyl)benzyl]-7-(2-hydroxy-2,2-dithiophen-2-yl-acetoxy)-9-methyl-3-oxa-9-azoniatricyclo[3.3.1.$0^{2,4}$]nonane The product of Preparation 50 (0.48 mmol) is dissolved in a 1:1 mixture of dichloromethane and methanol (6 mL) and to this mixture is added the product of Preparation 6 (228 mg, 0.58 mmol) and sodium triacetoxyborohydride (317 mg, 1.5 mmol). The reaction mixture is stirred under nitrogen at room temperature for 18 h and then concentrated. The residue is dissolved in a 2:3 mixture of acetonitrile and aqueous 6 N hydrochloric acid, and this mixture is heated at 55° C. for 4 hours. The reaction mixture is then concentrated and the residue is dissolved in water/acetonitrile/trifluoroacetic acid (1:1:0.005) and purified by reverse phase column chromatography to afford the title compound as the ditrifluoroacetate salt.

Preparation 51

2-[4-(3-Bromopropoxy)phenyl]ethanol

To a solution of 4-hydroxyphenethyl alcohol (4.37 g, 31.0 mmol) and potassium carbonate (6.55 g, 47.0 mmol) in acetonitrile (62.0 mL) was added 1,3 dibromopropane (31.0 mL, 316 mmol). The reaction mixture was heated to 70° C. for 12 hours and then cooled to room temperature, filtered and concentrated under vacuum. The resulting oil was purified by silica gel chromatography using a mixture of 4:1 hexanes and ethyl acetate to give the title compound (6.21 g) as a white solid.

Preparation 52

7-[2-(tert-Butyldimethylsilanyloxy)-2,2-dithiophen-2-ylacetoxy]-9-{3-[4-(2-hydroxyethyl)phenoxy]propyl}-9-methyl-3-oxa-9-azoniatricyclo[3.3.1.$0^{2,4}$]nonane To a solution of the product of Preparation 51 (1.11 g, 4.30 mmol) and diisopropylethylamine (0.90 mL, 5.10 mmol) in acetonitrile (21.5 mL) is added the product of Preparation 8 (4.30 mmol) and the resulting mixture is stirred at 60° C. for 12 h. The reaction mixture is then concentrated and the residue purified by flash chromatography to give the title compound.

Preparation 53

7-[2-(tert-Butyldimethylsilanyloxy)-2,2-dithiophen-2-ylacetoxy]-9-methyl-9-{3-[4-(2-oxoethyl)phenoxy]-propyl}-3-oxa-9-azoniatricyclo[3.3.1.$0^{2,4}$]nonane A solution of the product of Preparation 52 (1.53 mmol) and dichloromethane (75 mL) is cooled to about 5° C. and diisopropylethylamine (798 mL, 4.58 mmol) and dimethyl sulfoxide (649 mL, 9.15 mmol) are added. Pyridine sulfur trioxide (728 mg, 4.58 mmol) is then added and the resulting mixture is stirred at 5° C. for 45 min. The reaction mixture is then concentrated and the residue is purified by flash chromatography to give the title compound.

Preparation 54

7-[2-(tert-Butyldimethylsilanyloxy)-2,2-dithiophen-2-ylacetoxy]-9-[3-(4-{2-[(R)-2-(tert-butyl-dimethylsilanyloxy)-2-(8-hydroxy-2-oxo-1,2-dihydroquinolin-5-yl)ethylamino]-ethyl}phenoxy)propyl]-9-methyl-3-oxa-9-azoniatricyclo[3.3.1.$0^{2,4}$]nonane The product of Preparation 53 (1.28 mmol) is dissolved in methanol (6.4 mL) and the product of Preparation 6 (605 mg, 1.53 mmol) and diisopropylethylamine (0.27 mL, 1.53 mmol) are added. Sodium triacetoxyborohydride (405 mg, 1.91 mmol) is then added and the reaction mixture is stirred at room temperature for 3 h. The reaction mixture is then concentrated to dryness and the residue is purified by flash chromatography to give the title compound.

Example 16

7-(2-Hydroxy-2,2-dithiophen-2-ylacetoxy)-9-[3-(4-{2-[(R)-2-hydroxy-2-(8-hydroxy-2-oxo-1,2-dihydroquinolin-5-yl)ethylamino]ethyl}phenoxy)propyl]-9-methyl-3-oxa-9-azoniatricyclo[3.3.1.$0^{2,4}$]nonane Triethylamine trihydrofluoride (1.5 mL, 8.87 mmol) is added to a solution of the product of Preparation 54 (0.89 mmol) in dichloromethane (4.5 mL) and the resulting mixture is stirred at room temperature for 24 h. The mixture is then concentrated under vacuum and purified by HPLC to give the title compound as the ditrifluoroacetate salt.

Preparation 55

Methyl 4-Iodophenylacetate

To a stirred solution of 4-iodophenylacetic acid (5.0 g, 19.1 mmol) in MeOH (200 mL) was added 4N hydrochloric acid in dioxane (10 mL). The reaction mixture was stirred for 24 h at room temperature and then the solvent was removed under reduced pressure to give the title compound (5.17 g, 98% yield), which was used without further purification.

Preparation 56

Methyl [4-(4-Hydroxybut-1-ynyl)phenyl]acetate

To a stirred solution of the product of Preparation 55 (4.5 g, 16.3 mmol) in diethylamine (100 mL) was added but-3-yn-1-ol (1.9 mL, 32.6 mmol), $Pd(PPh_3)_2Cl_2$ (500 mg, 1.63 mmol) and CuI (154 mg, 0.815 mmol) and resulting mixture was stirred for 17 h at room temperature. The solvent was then removed under reduced pressure and the residue was dissolved in diethyl ether (200 mL) and this solution was filtered to remove salts. The solvent was then removed under reduced pressure and the crude product was purified by silica gel chromatography (60% EtOAc/Hexane) to afford the title intermediate (3.03 g, 91% yield).

Preparation 57

Methyl [4-(4-Hydroxybutyl)phenyl]acetate

A stirred solution of the product of Preparation 56 (2.8 g, 12.8 mmol) in methanol (50 mL) was flushed with nitrogen and then 10% palladium on carbon (400 mg, 20% wt/wt) was added. The reaction flask was then alternately placed under vacuum and flushed with hydrogen for cycles and then stirred under hydrogen for 14 h. The reaction mixture was flushed with nitrogen and then filtered and the solvent removed under reduced pressure to give the title compound (2.75 g, 97% yield), which was used without further purification.

Preparation 58

7-[2-(tert-Butyldimethylsilanyloxy)-2,2-dithiophen-2-ylacetoxy]-9-[4-(4-methoxycarbonylmethylphenyl)-butyl]-9-methyl-3-oxa-9-azoniatricyclo[3.3.1.0$^{2,4}$]nonane (a) Methyl {4-[4-(Toluene-4-sulfonyloxy)butyl]phenyl}acetate To a stirred solution of the product of Preparation 57 (2.6 g, 12.5 mmol) in THF (100 mL) was added DABCO (2.6 g, 25.0 mmol) and then p-toluenesulfonyl chloride (2.44 g, 13.75 mmol). The reaction mixture was stirred at room temperature for 23 h and then solvent was removed under reduced pressure and the residue was dissolved in dichloromethane (200 mL). The organic layer was then washed with water (2×100 mL), 1N hydrochloric acid (100 mL), aqueous saturated sodium chloride solution (100 mL), dried ($MgSO_4$), filtered and the solvent removed under reduced pressure to give the title compound, which was used without further purification.

(b) 7-[2-(tert-Butyldimethylsilanyloxy)-2,2-dithiophen-2-ylacetoxy]-9-[4-(4-methoxycarbonylmethylphenyl)butyl]-9-methyl-3-oxa-9-azoniatricyclo[3.3.1.0$^{2,4}$]nonane To the crude product from step (a) is added DMF (50 mL), diisopropylethylamine (3.0 mL, 17.3 mmol) and the product of Preparation 8 (8.1 mmol). The reaction mixture is stirred at room temperature for 18 h and then the solvent is removed under reduced pressure to give the title compound.

Preparation 59

7-[2-(tert-Butyldimethylsilanyloxy)-2,2-dithiophen-2-ylacetoxy]-9-{4-[4-(2-hydroxyethyl)phenyl]butyl}-9-methyl-3-oxa-9-azoniatricyclo[3.3.1.0$^{2,4}$]nonane To a stirred solution of the product of Preparation 58 (4.0 mmol) in THF (100 mL) is added dropwise DIBAL-H (24 mL, 24 mmol, 1.0 M in THF). After the addition is complete, the reaction mixture is stirred for 3 h and then quenched by slow addition of methanol (until gas evolution ceased). The mixture is then concentrated to dryness and the residue is purified by flash chromatography to give the title compound.

Preparation 60

7-[2-(tert-Butyldimethylsilanyloxy)-2,2-dithiophen-2-ylacetoxy]-9-{4-[4-(2-oxoethyl)phenyl]butyl}-9-methyl-3-oxa-9-azoniatricyclo[3.3.1.0$^{2,4}$]nonane To a stirred solution of the product of Preparation 59 (1.06 mmol) in dichloromethane (25 mL) is added dimethyl sulfoxide (0.60 mL, 10.6 mmol) and diisopropylethylamine (0.921 mL, 5.3 mmol). The reaction mixture is then cooled to −10° C. and pyridine sulfur trioxide (842 mg, 5.3 mmol) is added. The reaction mixture is stirred for 1 h and then concentrated to dryness and the residue is purified by flash chromatography to give the title compound.

Example 17

7-[2-(tert-Butyldimethylsilanyloxy)-2,2-dithiophen-2-ylacetoxy]-9-[4-(4-{2-[(R)-2-hydroxy-2-(8-hydroxy-2-oxo-1,2-dihydroquinolin-5-yl)ethylamino]ethyl}phenyl)-butyl]-9-methyl-3-oxa-9-azoniatricyclo[3.3.1.0$^{2,4}$]nonane The product of Preparation 60 (1.28 mmol) is dissolved in methanol (6.4 mL) and the product of Preparation 6 (605 mg, 1.53 mmol) and diisopropylethylamine (0.27 mL, 1.53 mmol) are added. Sodium triacetoxyborohydride (405 mg, 1.91 mmol) is then added and the reaction mixture is stirred at room temperature for 3 h. The reaction mixture is then concentrated to dryness. To the residue is added dichloromethane (4.5 mL) and triethylamine trihydrofluoride (1.5 mL, 8.87 mmol) and the resulting mixture is stirred at room temperature for 24 h. The mixture is then concentrated under vacuum and purified by HPLC to give the title compound as the ditrifluoroacetate salt.

Preparation 61

Ethyl 3-[5-(2-Ethoxycarbonylvinyl)thiophen-2-yl]acrylate

To a stirred solution of sodium hydride (2.1 g, 53 mmol, 60% in mineral oil) in THF (200 mL) was slowly added triethylphosphonoacetate (10 mL, 50 mmol) Hydrogen gas evolution was observed and the reaction was stirred until gas evolution ceased (about 30 min). To this reaction mixture was added 2,5-thiophenedicarboxaldehyde (3 g, 21 mmol) and the reaction mixture was stirred for 1 h. The solvent was removed under reduced pressure and the residue was dissolved in dichloromethane (200 mL). The organic layer was washed with water (100 mL), aqueous 1N hydrochloric acid (100 mL), aqueous saturated sodium chloride solution (100 mL), dried ($MgSO_4$), filtered and the solvent removed under reduced pressure to give the title compound (5.8 g, 98% yield), which was used without further purification.

Preparation 62

Ethyl 3-[5-(2-Ethoxycarbonylethyl)thiophen-2-yl]propionate

A stirred solution of the product of Preparation 61 (5.8 g, 21 mmol) in methanol (200 mL) was flushed with nitrogen and 10% palladium on carbon (576 mg, 10% wt/wt) was added. The reaction flask was alternately placed under vacuum and flushed with hydrogen for 3 cycles and then the reaction mixture was stirred under hydrogen for 1 h. The mixture was then flushed with nitrogen, filtered and the solvent removed under reduced pressure to give the title compound (5.8 g, 99% yield), which was used without further purification.

Preparation 63

3-[5-(3-Hydroxypropyl)thiophen-2-yl]propan-1-ol

To a stirred solution of DIBAL-H (88 mL, 88 mmol, 1.0M in cyclohexane) in THF (300 mL) at −78° C. was added dropwise the product of Preparation 62 (5.0 g, 17.6 mmol). After the addition was complete, the reaction mixture was warmed to room temperature over 30 min and then quenched by slow addition of aqueous 1N hydrochloric acid (200 mL). Dichloromethane (400 mL) was added and the layers were separated. The aqueous layer was washed with dichloromethane (4×100 mL) and the combined organic layers were washed with aqueous saturated sodium chloride solution (100 mL), dried ($MgSO_4$), filtered and the solvent removed under reduced pressure to give the title compound (3.0 g, 85% yield), which was used without further purification.

Preparation 64

7-[2-(tert-Butyldimethylsilanyloxy)-2,2-dithiophen-2-ylacetoxy]-9-{3-[5-(3-hydroxypropyl)thiophen-2-yl]-propyl}-9-methyl-3-oxa-9-azoniatricyclo[3.3.1.0$^{2,4}$]nonane (a) Toluene-4-sulfonic Acid 3-[5-(3-Hydroxypropyl)thiophen-2-yl]propyl Ester To a stirred solution of the product of Preparation 63 (423 mg, 2.1 mmol) in THF (20 mL) was added DABCO (420 mg, 4.2 mmol) and then p-toluenesulfonyl chloride (442 mg, 2.3 mmol). The reaction mixture was stirred at room temperature for 2 h and then the solvent was removed under reduced pressure and the residue was dissolved in dichloromethane (200 mL). The organic layer was washed with water (2×100 mL), aqueous saturated sodium chloride solution (100 mL), dried $MgSO_4$), filtered and the solvent removed under reduced pressure to give the title compound, which was used without further purification.

(b) 7-[2-(tert-Butyldimethylsilanyloxy)-2,2-dithiophen-2-ylacetoxy]-9-{3-[5-(3-hydroxypropyl)-thiophen-2-yl]-propyl}-9-methyl-3-oxa-9-azoniatricyclo[3.3.1.0$^{2,4}$]nonane To the product from step (a) is added acetonitrile (20 mL), diisopropylethylamine (0.5 mL, 2.8 mmol) and the product of Preparation 8 (2.11 mmol). The reaction mixture is heated to 50° C. for 20 h and then cooled to room temperature and the solvent is removed under reduced pressure. The residue is purified by flash chromatography to afford the title compound.

Preparation 65

7-[2-(tert-Butyldimethylsilanyloxy)-2,2-dithiophen-2-ylacetoxy]-9-{3-[5-(3-oxopropyl)-thiophen-2-yl]-propyl}-9-methyl-3-oxa-9-azoniatricyclo[3.3.1.0$^{2,4}$]nonane To a stirred solution of the product of Preparation 64 (0.94 mmol) in dichloromethane (20 mL) is added dimethyl sulfoxide (0.21 mL, 3.7 mmol) and diisopropylethylamine (0.65 mL, 3.7 mmol). This mixture is cooled to −10° C. and pyridine sulfur trioxide (444 mg, 2.8 mmol) is added. The reaction mixture is stirred for 3 h and then concentrated to dryness and the residue is purified by flash chromatography to give the title compound.

Example 18

7-(2-Hydroxy-2,2-dithiophen-2-ylacetoxy)-9-[3-(5-{3-[(R)-2-hydroxy-2-(8-hydroxy-2-oxo-1,2-dihydroquinolin-5-yl)ethylamino]propyl}thiophen-2-yl)propyl]-9-methyl-3-oxa-9-azoniatricyclo[3.3.1.0$^{2,4}$]nonane The product of Preparation 65 (1.28 mmol) is dissolved in methanol (6.4 mL) and the product of Preparation 6 (605 mg, 1.53 mmol) and diisopropylethylamine (0.27 mL, 1.53 mmol) are added. Sodium triacetoxyborohydride (405 mg, 1.91 mmol) is then added and the reaction mixture is stirred at room temperature for 3 h. The reaction mixture is then concentrated to dryness. To the residue is added dichloromethane (4.5 mL) and triethylamine trihydrofluoride (1.5 mL, 8.87 mmol) and the resulting mixture is stirred at room temperature for 24 h. The mixture is then concentrated under vacuum and purified by HPLC to give the title compound as the ditrifluoroacetate salt.

Examples 19-149

Using the methods described above and the appropriate starting materials, the compounds of Examples 19 to 149 as shown in Table I are prepared.

Preparation 66

N-{2-Benzyloxy-5-[(R)-2-bromo-1-(tert-butyldimethylsilanyloxy)ethyl]phenyl}-formamide (R)-2-Bromo-1-(3-formamido-4-benzyloxyphenyl)ethanol (9.9 g, 28 mmol) was dissolved in dimethylformamide (36 mL). Imidazole (2.3 g, 34 mmol) and tert-butyldimethylsilyl chloride (4.7 g, 31 mmol) were added. The solution was stirred under nitrogen atmosphere for 72 h. Additional imidazole (0.39 g, 5.7 mmol) and tent-butyldimethylsilyl chloride (0.64 g, 4.3 mmol) were added and the reaction was stirred for an additional 20 h. The reaction mixture was then diluted with a mixture of isopropyl acetate (53 mL) and hexanes (27 mL) and transferred to a separatory funnel. The organic layer was washed twice with a mixture of water (27 mL) and saturated aqueous sodium chloride (27 mL) followed by a final wash with saturated aqueous sodium chloride (27 mL). The organic layer was dried over sodium sulfate. Silica gel (23.6 g) and hexanes (27 mL) were added and the suspension was stirred for 10 min. The solids were removed by filtration and the filtrate concentrated under vacuum. The residue was crystallized from hexanes (45 mL) to afford 8.85 g (19 mmol, 68%) of the title compound as a solid. MS m/z: [M+H$^+$] calcd for $C_{22}H_{30}NO_3SiBr$ 464.1; found 464.2.

The starting material, (R)-2-bromo-1-(3-formamido-4-benzyloxyphenyl)ethanol, can be prepared as described in U.S. Pat. No. 6,268,533 B1; or R. Hett et al., *Organic Process Research and Development,* 1998, 2:96-99; or using procedures similar to those described in Hong et al., *Tetrahedron Lett.,* 1994, 35:6631; or similar to those described in U.S. Pat. No. 5,495,054.

Preparation 67

9-{9-[2-(4-Benzyloxy-3-formylaminophenyl)-2-((R)-tert-butyldimethylsilanyloxy)-ethylamino]nonyl}-7-(2-hydroxy-2,2-dithiophen-2-ylacetoxy)-9-methyl-3-oxa-9-azoniatricyclo[3.3.1.0$^{2,4}$]nonane A stirred solution of the product of Preparation 2 (292 mg, 0.5 mmol), the product of Preparation 66 (1 mmol) and cesium carbonate (244 mg, 0.75 mmol) in DMF (2.5 mL) is heated at 70° C. for 24 h. The reaction mixture is allowed to cool and the solvent is removed under reduced pressure. The crude product is used without further purification.

Preparation 68

9-{9-[(R)-2-(4-Benzyloxy-3-formylaminophenyl)-2-hydroxyethylamino]nonyl}-7-(2-hydroxy-2,2-dithiophen-2-ylacetoxy)-9-methyl-3-oxa-9-azonia-tricyclo[3.3.1.0$^{2,4}$]nonane Triethylamine trihydrofluoride (163 μL, 1 mmol) is added to a stirred solution of the product of Preparation 67 (0.5 mmol) in DCM (5 mL) and DMF (3 mL). The reaction mixture is stirred at ambient temperature for 24 h and then the solvent is removed under reduced pressure. The crude residue is purified by flash chromatography to afford the title compound.

Example 150

9-{9-[(R)-2-(3-Formylamino-4-hydroxyphenyl)-2-hydroxyethylamino]nonyl}-7-(2-hydroxy-2,2-dithiophen-2-ylacetoxy)-9-methyl-3-oxa-9-azonia-tricyclo[3.3.1.0$^{2,4}$]nonane Palladium (10 wt. % (dry basis) on activated carbon) (124 mg) is added to a stirred solution of the product of Preparation 67 (0.44 mmol) in ethanol (4 mL) and the reaction mixture is placed under an atmosphere of hydrogen. After stirring for 12 h, the reaction mixture is filtered through a pad of Celite, washed with methanol (2 mL) and the solvent is removed under reduced pressure. The resulting residue is purified by preparative HPLC to give the title compound as the ditrifluoroacetate salt.

Examples 151-299

Using the methods described above and the appropriate starting materials, the compounds of Examples 151 to 299 as shown in Table II are prepared.

Preparation 69

6-(2-Bromo-(R)-1-tert-butyldimethylsilyloxy)ethyl-2,2-dimethyl-1,3-benzodioxan (a) 6-Bromo-2,2-dimethyl-4H-benzo[1,3]dioxine To 5-bromo-2-hydroxybenzyl alcohol (93 g, 0.46 mol, available from Sigma-Aldrich) in 2.0 L of 2,2-dimethoxypropane was added 700 mL of acetone, followed by zinc chloride (170 g). After stirring for 18 hours, 1.0 M aqueous sodium hydroxide was added until the aqueous phase was basic. Diethyl ether (1.5 L) was added to the slurry and the organic phase was decanted into a separatory funnel. The organic phase was washed with brine, dried over $Na_2SO_4$, filtered and concentrated under reduced pressure to give the title compound as an oil.

(b) 6-Acetyl-2,2-dimethyl-4,1-benzo[1,3]dioxine

To the product of step (a) (110 g, 0.46 mol) in 1.0 L of THF at −78° C. was added 236 mL (0.51 mol) of 2.14 M n-butyllithium in hexanes via a dropping funnel. After 30 minutes, N-methyl-N-methoxy acetamide (71 g, 0.69 mol, available from TCI) was added. After 2 hours, the reaction mixture was quenched with water, diluted with 2.0 L of 1.0 M aqueous phosphate buffer (pH=7.0) and extracted once with diethyl ether. The diethyl ether phase was washed once with brine, dried over $Na_2SO_4$, filtered and concentrated under reduced pressure to give a light orange oil. The oil was dissolved in a minimum volume of ethyl acetate, diluted with hexanes, and to give the title compound as a crystalline solid.

(c) 6-Bromoacetyl-2,2-dimethyl-4H-benzo[1,3]dioxine

To the product of step (b) (23.4 g, 0.113 mol) in 600 mL of THF at −78° C. was added 135 mL of 1.0 M sodium hexamethyldisilazane in THF (Sigma-Aldrich). After 1 hour, trimethylsilyl chloride (15.8 mL, 0.124 mol) was added. After another 30 minutes, bromine (5.82 mL, 0.113 mol) was added. After 10 minutes, the reaction was quenched by diluting the reaction mixture with diethyl ether and pouring it onto 500 mL of 5% aqueous $Na_2SO_3$ premixed with 500 mL of 5% aqueous $NaHCO_3$. The phases were separated and the organic phase was washed with brine, dried over $Na_2SO_4$, filtered and concentrated under reduced pressure to give the title compound as an oil that solidified upon storage in the freezer.

(d) (R)-2-Bromo-1-(2,2-dimethyl-4,1-benzo[1,3]dioxin-6-yl)ethanol

To the product of step (c) (10 g, 35.1 mmol) in 100 mL of THF was added the solid catalyst of Preparation 13, step (c)(1) (0.97 g, 3.5 mmol). The solution was cooled to between −20° C. and −10° C. and $BH_3$-THF (35 mL, 35 mmol) diluted with 50 mL THF was added dropwise via a dropping funnel. After the addition was complete, the reaction mixture was allowed to warm to ambient temperature. After 30 minutes, the reaction mixture was quenched by slow addition of 50 mL of methanol and then concentrated to a thick oil. The oil was purified by silica gel chromatography eluted with 1:2 ethyl acetate/hexanes. The fractions were combined and concentrated to give the title compound as an off-white solid.

(e) [(R)-2-Bromo-1-(2,2-dimethyl-4H-benzo[1,3]dioxin-6-yl)ethoxy]-tert-butyldimethylsilane To the product of step (d) (10 g, 34.8 mmol) and imidazole (4.7 g, 69.7 mmol) dissolved in 100 mL DMF was added tert-butyldimethylsilyl chloride (5.78 g, 38.3 mmol). The reaction mixture was stirred for 18 hours. The reaction mixture was then partitioned between 200 mL of saturated sodium chloride and 200 mL of diethyl ether. The aqueous layer was extracted with 200 mL of diethyl ether. The organic layers were then combined, washed with saturated sodium chloride (3×100 mL), dried over $MgSO_4$ and concentrated. The product was purified by silica gel chromatography, eluting with hexanes followed by 5% ethyl acetate in hexanes. The desired fractions were combined and concentrated to give the title compound as an oil.

Preparation 70

9-{9-[(R)-2-(tert-Butyldimethylsilanyloxy)-2-(2,2-dimethyl-4H-benzo[1,3]dioxin-6-yl)-ethylamino]-nonyl}-7-(2-hydroxy-2,2-dithiophen-2-ylacetoxy)-9-methyl-3-oxa-9-azoniatricyclo[3.3.1.0$^{2,4}$]nonane A stirred solution of the product of Preparation 2 (292 mg, 0.5 mmol), the product of Preparation 69 (1 mmol) and cesium carbonate (244 mg, 0.75 mmol) in DMF (2.5 mL) is heated at 70° C. for 24 h. The reaction mixture is allowed to cool and the solvent is removed under reduced pressure. The crude product is used without further purification.

Preparation 71

9-{9-[(R)-2-(2,2-Dimethyl-4H-benzo[1,3]dioxin-6-yl)-2-hydroxyethylamino]nonyl}-7-(2-hydroxy-2,2-dithiophen-2-ylacetoxy)-9-methyl-3-oxa-9-azonia-tricyclo[3.3.1.0$^{2,4}$]nonane Triethylamine trihydrofluoride (163 μL, 1 mmol) is added to a stirred solution of the product of Preparation 70 (0.5 mmol) in DCM (5 mL) and DMF (3 mL). The reaction mixture is stirred at ambient temperature for 24 h and then the solvent is removed under reduced pressure. The crude residue is purified by flash chromatography to afford the title compound.

Example 300

7-(2-Hydroxy-2,2-dithiophen-2-ylacetoxy)-9-{9-[(R)-2-hydroxy-2-(4-hydroxy-3-hydroxymethylphenyl)ethylamino]nonyl}-9-methyl-3-oxa-9-azonia-tricyclo[3.3.1.0$^{2,4}$]nonane Trifluoroacetic acid (2.80 mL) is added to a stirred solution of the product of Preparation 71 (0.93 mmol) in THF/$H_2O$ (14 mL, 1:1) and the reaction mixture is stirred for 2 h at ambient temperature. The reaction mixture is concentrated under reduced pressure and dissolved in 20% MeCN/$H_2O$ then purified by preparative HPLC to yield the title compound.

Preparation A

Cell Culture and Membrane Preparation From Cells Expressing Human $\beta_1$, $\beta_2$ or $\beta_3$ Adrenergic Receptors Chinese hamster ovarian (CHO) cell lines stably expressing cloned human $\beta_1$, $\beta_2$ or $\beta_3$ adrenergic receptors, respectively, were grown to near confluency in Hams F-12 media with 10% FBS in the presence of 500 μg/mL Geneticin. The cell monolayer was lifted with 2 mM EDTA in PBS. Cells were pelleted by centrifugation at 1,000 rpm, and cell pellets were either stored frozen at −80° C. or membranes were prepared immediately for use. For preparation of $\beta_1$ and $\beta_2$ receptor expressing membranes, cell pellets were re-suspended in lysis buffer (10 mM HEPES/HCl, 10 mM EDTA, pH 7.4 at 4° C.) and homogenized using a tight-fitting Dounce glass homogenizer (30 strokes) on ice. For the more protease-sensitive $\beta_3$ receptor expressing membranes, cell pellets were homogenated in lysis buffer (10 mM Tris/HCl, pH 7.4) supplemented with one tablet of "Complete Protease Inhibitor Cocktail Tablets with 2 mM EDTA" per 50 mL buffer (Roche Catalog No. 1697498, Roche Molecular Biochemicals, Indianapolis, Ind.). The homogenate was centrifuged at 20,000×g, and the resulting pellet was washed once with lysis buffer by re-suspension and centrifugation as above. The final pellet was then re-suspended in ice-cold binding assay buffer (75 mM Tris/HCl pH 7.4, 12.5 mM $MgCl_2$, 1 mM EDTA). The protein concentration of the membrane suspension was determined by the methods described in Lowry et al., 1951, *Journal of Biological Chemistry,* 193, 265; and Bradford, Analytical Biochemistry, 1976, 72, 248-54. All membranes were stored frozen in aliquots at −80° C. or used immediately.

Preparation B

Cell Culture and Membrane Preparation From Cells Expressing Human $M_1$, $M_2$, $M_3$ and $M_4$ Muscarinic Receptors CHO cell lines stably expressing cloned human $hM_1$, $hM_2$, $hM_3$ and $hM_4$ muscarinic receptor subtypes, respectively, were grown to near confluency in HAM's F-12 media supplemented with 10% FBS and 250 μg/mL Geneticin. The cells were grown in a 5% $CO_2$, 37° C. incubator and lifted with 2 mM EDTA in dPBS. Cells were collected by 5 minute centrifugation at 650×g, and cell pellets were either stored frozen at −80° C. or membranes were prepared immediately for use. For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with re-suspension buffer and homogenized again with the Polytron tissue disrupter. The protein concentration of the membrane suspension was determined by the method described in Lowry et al., 1951, *Journal of Biochemistry,* 193, 265. All membranes were stored frozen in aliquots at −80° C. or used immediately. Aliquots of prepared $hM_5$ receptor membranes were purchased directly from Perkin Elmer and stored at −80° C. until use.

Assay Test Procedure A

Radioligand Binding Assay for Human $\beta_1$, $\beta_2$ and $\beta_3$ Adrenergic Receptors Binding assays were performed in 96-well microtiter plates in a total assay volume of 100 μL with 10-15 μg of membrane protein containing the human $\beta_1$, $\beta_2$ or $\beta_3$ adrenergic receptors in assay buffer (75 mM Tris/HCl pH 7.4 at 25° C., 12.5 mM $MgCl_2$, 1 mM EDTA, 0.2% BSA). Saturation binding studies for determination of $K_d$ values of the radioligand were done using [$^3$H]-dihydroalprenolol (NET-720, 100 Ci/mmol, PerkinElmer Life Sciences Inc., Boston, Mass.) for the $\beta_1$ and $\beta_2$ receptors and [$^{125}$I]-(−)-iodocyanopindolol (NEX-189, 220 Ci/mmol, PerkinElmer Life Sciences Inc., Boston, Mass.) at 10 or 11 different concentrations ranging from 0.01 nM to 20 nM. Displacement assays for determination of $K_i$ values of test compounds were done with [$^3$H]-dihydroalprenolol at 1 nM and [$^{125}$I]-(−)-iodocyanopindolol at 0.5 nM for 10 or 11 different concentrations of test compound ranging from 10 pM to 10 μM. Non-specific binding was determined in the presence of 10 μM propranolol. Assays were incubated for 1 hour at 37° C., and then binding reactions were terminated by rapid filtration over GF/B for the $\beta_1$ and $\beta_2$ receptors or GF/C glass fiber filter plates for the $\beta_3$ receptors (Packard BioScience Co., Meriden, Conn.) presoaked in 0.3% polyethyleneimine. Filter plates were washed three times with filtration buffer (75 mM Tris/HCl pH 7.4 at 4° C., 12.5 mM $MgCl_2$, 1 mM EDTA) to remove unbound radioactivity. The plates were then dried and 50 μL of Microscint-20 liquid scintillation fluid (Packard BioScience Co., Meriden, Conn.) was added and plates were counted in a Packard Topcount liquid scintillation counter (Packard BioScience Co., Meriden, Conn.). Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 μM propranolol. $K_i$ values for test compounds were calculated from observed $IC_{50}$ values and the $K_d$ value of the radioligand using the Cheng-Prusoff equation (Cheng Y, and Prusoff W H., *Biochemical Pharmacology,* 1973, 22, 23, 3099-108).

In this assay, a lower $K_i$ value indicates that a test compound has a higher binding affinity for the receptor tested. Exemplified compound of this invention that were tested in this assay typically were found to have a $K_i$ value of less than about 300 nM for the $\beta_2$ adrenergic receptor. For example, the compound of Example 1 was found to have $K_i$ value of less than 50 nM.

If desired, the receptor subtype selectivity for a test compound can be calculated as the ratio of $K_i(\beta_1)/K_i(\beta_2)$ or $K_i(\beta_3)/K_i(\beta_2)$. Typically, compounds of this invention demonstrated greater binding at the $\beta_2$ adrenergic receptor compared to the $\beta_1$ or $\beta_3$ adrenergic receptor, i.e. $K_i(\beta_1)$ or $K_i(\beta_3)$ is typically greater than $K_i(\beta_2)$. Generally, compounds having selectivity for the $\beta_2$ adrenergic receptor over the $\beta_1$ or $P_3$ adrenergic receptors are preferred; especially compounds having a selectivity greater than about 5. By way of example, the compound of Example 1 had a ratio of $K_i(\beta_1)/K_i(\beta_2)$ greater than 5.

Assay Test Procedure B

Radioligand Binding Assay for Muscarinic Receptors

Radioligand binding assays for cloned human muscarinic receptors were performed in 96-well microtiter plates in a total assay volume of 100 μL. CHO cell membranes stably expressing either the $hM_1$, $hM_2$, $hM_3$, $hM_4$ or $hM_5$ muscarinic subtype were diluted in assay buffer to the following specific target protein concentrations (μg/well): 10 μg for $hM_1$, 10-15 μg for $hM_2$, 10-20 μg for $hM_3$, 10-20 μg for $hM_4$, and 10-12 μg for $hM_5$ to get similar signals (cpm). The membranes were briefly homogenized using a Polytron tissue disruptor (10 seconds) prior to assay plate addition. Saturation binding studies for determining $K_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of $K_i$ values of test compounds were performed with [$^3$H]-NMS at 1 nM and eleven different test compound concentrations. The test compounds were initially dissolved to a concentration of 400 μM in dilution buffer and then serially diluted 5× with dilution buffer to final concentrations ranging from 10 μM to 100 μM. The addition order and volumes to the assay plates were as follows: 25 μL radioligand, 25 μL diluted test compound, and 50 pt membranes. Assay plates were incubated for 60 minutes at 37° C. Binding reactions were terminated by rapid filtration over GF/B glass fiber filter plates (PerkinElmer Inc., Wellesley, Mass.) pretreated in 1% BSA. Filter plates were rinsed three times with wash buffer (10 mM HEPES) to remove unbound radioactivity. The plates were then air dried and 50 μL Microscint-20 liquid scintillation fluid (PerkinElmer Inc., Wellesley, Mass.) was added to each well. The plates were then counted in a PerkinElmer Topcount liquid scintillation counter (PerkinElmer Inc., Wellesley, Mass.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $IC_D$ value of the radioligand using the Cheng-Prusoff equation (Cheng Y; Prusoff W H. (1973) *Biochemical Pharmacology,* 22(23):3099-108). K, values were converted to pK, values to determine the geometric mean and 95% confidence intervals. These summary statistics were then converted back to $K_i$ values for data reporting.

In this assay, a lower $K_i$ value indicates that the test compound has a higher binding affinity for the receptor tested. Exemplified compound of this invention that were tested in this assay typically were found to have a $K_i$ value of less than about 300 nM for the $M_3$ muscarinic receptor. For example, the compound of Example 1 was found to have K, values of less than 50 nM.

Assay Test Procedure C

Whole-Cell cAMP Flashplate Assay in CHO Cell Lines Heterologously Expressing Human $\beta_1$, $\beta_2$ or $\beta_3$ Adrenergic Receptors cAMP assays were performed in a radioimmunoassay format using the Flashplate Adenylyl Cyclase Activation Assay System with [$^{125}$I]-cAMP (NEN SMP004, PerkinElmer Life Sciences Inc., Boston, Mass.), according to the manufacturers instructions. For the determination of 13 receptor agonist potency ($EC_{50}$), CHO-K1 cell lines stably expressing cloned human $\beta_1$, $\beta_2$ or $\beta_3$ adrenergic receptors were grown to near confluency in HAM's F-12 media supplemented with 10% FBS and Geneticin (250 μg/mL). Cells were rinsed with PBS and detached in dPBS (Dulbecco's Phosphate Buffered Saline, without $CaCl_2$ and $MgCl_2$) containing 2 mM EDTA or Trypsin-EDTA solution (0.05% trypsin/0.53 mM EDTA). After counting cells in Coulter cell counter, cells were pelleted by centrifugation at 1,000 rpm and re-suspended in stimulation buffer containing IBMX (PerkinElmer Kit) prewarmed to room temperature to a concentration of $1.6\times10^6$ to $2.8\times10^6$ cells/mL. About 60,000 to 80,000 cells per well were used in this assay. Test compounds (10 mM in DMSO) were diluted into PBS containing 0.1% BSA in Beckman Biomek-2000 and tested at 11 different concentrations ranging from 100 μM to 1 μM. Reactions were incubated for 10 min at 37° C. and stopped by adding 100 μL of cold detection buffer containing [$^{125}$I]-cAMP (NEN SMP004, PerkinElmer Life Sciences, Boston, Mass.). The amount of cAMP produced (pmol/well) was calculated based on the counts observed for the samples and cAMP standards as described in the manufacturer's user manual. Data were analyzed by nonlinear regression analysis with the GraphPad Prism Software package (GraphPad Software, Inc., San Diego, Calif.) with the sigmoidal equation. The Cheng-Prusoff equation (Cheng Y, and Prusoff W H., *Biochemical Pharmacology,* 1973, 22, 23, 3099-108) was used to calculate the EC50 values.

In this assay, a lower $EC_{50}$ value indicates that the test compound has a higher functional activity at the receptor tested. Exemplified compound of this invention that were tested in this assay typically were found to have a $EC_{50}$ value of less than about 300 nM for the $\beta_2$ adrenergic receptor. For example, the compound of Example 1 was found to have $EC_{50}$ values of less than 10 nM.

If desired, the receptor subtype selectivity for a test compound can be calculated as the ratio of $EC_{50}(\beta_1)/EC_{50}(\beta_2)$ or $EC_{50}(\beta_3)/EC_{50}(\beta_2)$ Typically, compounds of this invention demonstrated greater functional activity at the $\beta_2$ adrenergic receptor compared to the $\beta_1$ or $\beta_3$ adrenergic receptor, i.e. $EC_{50}(\beta_1)$ or $EC_{50}(\beta_3)$ is typically greater than $EC_{50}(\beta_2)$. Generally, compounds having selectivity for the $\beta_2$ adrenergic receptor over the $\beta_1$ or $\beta_3$ adrenergic receptors are preferred; especially compounds having a selectivity greater than about 5; and in particular, greater than about 10. By way of example, the compound of Example 1 had ratios of $EC_{50}(\beta_1)/EC_{50}(\beta_2)$ greater than 10.

Assay Test Procedure D

Functional Assays of Antagonism for Muscarinic Receptor Subtypes

A. Blockade of Agonist-Mediated Inhibition of cAMP Accumulation

In this assay, the functional potency of a test compound was determined by measuring the ability of the test compound to block oxotremorine-inhibition of forskolin-mediated cAMP accumulation in CHO-K1 cells expressing the $hM_2$ receptor. cAMP assays were performed in a radioimmunoassay format using the Flashplate Adenylyl Cyclase Activation Assay System with $^{125}$I-cAMP (NEN SMP004B, PerkinElmer Life Sciences Inc., Boston, Mass.), according to the manufacturer's instructions. Cells were rinsed once with dPBS and lifted with Trypsin-EDTA solution (0.05% trypsin/0.53 mM EDTA) as described in the Cell Culture and Membrane Preparation section above. The detached cells were washed twice by centrifugation at 650×g for five minutes in 50 mL dPBS. The cell pellet was then re-suspended in 10 mL dPBS, and the cells were counted with a Coulter Z1 Dual Particle Counter (Beckman Coulter, Fullerton, Calif.). The cells were centrifuged again at 650×g for five minutes and re-suspended in stimulation buffer to an assay concentration of $1.6\times10^6$-$2.8\times10^6$ cells/mL.

The test compound was initially dissolved to a concentration of 400 μM in dilution buffer (dPBS supplemented with 1 mg/mL BSA (0.1%)), and then serially diluted with dilution buffer to final molar concentrations ranging from 100 μM to 0.1 nM. Oxotremorine was diluted in a similar manner.

To measure oxotremorine inhibition of adenylyl cyclase (AC) activity, 25 μL forskolin (25 μM final concentration diluted in dPBS), 25 μL diluted oxotremorine, and 50 μL cells were added to agonist assay wells. To measure the ability of a test compound to block oxotremorine-inhibited AC activity, 25 μL forskolin and oxotremorine (25 μM and 5 μM final concentrations, respectively, diluted in dPBS), 25 μL diluted test compound, and 50 μL cells were added to remaining assay wells.

Reactions were incubated for 10 minutes at 37° C. and stopped by addition of 100 μL ice-cold detection buffer. Plates were sealed, incubated overnight at room temperature and counted the next morning on a PerkinElmer TopCount liquid scintillation counter (PerkinElmer Inc., Wellesley, Mass.). The amount of cAMP produced (pmol/well) was calculated based on the counts observed for the samples and cAMP standards, as described in the manufacturer's user manual. Data was analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_i$, using the $EC_{50}$ of the oxotremorine concentration-response curve and the oxotremorine assay concentration as the $K_D$ and [L], respectively.

In this assay, a lower $K_i$ value indicates that the test compound has a higher functional activity at the receptor tested. Exemplified compound of this invention tested in this assay were found to have a $K_i$ value of less than about 300 nM for blockade of oxotremorine-inhibition of forskolin-mediated cAMP accumulation in CHO-K1 cells expressing the $hM_2$ receptor. For example, the compound of Example 1 was found to have a $K_i$ value of less than 50 nM for blockade of oxotremorine-inhibition of forskolin-mediated cAMP accumulation in CHO-K1 cells expressing the $hM_2$ receptor.

B. Blockade of Agonist-Mediated [$^{35}$S]GTPγS Binding

In a second functional assay, the functional potency of test compounds was determined by measuring the ability of the compounds to block oxotremorine-stimulated [$^{35}$S]GTPγS binding in CHO-K1 cells expressing the $hM_2$ receptor.

At the time of use, frozen membranes were thawed and then diluted in assay buffer with a final target tissue concentration of 5-10 μg protein per well. The membranes were briefly homogenized using a Polytron PT-2100 tissue disrupter and then added to the assay plates.

The $EC_{90}$ value (effective concentration for 90% maximal response) for stimulation of [$^{35}$S]GTPγS binding by the agonist oxotremorine was, determined in each experiment.

To determine the ability of a test compound to inhibit oxotremorine-stimulated [$^{35}$S]GTPγS binding, the following was added to each well of 96 well plates: 25 pt of assay buffer with [$^{35}$S]GTPγS (0.4 nM), 25 μL of oxotremorine ($EC_{90}$) and GDP (3 uM), 25 μL of diluted test compound and 25 μL CHO cell membranes expressing the $hM_2$ receptor. The assay plates were then incubated at 37° C. for 60 minutes. The assay plates were filtered over 1% BSA-pretreated GF/B filters using a PerkinElmer 96-well harvester. The plates were rinsed with ice-cold wash buffer for 3×3 seconds and then air or vacuum dried. Microscint-20 scintillation liquid (50 μL) was added to each well, and each plate was sealed and radioactivity counted on a Topcounter (PerkinElmer). Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_i$, using the $IC_{50}$ values of the concentration-response curve for the test compound and the oxotremorine concentration in the assay as the $K_D$ and [L], ligand concentration, respectively.

In this assay, a lower IC, value indicates that the test compound has a higher functional activity at the receptor tested. Exemplified compound of this invention tested in this assay were found to have a $K_i$ value of less than about 300 nM for blockade of oxotremorine-stimulated [$^{35}$S]GTPγS binding in CHO-K1 cells expressing the $hM_2$ receptor. For example, the compound of Example 1 was found to have a $K_i$ value of less than 50 nM for blockade of oxotremorine-stimulated [$^{35}$S]GTPγS binding in CHO-K1 cells expressing the $hM_2$ receptor.

C. Blockade of Agonist-Mediated Calcium Release via FLIPR Assays

Muscarinic receptor subtypes ($M_1$, $M_3$ and $M_5$ receptors), which couple to $G_q$ proteins, activate the phospholipase C (PLC) pathway upon agonist binding to the receptor. As a result, activated PLC hydrolyzes phosphatyl inositol diphosphate ($PIP_2$) to diacylglycerol (DAG) and phosphatidyl-1,4,5-triphosphate ($IP_3$), which in turn generates calcium release from intracellular stores, i.e., endoplasmic and sarcoplasmic reticulum. The FLIPR (Molecular Devices, Sunnyvale, Calif.) assay capitalizes on this increase in intracellular calcium by using a calcium sensitive dye (Fluo-4AM, Molecular Probes, Eugene, Oreg.) that fluoresces when free calcium binds. This fluorescence event is measured in real time by the FLIPR, which detects the change in fluorescence from a monolayer of cells cloned with human $M_1$ and $M_3$, and chimpanzee $M_5$ receptors. Antagonist potency can be determined by the ability of antagonists to inhibit agonist-mediated increases in intracellular calcium.

For FLIPR calcium stimulation assays, CHO cells stably expressing the $hM_1$, $hM_3$ and $cM_5$ receptors were seeded into 96-well FLIPR plates the night before the assay was done. Seeded cells were washed twice by Cellwash (MTX Labsystems, Inc.) with FLIPR buffer (10 mM HEPES, pH 7.4, 2 mM calcium chloride, 2.5 mM probenecid in Hank's Buffered Salt Solution (HBSS) without calcium and magnesium) to remove growth media and leaving 50 μL/well of FLIPR buffer. The cells were then incubated with 50 μL/well of 4 μM FLUO-4AM (a 2× solution was made) for 40 minutes at 37° C., 5% carbon dioxide. Following the dye incubation period, cells were washed two times with FLIPR buffer, leaving a final volume of 50 μL/well.

To determine antagonist potency, the dose-dependent stimulation of intracellular $Ca^{2+}$ release for oxotremorine was first determined so that antagonist potency can later be measured against oxotremorine stimulation at an $EC_{90}$ concentration. Cells were first incubated with compound dilution buffer for 20 minutes, followed by agonist addition, which was performed by the FLIPR. An $EC_{90}$ value for oxotremorine was generated according to the method detailed in the FLIPR measurement and data reduction section below, in conjunction with the formula $EC_F=((F/100-F)\hat{}1/H)*EC_{50}$. An oxotremorine concentration of $3\times EC_F$ is prepared in stimulation plates such that an $EC_{90}$ concentration of oxotremorine was added to each well in the antagonist inhibition assay plates.

The parameters used for the FLIPR were: exposure length of 0.4 seconds, laser strength of 0.5 watts, excitation wavelength of 488 nm, and emission wavelength of 550 nm. Baseline was determined by measuring the change in fluorescence for 10 seconds prior to addition of agonist. Following agonist stimulation, the FLIPR continuously measured the change of fluorescence every 0.5 to 1 second for 1.5 minutes to capture the maximum fluorescence change.

The change of fluorescence is expressed as maximum fluorescence minus baseline fluorescence for each well. The raw data was analyzed against the logarithm of drug concentration by nonlinear regression with GraphPad Prism (GraphPad Software, Inc., San Diego, Calif.) using the built-in model for sigmoidal dose-response. Antagonist $K_i$ values were determined by Prism using the oxotremorine $EC_{50}$ value as the $K_D$ and the oxotremorine $EC_{90}$ for the ligand concentration according to the Cheng-Prusoff equation (Cheng & Prusoff, 1973).

In this assay, a lower $K_i$ value indicates that the test compound has a higher functional activity at the receptor tested. Exemplified compound of this invention tested in this assay were found to have a $K_i$ value of less than about 300 nM for blockade of agonist-mediated calcium release in CHO cells stably expressing the $hM_3$ receptor. For example, the compound of Example 1 was were found to have a $K_i$ value of less than 50 nM for blockade of agonist-mediated calcium release in CHO cells stably expressing the $hM_3$ receptor.

Assay Test Procedure E

Whole-Cell cAMP Flashplate Assay With a Lung Epithelial Cell Line Endogenously Expressing Human $\beta_2$ Adrenergic Receptor For the determination of agonist potencies and efficacies (intrinsic activities) in a cell line expressing endogenous levels of the $\beta_2$ adrenergic receptor, a human lung epithelial cell line (BEAS-2B) is used (ATCC CRL-9609, American Type Culture Collection, Manassas, Va.) (January B, et al., *British Journal of Pharmacology,* 1998, 123, 4, 701-11). Cells are grown to 75-90% confluency in complete, serum-free medium (LHC-9 MEDIUM containing Epinephrine and Retinoic Acid, cat #181-500, Biosource International, Camarillo, Calif.). The day before the assay, medium is switched to LHC-8 (no epinephrine or retinoic acid, cat #141-500, Biosource International, Camarillo, Calif.). cAMP assays are performed in a radioimmunoassay format using the Flashplate Adenylyl Cyclase Activation Assay System with $[^{125}I]$-cAMP (NEN SMP004, PerkinElmer Life Sciences Inc., Boston, Mass.), according to the manufacturers instructions.

On the day of the assay, cells are rinsed with PBS, lifted by scraping with 5 mM EDTA in PBS, and counted. Cells are pelleted by centrifugation at 1,000 rpm and re-suspended in stimulation buffer pre-warmed to 37° C. at a final concentration of 600,000 cells/mL. Cells are used at a final concentration of 100,000 to 120,000 cells/well in this assay. Test compounds are serially diluted into assay buffer (75 mM Tris/HCl pH 7.4 at 25° C., 12.5 mM $MgCl_2$, 1 mM EDTA, 0.2% BSA) in Beckman Biomek-2000. Test compounds are tested in the assay at 11 different concentrations, ranging from 10 μM to 10 pM. Reactions are incubated for 10 min at 37° C. and stopped by addition of 100 μL of ice-cold detection buffer. Plates are sealed, incubated over night at 4° C. and counted the next morning in a Topcount scintillation counter (Packard BioScience Co., Meriden, Conn.). The amount of cAMP produced per mL of reaction is calculated based on the counts observed for samples and cAMP standards, as described in the manufacturer's user manual. Data are analyzed by nonlinear regression analysis with the GraphPad Prism Software package (GraphPad Software, Inc., San Diego, Calif.) using the 4-parameter model for sigmoidal dose-response.

In this assay, a lower $EC_{50}$ value indicates that the test compound has a higher functional activity at the receptor tested. Exemplified compound of this invention are expected to have a $EC_{50}$ value of less than about 300 nM for the $\beta_2$ adrenergic receptor when tested in this assay.

If desired, test compound efficacy (% Eff) is calculated from the ratio of the observed Emax (TOP of the fitted curve) and the maximal response obtained for isoproterenol dose response curve and is expressed as % Eff relative to isoproterenol. Exemplified compounds of this invention are expected to demonstrate a % Eff greater than about 40.

Assay Test Procedure F

Duration of Bronchoprotection in Guinea Pig Models of Acetylcholine-Induced or Histamine-Induced Bronchoconstriction These in vivo assays are used to assess the bronchoprotective effects of test compounds exhibiting both muscarinic receptor antagonist and $\beta_2$ adrenergic receptor agonist activity. To isolate muscarinic antagonist activity in the acetylcholine-induced bronchoconstriction model, the animals are administered propanolol, a compound that blocks β receptor activity, prior to the administration of acetylcholine. Duration of bronchoprotection in the histamine-induced bronchoconstriction model reflects $\beta_2$ adrenergic receptor agonist activity.

Groups of 6 male guinea pigs (Duncan-Hartley (HsdPoc: DH) Harlan, Madison, Wis.) weighing between 250 and 350 g are individually identified by cage cards. Throughout the study, animals are allowed access to food and water ad libitum.

Test compounds are administered via inhalation over 10 minutes in a whole-body exposure dosing chamber (R&S Molds, San Carlos, Calif.). The dosing chambers are arranged so that an aerosol is simultaneously delivered to 6 individual chambers from a central manifold. Guinea pigs are exposed to an aerosol of a test compound or vehicle (WFI). These aerosols are generated from aqueous solutions using an LC Star Nebulizer Set (Model 22F51, PARI Respiratory Equipment, Inc. Midlothian, Va.) driven by a mixture of gases ($CO_2$=5%, $O_2$=21% and $N_2$=74%) at a pressure of 22 psi. The gas flow through the nebulizer at this operating pressure is approximately 3 L/minute. The generated aerosols are driven into the chambers by positive pressure. No dilution air is used during the delivery of aerosolized solutions. During the 10 minute nebulization, approximately 1.8 mL of solution is nebulized. This value is measured gravimetrically by comparing pre- and post-nebulization weights of the filled nebulizer.

The bronchoprotective effects of test compounds administered via inhalation are evaluated using whole body plethysmography at 1.5, 24, 48 and 72 hours post-dose.

Forty-five minutes prior to the start of the pulmonary evaluation, each guinea pig is anesthetized with an intramuscular injection of ketamine (43.75 mg/kg), xylazine (3.50 mg/kg) and acepromazine (1.05 mg/kg). After the surgical site is shaved and cleaned with 70% alcohol, a 2-3 cm midline incision of the ventral aspect of the neck is made. Then, the jugular vein is isolated and cannulated with a saline-filled polyethylene catheter (PE-50, Becton Dickinson, Sparks, Md.) to allow for intravenous infusions of acetylcholine (Ach) or histamine in saline. The trachea is then dissected free and cannulated with a 14G teflon tube (#NE-014, Small Parts, Miami Lakes, Fla.). If required, anesthesia is maintained by additional intramuscular injections of the aforementioned anesthetic mixture. The depth of anesthesia is monitored and adjusted if the animal responds to pinching of its paw or if the respiration rate is greater than 100 breaths/minute.

Once the cannulations are completed, the animal is placed into a plethysmograph (#PLY3114, Buxco Electronics, Inc., Sharon, Conn.) and an esophageal pressure cannula (PE-160, Becton Dickinson, Sparks, Md.) is inserted to measure pulmonary driving pressure (pressure). The teflon tracheal tube is attached to the opening of the plethysmograph to allow the guinea pig to breathe room air from outside the chamber. The chamber is then sealed. A heating lamp is used to maintain body temperature and the guinea pig's lungs are inflated 3 times with 4 mL of air using a 10 mL calibration syringe (#5520 Series, Hans Rudolph, Kansas City, Mo.) to ensure that the lower airways did not collapse and that the animal did not suffer from hyperventilation.

Once it was determined that baseline values are within the range of 0.3-0.9 mL/cm $H_2O$ for compliance and within the range of 0.1-0.199 cm $H_2O$/mL per second for resistance, the pulmonary evaluation is initiated. A Buxco pulmonary measurement computer program enabled the collection and derivation of pulmonary values.

Starting this program initiated the experimental protocol and data collection. The changes in volume over time that occur within the plethysmograph with each breath are measured via a Buxco pressure transducer. By integrating this signal over time, a measurement of flow is calculated for each breath. This signal, together with the pulmonary driving pressure changes, which are collected using a Sensym pressure transducer (#TRD4100), is connected via a Buxco (MAX 2270) preamplifier to a data collection interface (#'s SFT3400 and SFT3813). All other pulmonary parameters are derived from these two inputs.

Baseline values are collected for 5 minutes, after which time the guinea pigs are challenged with Ach or histamine. When evaluating the muscarinic antagonist effects, propanolol (5 mg/Kg, iv) (Sigma-Aldrich, St. Louis, Mo.) is administered 15 minutes prior to challenge with Ach. Ach (Sigma-Aldrich, St. Louis, Mo.) (0.1 mg/mL) is infused intravenously for 1 minute from a syringe pump (sp210iw, World Precision Instruments, Inc., Sarasota, Fla.) at the following doses and prescribed times from the start of the experiment: 1.9 μg/minute at 5 minutes, 3.8 μg/minute at 10 minutes, 7.5 μg/minute at 15 minutes, 15.0 μg/minute at 20 minutes, 30 μg/minute at 25 minutes and 60 μg/minute at 30 minutes. Alternatively, bronchoprotection of test compounds is assessed in the acetylcholine challenge model without pretreatment with a beta blocking compound.

When evaluating the $\beta_2$ adrenergic receptor agonist effects of test compounds, histamine (25 μg/mL) (Sigma-Aldrich, St. Louis, Mo.) is infused intravenously for 1 minute from a syringe pump at the following doses and prescribed times from the start of the experiment: 0.5 μg/minute at 5 minutes, 0.9 μg/minute at 10 minutes, 1.9 μg/minute at 15 minutes, 3.8 μg/minute at 20 minutes, 7.5 μg/minute at 25 minutes and 15 μg/minute at 30 minutes. If resistance or compliance does not returned to baseline values at 3 minutes following each Ach or histamine dose, the guinea pig's lungs are inflated 3 times with 4 mL of air from a 10 mL calibration syringe. Recorded pulmonary parameters include respiration frequency (breaths/minute), compliance (mL/cm $H_2O$) and pulmonary resistance (cm $H_2O$/mL per second). Once the pulmonary function measurements are completed at minute 35 of this protocol, the guinea pig is removed from the plethysmograph and euthanized by carbon dioxide asphyxiation.

The data are evaluated in one of two ways:

(a) Pulmonary resistance ($R_L$, cm $H_2O$/mL per second) is calculated from the ratio of "change in pressure" to "the change in flow." The $R_L$ response to ACh (60 μg/min, 1H) is computed for the vehicle and the test compound groups. The mean ACh response in vehicle-treated animals, at each pre-treatment time, is calculated and used to compute % inhibition of ACh response, at the corresponding pre-treatment time, at each test compound dose. Inhibition dose-response curves for '$R_L$' were fitted with a four parameter logistic equation using GraphPad Prism, version 3.00 for Windows (GraphPad Software, San Diego, Calif.) to estimate bronchoprotective $ID_{50}$ (dose required to inhibit the ACh (60 μg/min) bronchocontrictor response by 50%). The equation used is as follows:

$$Y=\mathrm{Min}+(\mathrm{Max}-\mathrm{Min})/(1+10^{((\log ID50-X)*Hillslope)})$$

where X is the logarithm of dose, Y is the response (% Inhibition of ACh induced increase in $R_L$). Y starts at Min and approaches asymptotically to Max with a sigmoidal shape.

(b) The quantity $PD_2$, which is defined as the amount of Ach or histamine needed to cause a doubling of the baseline pulmonary resistance, is calculated using the pulmonary resistance values derived from the flow and the pressure over a range of Ach or histamine challenges using the following equation (which was derived from an equation used to calculate $PC_{20}$ values described in American Thoracic Society. Guidelines for methacholine and exercise challenge testing—1999. *Am J Respir Crit Care Med.* 2000; 161: 309-329):

$$PD_2 = \text{antilog}\left[\log C_1 + \frac{(\log C_2 - \log C_1)(2R_0 - R_1)}{R_2 - R_1}\right]$$

where:

$C_1$=concentration of Ach or histamine preceding $C_2$ $C_2$=concentration of Ach or histamine resulting in at least a 2-fold increase in pulmonary resistance ($R_L$)

$R_0$=Baseline $R_L$ value $R_1$=$R_L$ value after $C_1$ $R_2$=$R_L$ value after $C_2$ Statistical analysis of the data is performed using a two tailed-Students t-test. A P-value<0.05 was considered significant.

Exemplified compounds of this invention are expected to produce a dose-dependent bronchoprotective effect against MCh-induced bronchoconstriction and His-induced bronchoconstriction. Test compounds having a potency ($ID_{50}$ at 1.5 h post-dose) of less than about 300 μg/mL for ACh-induced bronchoconstriction and less than about 300 μg/mL for His-induced bronchoconstriction in this assay are generally preferred. Additionally, test compounds having a duration (PD $T_{1/2}$) of brochoprotective activity of at least about 24 hours in this assay are generally preferred.

Assay Test Procedure G

Einthoven Model for Measuring Changes in Ventilation in Guinea Pigs

The bronchodilator activity of test compounds is evaluated in an anesthetized guinea pig model (the Einthoven model), which uses ventilation pressure as a surrogate measure of airway resistance. See, for example, Einthoven (1892) *Pfugers Arch.* 51: 367-445; and Mohammed et al. (2000) *Pulm Pharmacol Ther.* 13(6):287-92. In this model, muscarinic antagonist and $\beta_2$ agonist activity is assessed by determining the protective effects against methacholine (MCh) and histamine (His)-induced bronchoconstriction.

This assay is conducted using Duncan-Hartley guinea pigs (Harlan, Indianapolis, Ind.), weighing between 300 and 400 g.

The test compound or vehicle (i.e., sterile water) is dosed by inhalation (IH) over a 10 minute time period in a whole body exposure dosing chamber (R+S Molds, San Carlos, Calif.) using 5 mL of dosing solution. Animals are exposed to an aerosol, which is generated from an LC Star Nebulizer Set (Model 22F51, PARI Respiratory Equipment, Inc. Midlothian, Va.) driven by Bioblend a mixture of gasses (5% $CO_2$; 21% $O_2$; and 74% $N_2$) at a pressure of 22 psi. Pulmonary function is evaluated at various time-points after inhalation dosing.

Forty five minutes prior to the start of pulmonary function evaluation, the guinea pigs are anesthetized with an intramuscular (IM) injection of a mixture of ketamine (13.7 mg/kg/ xylazine (3.5 mg/kg)/acepromazine (1.05 mg/kg). A supplemental dose of this mixture (50% of initial dose) is administered as needed. The jugular vein and carotid artery are isolated and cannulated with saline-filled polyethylene catheters (micro-renathane and PE-50, respectively, Beckton Dickinson, Sparks, Md.). The carotid artery is connected to a pressure transducer to allow the measurement of blood pressure and the jugular vein cannula is used for IV injection of either MCh or His. The trachea is then dissected free and cannulated with a 14G needle (#NE-014, Small Parts, Miami Lakes, Fla.). Once the cannulations are complete, the guinea pigs are ventilated using a respirator (Model 683, Harvard Apparatus, Inc., MA) set at a stroke volume of 1 mL/100 g body weight but not exceeding 2.5 mL volume, and at a rate of 100 strokes per minute. Ventilation pressure (VP) is measured in the tracheal cannula using a Biopac transducer that is connected to a Biopac (TSD 137C) pre-amplifier. Body temperature is maintained at 37° C. using a heating pad. Prior to initiating data collection, pentobarbital (25 mg/kg) is administered intraperitoneally (IP) to suppress spontaneous breathing and obtain a stable baseline. The changes in VP are recorded on a Biopac Windows data collection interface. Baseline values are collected for at least 5 minutes, after which time guinea pigs are challenged IV non-cumulatively with 2-fold incremental doses of the bronchoconstrictor (MCh or His). When MCh is used as the bronchoconstrictor agent, animals are pre-treated with propranolol (5 mg/kg, IV) to isolate the antimuscarinic effects of the test compound. Changes in VP are recorded using the Acknowledge Data Collection Software (Santa Barbara, Calif.). After the completion of study, the animals are euthanized.

Change in VP is measured in cm of water. Change in VP (cm $H_2O$)=peak pressure (after bronchoconstrictor challenge)−peak baseline pressure. The dose-response curve to MCh or His is fitted to a four parameter logistic equation using GraphPad Prism, version 3.00 for Windows (GraphPad Software, San Diego, Calif.). The equation used is as follows:

$$Y=\text{Min}+(\text{Max}-\text{Min})/(1+10^{((\log ID50-X)*Hillslope)})$$

where X is the logarithm of dose, Y is the response. Y starts at Min and approaches asymptotically to Max with a sigmoidal shape.

The percent inhibition of the bronchoconstrictor response to a submaximal dose of MCh or His is calculated at each dose of the test compound using the following equation: % Inhibition of response=100−((peak pressure (after bronchoconstrictor challenge, treated)−peak baseline pressure (treated) *100%/(peak pressure (after bronchoconstrictor challenge, water)−peak baseline pressure (water)). Inhibition curves are fitted using the four parameter logistic equation from GraphPad software. $ID_{50}$ (dose required to produce 50% inhibition of the bronchoconstrictor response) and Emax (maximal inhibition) are also estimated wherever appropriate.

The magnitude of bronchoprotection at different time-points after inhalation of the test compound is used to estimate the pharmacodynamic half-life (PD $T_{1/2}$). PD $T_{1/2}$ is determined using a non-linear regression fit using a one-phase exponential decay equation (GraphPad Prism, Version 4.00): Y=Span*exp(−K*X)+Plateau; Starts at Span+Plateau and decays to Plateau with a rate constant K. The PD $T_{1/2}$=0.69/K. Plateau is constrained to 0.

Exemplified compounds of this invention are expected to produce a dose-dependent bronchoprotective effect against MCh-induced bronchoconstriction and His-induced bronchoconstriction. Generally, test compounds having an $ID_{50}$ less than about 300 μg/mL for MCh-induced bronchoconstriction and an $ID_{50}$ less than about 300 μg/mL for His-induced bronchoconstriction at 1.5 hours post-dose in this assay are preferred. Additionally, test compounds having a duration (PD $T_{1/2}$) of brochoprotective activity of at least about 24 hours in this assay are generally preferred.

Assay Test Procedure H

Inhalation Guinea Pig Salivation Assay

Guinea pigs (Charles River, Wilmington, Mass.) weighing 200-350 g are acclimated to the in-house guinea pig colony for at least 3 days following arrival. Test compound or vehicle are dosed via inhalation (1H) over a 10 minute time period in a pie shaped dosing chamber (R+S Molds, San Carlos, Calif.). Test solutions are dissolved in sterile water and delivered using a nebulizer filled with 5.0 mL of dosing solution. Guinea pigs are restrained in the inhalation chamber for 30 minutes. During this time, guinea pigs are restricted to an area of approximately 110 sq. cm. This space is adequate for the animals to turn freely, reposition themselves, and allow for grooming. Following 20 minutes of acclimation, guinea pigs are exposed to an aerosol generated from a LS Star Nebulizer Set (Model 22F51, PARI Respiratory Equipment, Inc. Midlothian, Va.) driven by house air at a pressure of 22 psi. Upon completion of nebulization, guinea pigs are evaluated at 1.5, 6, 12, 24, 48, or 72 hrs after treatment.

Guinea pigs are anesthetized one hour before testing with an intramuscular (IM) injection of a mixture of ketamine 43.75 mg/kg, xylazine 3.5 mg/kg, and acepromazine 1.05 mg/kg at an 0.88 mL/kg volume. Animals are placed ventral side up on a heated (37° C.) blanket at a 20 degree incline with their head in a downward slope. A 4-ply 2×2 inch gauze pad (Nu-Gauze General-use sponges, Johnson and Johnson, Arlington, Tex.) is inserted in the guinea pig's mouth. Five minutes later, the muscarinic agonist pilocarpine (3.0 mg/kg, s.c.) is administered and the gauze pad is immediately discarded and replaced by a new pre-weighed gauze pad. Saliva is collected for 10 minutes, at which point the gauze pad is weighed and the difference in weight recorded to determine the amount of accumulated saliva (in mg). The mean amount of saliva collected for animals receiving the vehicle and each dose of test compound is calculated. The vehicle group mean is considered to be 100% salivation. Results are calculated using result means (n=3 or greater). Confidence intervals (95%) are calculated for each dose at each time point using two-way ANOVA. This model is a modified version of the procedure described in Rechter, "Estimation of anticholinergic drug effects in mice by antagonism against pilocarpine-induced salivation" *Ata Pharmacol Toxicol,* 1996, 24:243-254.

The mean weight of saliva in vehicle-treated animals, at each pre-treatment time, is calculated and used to compute % inhibition of salivation, at the corresponding pre-treatment time, at each dose. The inhibition dose-response data are fitted to a four parameter logistic equation using GraphPad Prism, version 3.00 for Windows (GraphPad Software, San Diego, Calif.) to estimate anti-sialagogue $ID_{50}$ (dose required to inhibit 50% of pilocarpine-evoked salivation). The equation used is as follows:

$$Y=\text{Min}+(\text{Max}-\text{Min})/(1+10^{((\log ID50-X)*Hillslope)})$$

where X is the logarithm of dose, Y is the response (% inhibition of salivation). Y starts at Min and approaches asymptotically to Max with a sigmoidal shape.

The ratio of the anti-sialagogue $ID_{50}$ to bronchoprotective $ID_{50}$ is used to compute the apparent lung-selectivity index of the test compound. Generally, compounds having an apparent lung-selectivity index greater than about 5 are preferred.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A process for preparing a compound of formula I:

I

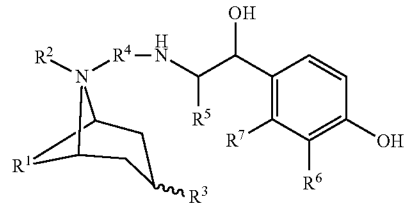

wherein $R^1$ represents —$CH_2CH_2$—, —CH=CH—, —$CH_2CH_2CH_2$—, —$CH_2CH(OCH_3)$— or

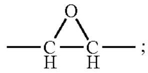

;

$R^2$ represents an electron pair or (1-6C)alkyl which is unsubstituted or substituted with a hydroxy group or from 1 to 3 fluoro substituents; provided that when $R^2$ is an alkyl group, the nitrogen atom to which it is attached is positively charged and a pharmaceutically acceptable anion, $X^-$, is present;

$R^3$ represents —$OC(O)CR^{3a}R^{3b}R^{3c}$ or —$NHC(O)R^{3d}$;

$R^{3a}$ represents hydrogen, hydroxy, (1-4C)alkyl or hydroxy (1-4C)alkyl;

$R^{3b}$ represents phenyl, (3-6C)cycloalkyl, (3-5C)heteroaryl or (3-5C)heterocyclyl; wherein each phenyl, cycloalkyl, heteroaryl and heterocyclyl group is unsubstituted or substituted with from 1 to 4 substituents selected independently from halo, (1-4C)alkyl and (1-4C)alkoxy; and wherein the heteroaryl and heterocyclyl groups contain 1 or 2 ring heteroatoms selected independently from oxygen, nitrogen and sulfur;

$R^{3c}$ represents hydrogen, phenyl, (3-6C)cycloalkyl, (3-5C) heteroaryl or (3-5C)heterocyclyl; wherein each phenyl, cycloalkyl, heteroaryl and heterocyclyl group is unsubstituted or substituted with from 1 to 4 substituents selected independently from halo, (1-4C)alkyl and (1-4C)alkoxy; and wherein the heteroaryl and heterocyclyl groups contain 1 or 2 ring heteroatoms selected independently from oxygen, nitrogen and sulfur;

or $R^{3b}$ and $R^{3c}$ together with $R^{3a}$ and the carbon atom to which they are attached form a group of formula (a):

(a)

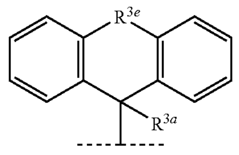

wherein $R^{3e}$ represents —O—, —S—, —$CH_2$—, —$CH_2CH_2$—, —$CH_2O$—, or —$CH_2S$—;

$R^{3d}$ represents an indazol-3-yl group which is unsubstituted or substituted with (1-4C)alkyl at the 1-position;

$R^4$ is a divalent group of the formula:

$$—(R^{4a})_d-(A^1)_e-(R^{4b})_f-Q-(R^{4c})_g-(A^2)_h-(R^{4d})_i—$$

wherein d, e, f, g, h and i are each independently selected from 0 and 1;

$R^{4a}$, $R^{4b}$, $R^{4c}$ and $R^{4d}$ are each independently selected from (1-10C)alkylene, (2-10C)alkenylene and (2-10C)alkynylene, wherein each alkylene, alkenylene or alkynylene group is unsubstituted or substituted with from 1 to 5 substituents independently selected from (1-4C)alkyl, fluoro, hydroxy, phenyl and phenyl-(1-4C)alkyl; or $R^{4d}$ represents (1-6C)alkylene-NHC(O)-(1-6C)alkylene;

$A^1$ and $A^2$ are each independently selected from (3-7C) cycloalkylene, (6-10C)arylene, —O-(6-10C)arylene, (6-10C)arylene-O—, (2-9C)heteroarylene, —O-(2-9C) heteroarylene, (2-9C)heteroarylene-O— and (3-6C)heterocyclene, wherein each cycloalkylene is unsubstituted or substituted with from 1 to 4 substituents selected independently from (1-4C)alkyl, and each arylene, heteroarylene or heterocyclene group is unsubstituted or substituted with from 1 to 4 substituents independently selected from halo, (1-4C)alkyl, (1-4C)alkoxy, —S-(1-4C)alkyl, —S(O)-(1-4C)alkyl, —$S(O)_2$-(1-4C)alkyl, —C(O)O(1-4C)alkyl, carboxy, cyano, hydroxy, nitro, trifluoromethyl and trifluoromethoxy;

Q is selected from a bond, —O—, —C(O)O—, —OC(O)—, —S—, —S(O)—, —$S(O)_2$—, —$N(Q^a)C(O)$—, —$C(O)N(Q^b)$-, —$N(Q^c)S(O)_2$—, —$S(O)_2N(Q^d)$-, —$N(Q^e)C(O)N(Q^f)$-, —$N(Q^g)S(O)_2N(Q^h)$-, —$OC(O)N(Q^i)$-, —N(O)C(O)O— and —$N(Q^k)$;

$Q^a$, $Q^b$, $Q^c$, $Q^d$, $Q^e$, $Q^f$, $Q^g$, $Q^h$, $Q^i$, $Q^j$ and $Q^k$ are each independently selected from hydrogen, (1-6C)alkyl, $A^3$ and (1-4C)alkylene-$A^4$, wherein the alkyl group is unsubstituted or substituted with from 1 to 3 substituents independently selected from fluoro, hydroxy and (1-4C) alkoxy; or together with the nitrogen atom and the group $R^{4b}$ or $R^{4c}$ to which they are attached, form a 4-6 membered azacycloalkylene group;

$A^3$ and $A^4$ are each independently selected from (3-6C) cycloalkyl, (6-10C)aryl, (2-9C)heteroaryl and (3-6C) heterocyclyl, wherein each cycloalkyl is unsubstituted or substituted with from 1 to 4 substituents selected independently from (1-4C)alkyl and each aryl, heteroaryl or heterocyclyl group is unsubstituted or substituted with from 1 to 4 substituents independently selected from halo, (1-4C)alkyl and (1-4C)alkoxy;

provided that the number of contiguous atoms in the shortest chain between the two nitrogen atoms to which $R^4$ is attached is in the range of from 4 to 16;

$R^5$ represents hydrogen or (1-4C)alkyl;

$R^6$ is —$NR^{6a}CR^{6b}(O)$ or —$CR^{6c}R^{6d}OR^{6e}$ and $R^7$ is hydrogen; or $R^6$ and $R^7$ together form —$NR^{7a}C(O)$—$CR^{7b}$═$CR^{7c}$—, —$CR^{7d}$═$CR^{7e}$—C(O)—$NR^{7f}$—, —$NR^{7g}C(O)$—$CR^{7h}R^{7i}$—$CR^{7j}R^{7k}$— or —$CR^{7l}R^{7m}$—$CR^{7n}R^{7o}$—C(O)—$NR^{7p}$—;

each of $R^{6a}$, $R^{6b}$, $R^{6c}$, $R^{6d}$ and $R^{6e}$ is independently hydrogen or (1-4C)alkyl; and each of $R^{7a}$, $R^{7b}$, $R^{7c}$, $R^{7d}$, $R^{7e}$, $R^{7f}$, $R^{7g}$, $R^{7h}$, $R^{7i}$, $R^{7j}$, $R^{7k}$, $R^{7l}$, $R^{7m}$, $R^{7n}$, $R^{7o}$ and $R^{7p}$ is independently hydrogen or (1-4C)alkyl;

or a salt or stereoisomer thereof; the process comprising:

(a) reacting a compound of formula 1:

1

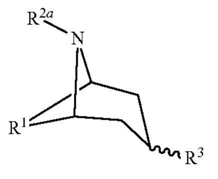

wherein $R^{2a}$ represents hydrogen or $R^2$; or a salt or protected derivative thereof; with a compound of formula 2:

2

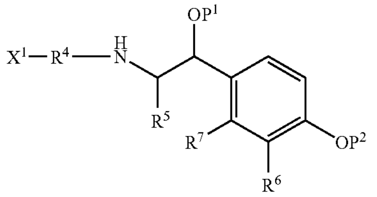

wherein $X^1$ represents a leaving group, and $P^1$ and $P^2$ each independently represent hydrogen or a hydroxy-protecting group;

(b) reacting a compound of formula 3:

3

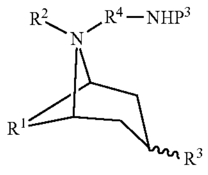

wherein $P^3$ represents hydrogen or an amino-protecting group, or salt or protected derivative thereof; with a compound of formula 4:

4

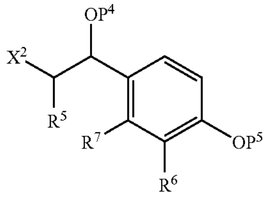

wherein $X^2$ represents a leaving group, and $P^4$ and $P^5$ each independently represent hydrogen or a hydroxy-protecting group;

(c) coupling a compound of formula 5:

5

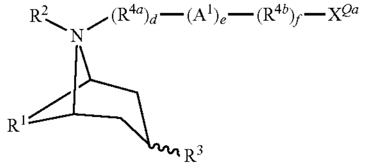

or a salt or protected derivative thereof; with a compound of formula 6:

6

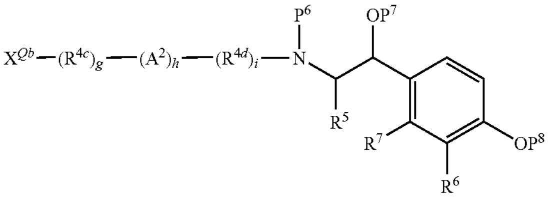

wherein $X^{Qa}$ and $X^{Qb}$ each independently represent functional groups that couple to form a group Q, $P^6$ represents hydrogen or an amino-protecting group; and $P^7$ and $P^8$ each independently represent hydrogen or a hydroxy-protecting group;

(d) for a compound of formula I wherein $R^5$ represents hydrogen, reacting a compound of formula 3 with a compound of formula 7:

7

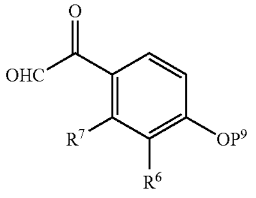

or a hydrate thereof (e.g., a glyoxal), wherein $P^9$ represents hydrogen or a hydroxy-protecting group, in the presence of a reducing agent;

(e) reacting a compound of formula 1 with a compound of formula 8:

8

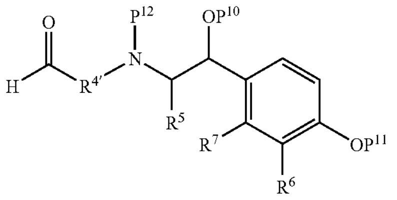

or a salt or hydrate or protected derivative thereof, in the presence of a reducing agent, wherein $P^{10}$ and $P^{11}$ each independently represent hydrogen or a hydroxy-protecting group; $P^{12}$ represents hydrogen or an amino-protecting group; and $R^{4'}$ represents a residue that, together with the carbon to which it is attached, affords a group $R^4$ upon completion of the reaction;

(f) reacting a compound of formula 9:

9

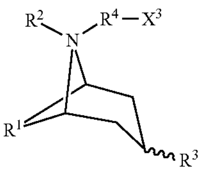

wherein $X^3$ represents a leaving group, or a salt or protected derivative thereof with a compound of formula 10:

10

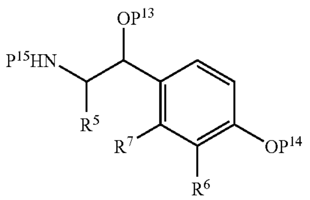

wherein $P^{13}$ and $P^{14}$ each independently represent hydrogen or a hydroxy-protecting group, and $P^{15}$ represents hydrogen or an amino-protecting group;

(g) reacting a compound of formula 11:

11

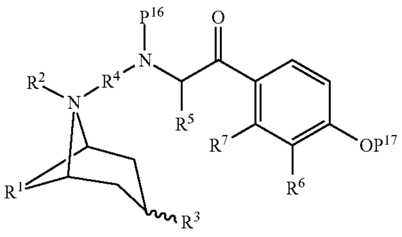

with a reducing agent; wherein $P^{16}$ represents hydrogen or an amino-protecting group; and $P^{17}$ represents hydrogen or a hydroxy-protecting group; or a salt or protected derivative thereof;

(h) reacting a compound of formula 12:

12

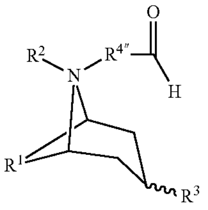

or a salt or hydrate or protected derivative thereof; wherein $R^{4''}$ represents a residue that, together with the carbon to which it is attached, affords an $R^4$ group upon completion of the reaction; with a compound of formula 10 in the presence of a reducing agent;

and then removing any protecting groups to provide a compound of formula I or a salt or stereoisomer thereof.

2. The process of claim 1, wherein the process further comprises forming a pharmaceutically acceptable salt of the compound of formula I.

3. The process of claim 1, wherein the compound of formula I is a compound having formula II:

II

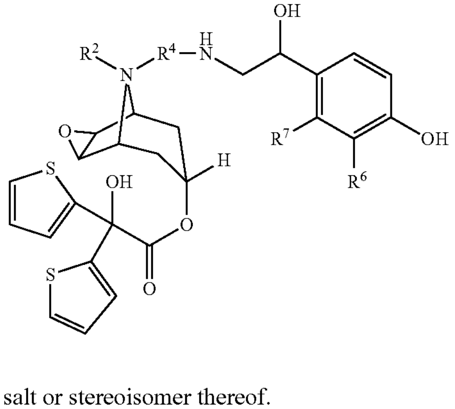

or a salt or stereoisomer thereof.

4. The process of claim 1, wherein the compound of formula I is a compound having formula III:

III

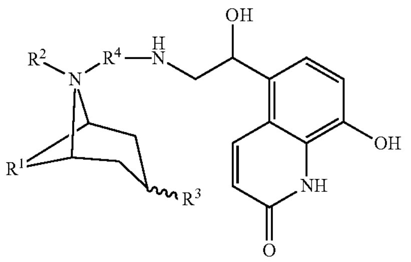

or a salt or stereoisomer thereof.

5. The process of claim 1, wherein the compound of formula I is a compound having formula IV:

IV

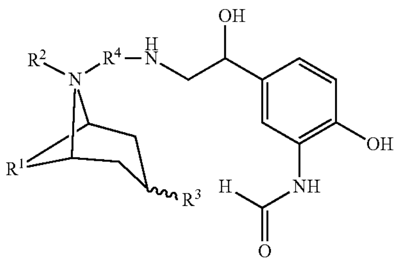

or a salt or stereoisomer thereof.

6. The process of claim 1, wherein the compound of formula I is a compound having formula V:

V

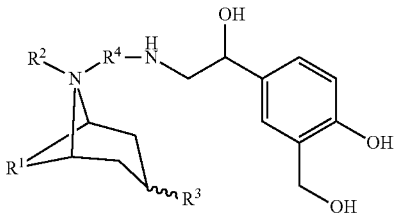

or a salt or stereoisomer thereof.

7. The process of claim 1, wherein $R^4$ is a divalent group of the formula: $—(R^{4a})_d—$ where $R^{4a}$ is (4-10C)alkylene.

8. The process of claim 1, wherein $R^4$ is a divalent group of the formula:

$$—(R^{4a})_d-(A^2)_h-(R^{4d})_i—$$

wherein $R^{4a}$ is (1-10C)alkylene; $A^2$ is (6-10C)arylene or (2-9C)heteroarylene; and $R^{4d}$ is (1-10C)alkylene.

9. The process of claim 1, wherein $R^4$ is selected from:

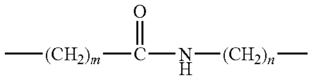

wherein m is an integer from 2 to 10; and n is an integer from 2 to 10; provided that m+n is an integer from 4 to 12;

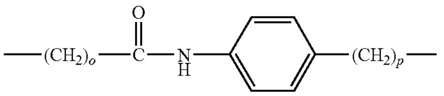

wherein o is an integer from 2 to 7; and p is an integer from 1 to 6; provided that o+p is an integer from 3 to 8; and wherein the phen-1,4-ylene group is optionally substituted with from 1 to 4 substituents independently selected from halo, (1-4C)alkyl, (1-4C)alkoxy, —S-(1-4C)alkyl, —S(O)-(1-4C)alkyl, $—S(O)_2$-(1-4C)alkyl, —C(O)O(1-4C)alkyl, carboxy, cyano, hydroxy, nitro, trifluoromethyl and trifluoromethoxy;

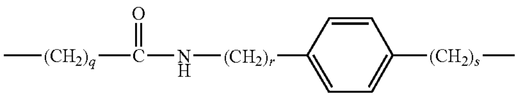

wherein q is an integer from 2 to 6; r is an integer from 1 to 5; and s is an integer from 1 to 5; provided that q+r+s is an integer from 4 to 8; and wherein the phen-1,4-ylene group is optionally substituted with from 1 to 4 substituents independently selected from halo, (1-4C)alkyl, (1-4C)alkoxy, —S-(1-4C)alkyl, —S(O)-(1-4C)alkyl, $—S(O)_2$-(1-4C)alkyl, —C(O)O(1-4C)alkyl, carboxy, cyano, hydroxy, nitro, trifluoromethyl and trifluoromethoxy;

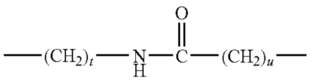

wherein t is an integer from 2 to 10; and u is an integer from 2 to 10; provided that t+u is an integer from 4 to 12;

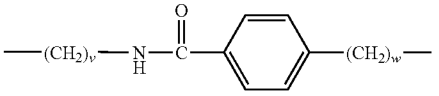

wherein v is an integer from 2 to 7; and w is an integer from 1 to 6; provided that v+w is an integer from 3 to 8; and wherein the phen-1,4-ylene group is optionally substituted with from 1 to 4 substituents independently selected from halo, (1-4C)alkyl, (1-4C)alkoxy, —S-(1-4C)alkyl, —S(O)-(1-4C)alkyl, $—S(O)_2$-(1-4C)alkyl, —C(O)O(1-4C)alkyl, carboxy, cyano, hydroxy, nitro, trifluoromethyl and trifluoromethoxy; and

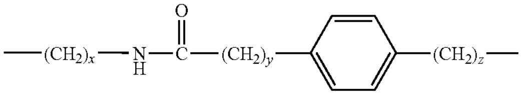

wherein x is an integer from 2 to 6; y is an integer from 1 to 5; and z is an integer from 1 to 5; provided that x+y+z is an integer from 4 to 8; and wherein the phen-1,4-ylene group is optionally substituted with from 1 to 4 substituents independently selected from halo, (1-4C)alkyl, (1-4C)alkoxy, —S-(1-4C)alkyl, —S(O)-(1-4C)alkyl, $—S(O)_2$-(1-4C)alkyl, —C(O)O(1-4C)alkyl, carboxy, cyano, hydroxy, nitro, trifluoromethyl and trifluoromethoxy.

* * * * *

UNITED STATES PATENT AND TRADEMARK OFFICE

CERTIFICATE OF CORRECTION

PATENT NO. : 7,893,256 B2
APPLICATION NO. : 12/756694
DATED : February 22, 2011
INVENTOR(S) : Mathai Mammen et al.

It is certified that error appears in the above-identified patent and that said Letters Patent is hereby corrected as shown below:

In Column 87, at line 23, "-N(O)C(O)O-" should read "-N($Q^j$)C(O)O-".

Signed and Sealed this
Twenty-fourth Day of May, 2011

David J. Kappos
*Director of the United States Patent and Trademark Office*